US006340566B1

(12) United States Patent
McCutchen-Maloney

(10) Patent No.: US 6,340,566 B1
(45) **Date of Patent: *Jan. 22, 2002**

(54) DETECTION AND QUANTITATION OF SINGLE NUCLEOTIDE POLYMORPHISMS, DNA SEQUENCE VARIATIONS, DNA MUTATIONS, DNA DAMAGE AND DNA MISMATCHES

(75) Inventor: Sandra L. McCutchen-Maloney, Pleasanton, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/651,656

(22) Filed: Aug. 29, 2000

Related U.S. Application Data

(60) Provisional application No. 60/192,764, filed on Mar. 28, 2000.

(51) Int. Cl.$^{7}$ .......................... C12Q 1/68; C12P 19/34; G01N 33/53

(52) U.S. Cl. ........................... 435/6; 435/7.1; 435/91.2

(58) Field of Search ............................ 435/6, 91.2, 7.1

(56) References Cited

U.S. PATENT DOCUMENTS 5,683,877 A * 11/1997 Lu-Chang et al. ............. 435/6
5,702,894 A * 12/1997 Modrich et al. ............... 435/6
5,736,330 A * 4/1998 Fulton .......................... 435/6
5,750,335 A * 5/1998 Gifford .......................... 435/6
5,919,623 A * 7/1999 Taylor ........................... 435/6
6,008,031 A * 12/1999 Modrich et al. ............ 435/200
6,027,877 A * 2/2000 Wagner, Jr. .................... 435/6
6,110,684 A * 8/2000 Kemper et al. ................ 435/6

FOREIGN PATENT DOCUMENTS

EP 0-596 028 B1 * 5/1994
WO 99/22029 * 5/1999

* cited by examiner

*Primary Examiner*—Kenneth R. Horlick
(74) *Attorney, Agent, or Firm*—Michael R. Ward; Alan H. Thompson

(57) ABSTRACT

DNA mutation binding proteins alone and as chimeric proteins with nucleases are used with solid supports to detect DNA sequence variations, DNA mutations and single nucleotide polymorphisms. The solid supports may be flow cytometry beads, DNA chips, glass slides or DNA dips sticks. DNA molecules are coupled to solid supports to form DNA-support complexes. Labeled DNA is used with unlabeled DNA mutation binding proteins such at TthMutS to detect DNA sequence variations, DNA mutations and single nucleotide length polymorphisms by binding which gives an increase in signal. Unlabeled DNA is utilized with labeled chimeras to detect DNA sequence variations, DNA mutations and single nucleotide length polymorphisms by nuclease activity of the chimera which gives a decrease in signal.

100 Claims, 2 Drawing Sheets

DETECTION AND QUANTITATION OF SINGLE NUCLEOTIDE POLYMORPHISMS, DNA SEQUENCE VARIATIONS, DNA MUTATIONS, DNA DAMAGE AND DNA MISMATCHES

RELATED APPLICATION

This application claims the benefit under 35 U.S.C. §119 (e) of U.S. Provisional patent application No. 60/192,764, filed Mar. 28, 2000, which is hereby incorporated by reference in its entirety. Furthermore, this application relates to applicant's related co-pending application Ser. No. 09/650, 855 entitled CHIMERIC PROTEINS FOR DETECTION AND QUANTITATION OF DNA MUTATIONS. DNA SEQUENCE VARIATIONS, DNA DAMAGE AND DNA MISMATCHES filed simultaneously with this application and which is hereby incorporated by reference in its entirety.

The United States Government has rights in this invention pursuant to Contract No. W-7405-ENG-48 between the U.S. Department of Energy and the University of California, for the operation of Lawrence Livermore National Laboratory.

FIELD OF THE INVENTION

The present invention relates to the field of molecular biology, and more particularly, detection of single nucleotide polymorphisms, DNA sequence variation DNA mutations, DNA damage and DNA base pair mismatches. In particular, the invention relates to the use of DNA mutation binding proteins to detect single nucleotide polymorphisms, DNA sequence variations, DNA mutations, damaged DNA and DNA with mismatched base pairs.

BACKGROUND OF THE INVENTION

Natural DNA sequence variation exists in identical genomic regions of DNA among individual members of a species. It is of interest to identify similarities and differences in such genomic regions of DNA because such information can help identify sequences involved in susceptibility to disease states as well as provide genetic information for characterization and analysis of genetic material.

When a cell undergoes reproduction, its DNA molecules are replicated and precise copies are passed on to its descendants. The linear base sequence of a DNA molecule is maintained during replication by complementary DNA base pairing. Occasionally, an incorrect base pairing does occur during DNA replication, which, after further replication of the new strand, results in a double-stranded DNA offspring with a sequence containing a heritable single base difference from that of the parent DNA molecule. Such heritable changes are called "genetic polymorphisms," "genetic mutations," "single base pair mutations," "point mutations" or simply, "DNA mismatches". In addition to random mutations during DNA replication, organisms are constantly bombarded by endogenous and exogenous genotoxic agents which injure or damage DNA. Such DNA damage or injury can result in the formation of DNA mismatches or DNA mutations such as insertions or deletions.

The consequences of natural DNA sequence variation, DNA mutations, DNA mismatches and DNA damage range from negligible to lethal, depending on the location and effect of the sequence change in relation to the genetic information encoded by the DNA. In some instances, natural DNA sequence variation, DNA mutations, DNA mismatches and DNA damage can lead to cancer and other diseases of which early detection is critical for treatment.

There is thus a tremendous need to be able to rapidly identify differences in DNA sequences among individuals. In addition there is a need to identify DNA mutations, DNA mismatches and DNA damage to provide for early detection of cancer and other.

SUMMARY OF THE INVENTION

In order to meet these needs, the present invention concerns the use of proteins that function biologically to recognize DNA mutations to detect and map single nucleotide polymorphisms, DNA mutations, DNA mismatches and DNA damage.

In one embodiment, the present invention is directed to a method for detecting a DNA mutation in a DNA molecule comprising the steps of: (a) obtaining a solid support to which the DNA molecule is coupled; (b) forming a mixture by mixing the solid support (with DNA attached) and a labeled DNA mutation binding protein, the labeled DNA mutation binding protein being capable of detecting DNA mutations and binding to such mutated DNA; (c) forming a reacted sample by incubating the mixture under conditions wherein if the DNA molecule includes mutated DNA, the DNA damage binding protein binds to the mutated DNA; (d) analyzing the reacted sample by detecting the label on the solid support to detect the DNA mutation or absence thereof.

In another embodiment, the present invention is directed to a method for detecting a DNA mutation in a DNA molecule, said method comprising the steps of: (a) obtaining a solid support to which the DNA molecule is coupled wherein the DNA molecule is labeled; (b) forming a mixture by mixing the solid support (with labeled DNA attached) and a chimeric protein wherein the chimeric protein includes a DNA mutation binding protein and a nuclease and wherein the labeled DNA mutation binding protein is capable of detecting DNA mutations and binding to such mutated DNA; (c) forming a reacted sample by incubating the mixture under conditions wherein if the DNA molecule includes mutated DNA, the DNA damage binding protein binds to the mutated DNA and the nuclease cleaves the DNA thereby removing the label from DNA molecule coupled to said solid support and (d) analyzing the reacted sample by detecting the label or absence thereof on the solid support to detect the DNA mutation.

In another embodiment, the present invention is directed to a method of detecting a DNA mutation by a) obtaining a DNA molecule; b) coupling the DNA molecule to a flow cytometry bead to form a DNA-bead complex; c) forming a mixture by mixing the DNA-bead complex with a labeled DNA mutation binding protein; d) forming a reacted sample by incubating the mixture under conditions wherein if the DNA molecule includes mutated DNA the DNA mutation binding protein binds to the mutated DNA and e) analyzing the reacted sample by flow cytometry to determine the amount of label on the beads.

The present invention is also directed to a method for flow cytometric analysis to detect a DNA mutation in a DNA molecule by a) obtaining flow cytometry beads coupled to the DNA molecule; b) forming a mixture by mixing the beads and a labeled DNA mutation binding protein wherein the DNA mutation binding protein is capable of detecting DNA mutations and binding to such mutated DNA; c) forming a reacted sample by incubating said mixture under conditions wherein if the DNA molecule includes mutated DNA the DNA mutation binding protein binds to the mutated DNA; d) analyzing the reacted sample by flow cytometry to determine the amount of label on the bead; and e) detecting the DNA mutation or absence thereof by determining the amount of label on the beads.

In an alternative embodiment, the present invention is directed to a method for detecting a DNA mutation in a DNA molecule comprising the steps of: (a) obtaining a first DNA molecule; (b) coupling the first DNA molecule to a solid support to form a DNA-support complex; (c) obtaining a second DNA molecule; (d) forming a first mixture by mixing the second DNA molecule with the DNA-support complex; (e) incubating the first mixture under conditions such that the second DNA molecule hybridizes to the first DNA molecule thereby forming a hybrid double stranded DNA molecule coupled to the support wherein the hybrid DNA molecule includes one DNA strand from said the DNA molecule and one strand from the second DNA molecule; (f) obtaining a labeled DNA mutation binding protein, wherein the labeled DNA mutation binding protein is capable of detecting DNA mutations and binding to such mutated DNA; (g) forming a second mixture by mixing the labeled DNA mutation binding protein with the hybrid double stranded DNA molecule coupled to said support; (h) forming a reacted sample by incubating the second mixture under conditions wherein if the hybrid double stranded DNA molecule includes mutated DNA, the labeled DNA mutation binding protein binds to the mutated DNA and forms a labeled, hybrid double stranded DNA-support complex; (i) analyzing the reacted sample to detect the label or absence thereof on the hybrid double stranded DNA-support complex to thereby identify the DNA mutation.

The first DNA molecule may be coupled to the bead as single stranded DNA or as double stranded DNA and then converted to single stranded DNA by increasing the temperature or by placing the coupled DNA under conditions sufficiently stringent to convert the double stranded DNA to single stranded DNA. Similarly, the second DNA molecule may be added to the first mixture as single stranded DNA or as double stranded DNA and then converted to single stranded DNA by increasing the temperature or by placing the first mixture under conditions sufficiently stringent to convert the double stranded DNA to single stranded DNA.

In this embodiment, the nucleotide sequence of the first, single stranded DNA molecule may be known and the nucleotide sequence of said second, single stranded DNA molecule may be unknown. Where the first, single stranded DNA molecule is known the first DNA molecule may be wild type or mutant DNA and the second DNA molecule may be isolated from a host.

In an alternative format, the nucleotide sequence of the first DNA molecule may be unknown and the nucleotide sequence of the second DNA molecule may be known. Where the first DNA molecule is unknown the first single stranded DNA may be isolated from a host and the second DNA molecule may be wild type or mutant DNA.

In the method the DNA mutation may be a single nucleotide polymorphism in the first DNA molecule or the second DNA molecule or both DNA molecules.

In an alternative embodiment, the present invention is directed to a method for detecting DNA sequence variation between two DNA molecules comprising the steps of: (a) obtaining a first DNA molecule; (b) coupling the first DNA molecule to a solid support to form a DNA-support complex; (c) obtaining a second DNA molecule; (d) forming a first mixture by mixing the second DNA molecule with the DNA-support complex; (e) incubating the first mixture under conditions such that the second DNA molecule hybridizes to the first DNA molecule thereby forming a hybrid double stranded DNA molecule coupled to the support wherein the hybrid DNA molecule includes one DNA strand from said the DNA molecule and one strand from the second DNA molecule; (f) obtaining a labeled DNA mutation binding protein, wherein the labeled DNA mutation binding protein is capable of detecting DNA mutations and binding to such mutated DNA; (g) forming a second mixture by mixing the labeled DNA mutation binding protein with the hybrid double stranded DNA molecule coupled to said support; (h) forming a reacted sample by incubating the second mixture under conditions wherein if the hybrid double stranded DNA molecule includes mutated DNA, the labeled DNA mutation binding protein binds to the mutated DNA and forms a labeled, hybrid double stranded DNA-support complex; (i) analyzing the reacted sample to detect the label or absence thereof on the hybrid double stranded DNA-support complex to thereby identify the DNA mutation and detect the DNA sequence variation.

The DNA sequence variation may be a single nucleotide polymorphism.

The first DNA molecule may be coupled to the bead as single stranded DNA or as double stranded DNA and then converted to single stranded DNA by increasing the temperature or by placing the coupled DNA under conditions sufficiently stringent to convert the double stranded DNA to single stranded DNA. Similarly, the second DNA molecule may be added to the first mixture as single stranded DNA or as double stranded DNA and then converted to single stranded DNA by increasing the temperature or by placing the first mixture under conditions sufficiently stringent to convert the double stranded DNA to single stranded DNA.

In this embodiment, the nucleotide sequence of the first, single stranded DNA molecule may be known and the nucleotide sequence of said second, single stranded DNA molecule may be unknown. Where the first, single stranded DNA molecule is known the first DNA molecule may be wild type or mutant DNA and the second DNA molecule may be isolated from a host.

In an alternative format, the nucleotide sequence of the first DNA molecule may be unknown and the nucleotide sequence of the second DNA molecule may be known. Where the first DNA molecule is unknown the first single stranded DNA may be isolated from a host and the second DNA molecule may be wild type or mutant DNA.

In the methods of the invention, the host may be selected from the group consisting of humans, non-human animals, plants and microorganisms.

In the methods of the invention, the solid support may be a flow cytometry bead, a dipstick, a glass slide or a DNA chip. The label may be fluorescent, chemilluminescent or radioactive. In one embodiment the label is biotin. The DNA molecule may be a PCR product.

DNA mutation binding proteins which find use in the methods of the invention include human MutS homologue2 (hMSH2), xeroderma pigmentosum complementation group A (XPA), xeroderma pigmentosum complementation group C (XPC), xeroderma pigmentosum complementation group E (XPE), *Thermus thermophilus* Mut S (TthMutS), thymine DNA glycosylase (TDG), *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase (MutY), *Escherechia coli* Uvr A, *Escherechia coli* Uvr B and other DNA mutation binding proteins.

The DNA mutation binding proteins of the invention include those proteins having amino acid sequences depicted in SEQ ID NO:1, 3, 7, 9, 11, 15, 19, 21, 23, 25, 29, 31, 39, 35, 37, 101 and 103.

The DNA mutation binding proteins of the invention may be in the form of a chimeric protein. The chimeric proteins generally have sequences presented by the formulae: A-L-B and B-L-A wherein A is a peptide having DNA mutation binding activity and capable of binding to mutated DNA, B is a peptide having nuclease activity and L is a linker peptide. The chimeric proteins are linked in such a manner as to produce a single protein which retains the biological activity of both A and B.

Nucleases which find use in the chimeric proteins of the invention include the N-terminus of human excision repair cross-complementing rodent repair deficiency (XPF), *Serratia marcescens* nuclease, *Escherechia coli* Fpapy-DNA glycosylase; *Escherechia coli* endonuclease III; *Escherechia coli* endonuclease IV; T4 endonuclease; *Escherechia coli* uracil DNA glycosylase and *Escherechia coil* A/G-specific adenine DNA glycosylase, *Escherechia coli* Uvr B and *Escherechia coli* Uvr C.

The nucleases include those proteins having amino acids depicted in SEQ ID NO:5, 11, 13, 25, 31, 39, 35, 37, 103 and 105.

The linker peptide of the chimeric peptide of the invention generally consists of 8 amino acids rich in glycine and proline or other amino acids known to disrupt protein secondary structure. For example, the sequence GSGPSPGS (SEQ ID NO:17) finds use in the invention. However, in some circumstances the linker peptides will be as short as zero amino acids where the nuclease and DNA binding protein retain activity in the absence of a linker peptide. In other circumstances the peptide will have up to 5, 6,7, 8, 9 10, 11–15, 16–20 or 21–30 amino acids.

BRIEF DESCRIPTION OF THE SEQUENCE LISTING

Figure 1:
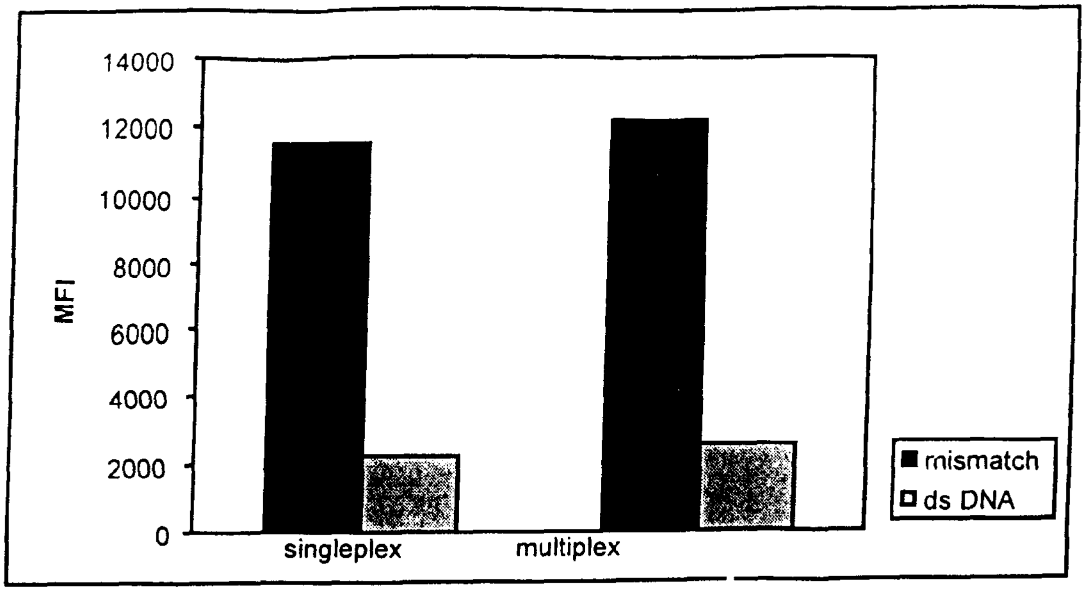
FIG. 1 shows the results of a flow cytometry assay comparing the mean fluorescent intensity detected for mismatched and non-mismatched DNA using biotin labeled MutS as a detection protein.

SEQ ID NO:1 shows amino acids 637–877 of human Mut S homologue 2, hMSH2.

SEQ ID NO:2 shows the DNA sequence encoding amino acids 637–877 of hMSH2.

SEQ ID NO:3 shows the protein sequence of the full-length sequence of hMSH2.

SEQ ID NO:4 shows the DNA sequence encoding the full-length sequence of hMSH2.

SEQ ID NO:5 shows the full-length protein sequence of the *Serratia marcescens* nuclease (Nuc).

SEQ ID NO:6 shows the DNA sequence of the full-length *Serratia marcescens* nuclease (Nuc).

SEQ ID NO:7 shows the protein sequence of the human xeroderma pigmentosum, complementation group A (XPA).

SEQ ID NO:8 shows the DNA sequence of the human xeroderma pigmentosum, complementation group A (XPA).

SEQ ID NO:9 shows amino acids 98–219 of human XPA.

SEQ ID NO:10 shows the DNA sequence encoding amino acids 98–219 of human XPA.

SEQ ID NO:11 shows the N-terminus (amino acids 12–378) of human excision repair cross-complementing rodent repair deficiency, complementation group 4 (XPF, also referred to as ERCC4).

SEQ ID NO:12 shows the DNA sequence encoding the N-terminus (amino acids 12–378) of human excision repair cross-complementing rodent repair deficiency, complementation group 4 (XPF, also referred to as ERCC4).

SEQ ID NO:13 shows the full-length protein sequence of human excision repair cross-complementing rodent repair deficiency, complementation group 4 (XPF).

SEQ ID NO:14 shows the DNA sequence of the full-length human excision repair cross-complementing rodent repair deficiency, complementation group 4 (XPF, also referred to as ERCC4).

SEQ ID NO:15 shows the protein sequence of the *Thermus thermophilus* MutS heat stable DNA mutation binding protein.

SEQ ID NO: 16 shows the DNA sequence of the *Thermus thermophilus* MutS (TthMuts) gene for the heat stable DNA mutation binding protein.

SEQ ID NO:17 shows a synthetic linker peptide sequence.

SEQ ID NO:18 shows the DNA sequence encoding a synthetic peptide linker.

SEQ ID NO:19 shows the protein sequence of human xeroderma pigmentosum, complementation group C (XPC).

SEQ ID NO:20 shows the DNA sequence of the human xeroderma pigmentosum, complementation group C (XPC).

SEQ ID NO:21 shows the protein sequence of the human xeroderma pigmentosum group E, UV-damaged binding factor, XPE.

SEQ ID NO:22 shows the DNA sequence of the human xeroderma pigmentosum group E, UV-damaged binding factor, XPE.

SEQ ID NO:23 shows the protein sequence of *Escherechia coli* Fapy-DNA glycosylase, Fpg.

SEQ ID NO:24 shows the DNA sequence of the *Escherechia coli* fpg gene for Fapy-DNA glycosylase, Fpg.

SEQ ID NO:25 shows the protein sequence of *Escherechia coli* endonuclease III, Endo III.

SEQ ID NO:26 shows the DNA sequence of the *Escherechia coli* nth gene encoding endonuclease III, Endo III.

SEQ ID NO:27 shows the protein sequence of *Escherechia coli* endonuclease VII, Endo VIII.

SEQ ID NO:28 shows the DNA sequence of *Escherechia coli* gene encoding endonuclease VII, Endo VIII.

SEQ ID NO:29 shows the protein sequence of the *Escherechia coli* exonuclease III, Exo III.

SEQ ID NO:30 shows the DNA sequence of *Escherechia coli* xthA gene encoding exonuclease III, Exo III.

SEQ ID NO:31 shows the protein sequence of the *Escherechia coli* endonuclease IV, Endo IV.

SEQ ID NO:32 shows the DNA sequence of *Escherechia coli* nfo gene encoding endonuclease IV, Endo IV.

SEQ ID NO:33 shows the protein sequence for a synthetic T4 endonuclease V, T4 endo.

SEQ ID NO:34 shows the DNA sequence for a synthetic T4 endonuclease V (T4endV) gene, T4 endo V.

SEQ ID NO:35 shows the protein sequence of the *Escherechia coli* uracil DNA glycosylase, ung.

SEQ ID NO:36 shows the DNA sequence of the *Escherechia coli* ung gene encoding uracil DNA glycosylase, ung.

SEQ ID NO:37 shows the protein sequence of *Escherechia coli* (strain K-12) A/G-specific adenine glycosylase, MutY.

SEQ ID NO:38 shows the DNA sequence of *Escherechia coli* (strain K-12 ) A/G-specific adenine glycosylase (micA) gene, MutY.

SEQ ID NO:39 shows the protein sequence of a synthetic T4 endonuclease, T4 endo.

SEQ ID NO:40 shows the DNA sequence of a synthetic T4 endonuclease (T4endV) gene, T4 endo.

SEQ ID NO:41 shows the protein sequence of *Mehtanococcus thermoautotropicum* thymine DNA-glycosylase (TDG).

SEQ ID NO:42 shows the DNA sequence of *Mehtanococcus thermoautotropicum* thymine DNA-glycosylase (TDG).

SEQ ID NO:43–44 show PCR primers for amplification of XPF at the N-terminus.

SEQ ID NO:45–46 show PCR primers for amplification of XPF at the C-terminus.

SEQ ID NO:47–48 show PCR primers for the amplification of the XPA domain at the N-terminus.

SEQ ID NO:49–50 show PCR primers for the amplification of the XPA domain at the C-terminus.

SEQ ID NO:51–52 show PCR primers for the amplification of the hMSH2 domain at the N-terminus.

SEQ ID NO:53–54 show PCR primers for the amplification of the hMSH2 domain at the C-terminus.

SEQ ID NO:55–56 show PCR primers for the amplification of Nuc at the N-terminus.

SEQ ID NO:57–58 show PCR primers used to amplify the XPF-XPA cDNA chimera.

SEQ ID NO:59–60 show PCR primers used to amplify the XPF-hMSH2 cDNA chimera.

SEQ ID NO:61–62 show PCR primers used to amplify the XPA-XPF cDNA chimera.

SEQ ID NO:63–64 show the PCR primers used to amplify the hMSH2-XPF cDNA chimera.

SEQ ID NO:65–66 show the PCR primers used to amplify Nuc-hMSH2 cDNA chimera.

SEQ ID NO:67–68 show the PCR primers used to amplify the Nuc-XPA cDNA chimera.

SEQ ID NO:69–70 show PCR primers for amplification of MutS at the N-terminus.

SEQ ID NO:71–72 show PCR primers for amplification of MutS at the C-terminus.

SEQ ID NO:73–74 show PCR primers for amplification of NucA at the N-terminus.

SEQ ID NO:75–76 show PCR primers for the amplification of the XPF domain at the N-terminus.

SEQ ID NO:77–78 show PCR primers for the amplification of XPF domain at the C-terminus.

SEQ ID NO:79–80 show the PCR primers used to amplify the MutS-XPF cDNA chimera.

SEQ ID NO:81–82 show the PCR primers used to amplify the XPF-MutS cDNA chimera.

SEQ ID NO:83–84 show the PCR primers used to amplify the Nuc-MutS cDNA chimera.

SEQ ID NO:85–86 show PCR primers used to amplify XPA at the N-terminus.

SEQ ID NO:87–88 show the PCR primers used to amplify XPA at the C-terminus.

SEQ ID NO:89–90 show the PCR primers used to amplify Nuc at the N-terminus.

SEQ ID NO:91–92 show the PCR primers used to amplify XPF at the N-terminus.

SEQ ID NO:93–94 show the PCR primers used to amplify XPF at the C-terminus.

SEQ ID NO:95–96 show the PCR primers used to amplify the XPA-XPF cDNA chimera.

SEQ ID NO:97–98 show the PCR primers used to amplify the XPF-XPA cDNA chimera.

SEQ ID NO:99–100 show the PCR primers used to amplify the Nuc-XPA cDNA chimera.

SEQ ID NO:101 shows the protein sequence of *Escherechia coli* Uvr A DNA-binding protein.

SEQ ID NO:102 shows the DNA sequence of the *Escherechia coli* UVr A DNA-binding protein gene.

SEQ ID NO:103 shows the protein sequence of *Escherechia coli* Uvr B nuclease and damage recognition protein.

SEQ ID NO:104 shows the DNA sequence of the *Escherechia coli* UVr B nuclease and damage recognition protein gene.

SEQ ID NO:105 shows the protein sequence of *Escherechia coli* Uvr C nuclease.

SEQ ID NO: 106 shows the DNA sequence of the *Escherechia coli* UVr C nuclease.

DETAILED DESCRIPTION OF THE INVENTION

In order to more completely understand the invention, the following definitions are provided.

DNA Sequence Variability: DNA Sequence Variability is the DNA sequence variation between one DNA sequence and a second DNA sequence. Either the first or the second DNA sequence may be a reference or control sequence such as a wild type sequence. DNA sequence variability is the differences in the DNA sequence between the reference or control sequence and another sequence of interest.

Two DNA sequences of interest may be compared by hybridization under conditions which permit base pairing between the two strands. Differences in the two sequences result in mismatches or mutations in the hybrid.

Single Nucleotide Polymorphism (SNP): Single Nucleotide Polymorphisms are variations is the genetic sequence of an organism including humans. It is estimated that the average human will have a SNP every 1000 base pairs (3 billion base pairs in the human genome). Many SNPs are nonconsequential; however, some may render the organism prone to disease.

DNA Mutation: A DNA mutation or mutated DNA is a change in a DNA sequence from a normal or wildtype sequence to a mutated or different sequence. DNA mutations include genetic mutations, single base pair mutations, point mutations, DNA mismatches, DNA insertions, DNA deletions, DNA transversions, DNA transitions, frameshift mutations, damaged DNA, and other changes or alterations in a normal or wild type DNA sequence.

DNA Transition: A DNA transition is a change in a DNA sequence involving the substitution of one purine or pyrimidine for the other (e.g., adenine for guanine, cytosine for thymidine or vice versa).

DNA Transversion: A DNA transversion is a change in a DNA sequence in which a purine is substituted for a pyrimidine or vice versa (e.g., adenine for cytosine or thymidine, guanine for cytosine or thymidine or vice versa).

DNA Insertion: A DNA insertion is the addition of 1, 2, 3 or more nucleotides in a strand of a DNA double helix.

DNA Deletion: A DNA deletion mutation is the deletion or removal of 1, 2, 3 or more nucleotides in a strand of a DNA double helix.

Frameshift Mutations: Frameshift mutations are DNA insertions or DNA deletions which effect the translation of the DNA sequence to the encoded amino acid sequence because of the insertion or deletion of particular nucleotides.

DNA Mismatches: A DNA mismatch can include an insertion or a deletion but also refers to a DNA sequence with incorrect base pairing resulting from an error during replication. The normal base pairings are A-T and C-G. Examples of mismatches include A-C, A-G, A-A, T-C, T-G, T-T, C-C, and G-G where "A" represents adenine, "G" represents guanine, "C" represents cytosine and "T" represents thymidine.

Damaged DNA: The individual nucleotides of a DNA sequence can be altered in their chemistry or sequence thus resulting in damaged DNA. By this definition (from "DNA Repair and Mutageneis" by E. C. Friedberg, G. C. Walker and W. Siede, ASM Press, Washington, D.C. 1995, which is hereby incorporated by reference), all the other definitions provided here fall under DNA damage which can be subclassified into spontaneous damage or environmentally induced damage. Examples of DNA damage include: mismatches, tautomeric shifts, deaminated bases, uracil incorporated DNA, lost bases also known as depurinated or depyrimidinated DNA, oxidatively and radically induced damaged DNA, ionization (UV) induced damaged DNA, and chemically induced damaged DNA (induced by alkylating agents, cross linking agents, psoralens, metabolites such as heterocyclic amines, N-2-acetyl-2-aminofluorene, benzopyrene, aflatoxins, N-methyl-N'-nitro-N-nitrosoguanidine, and 4-nitroquinoline-1-oxide).

DNA Mutation Binding Proteins: DNA mutation binding proteins are proteins and peptides capable of detecting DNA mutations and binding to such mutated DNA. Such DNA mutation binding proteins include human MutS homologue2 (hMSH2), xeroderma pigmentosum complementation group A (XPA), xeroderma pigmentosum C (XPC), xeroderma pigmentosum complementation group E (XPE), *Thermus thermophilus* Mut S (TthMutS), thymine DNA glycosylase (TDG), *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase (MutY), *Escherechia coli* Uvr ABC and functional domains or active fractions thereof.

Chimeric Proteins: A chimeric protein is a fusion or linkage of two or more different peptides. Generally, the linked peptides are joined or linked by a linker peptide. Chimeric proteins generally have all or a substantial portion of a first polypeptide linked at the amino(N-) or carboxy (C-) terminus to all or a portion of a second polypeptide. The term "chimeric protein" as used herein refers to a C-terminal to N-terminal fusion of a first protein and a second protein where one of the proteins is generally a DNA mutation binding protein and the other protein is generally a nuclease. The fusion proteins of the present invention include constructs in which the C-terminal portion of the first protein is fused to the N-terminal portion of the second, and also constructs in which the C-terminal portion of the second protein is fused to the N-terminal portion of the first. In the invention, the DNA mutation binding proteins and the nucleases can be placed at either the N-terminus or the C-terminus of the chimeric protein.

Chimeric cDNA: Chimeric cDNA refers to the cDNA encoding the chimeric proteins of the invention.

Linker Peptide: Linker peptides are short peptides which link two peptides in a chimeric protein. Linker peptides generally have random coil structures. Linker peptides are designed to maintain the activity of the two linked peptides. In particular, the linker peptide of this invention is designed so as not to interrupt the normal fold of the nuclease or the DNA binding domains DNA damage binding protein of the proteins forming the chimera. Linker peptides can consist of any amino acid in a variety of combinations of various lengths. A preferred linker consists of eight amino acids rich in glycine and proline. Glycine and proline residues are utilized because they are known to disrupt protein secondary structure. Disruption of protein secondary structure in a chimera serves to keep the proteins active while maintaining the peptides at a short distance from each other. This separation of the two peptides helps ensure correct folding of the individual proteins as well as the retention of native function.

Nucleases: Nucleases are proteins and peptides capable of cleaving or cutting DNA. Nucleases include the N-terminus of human excision repair cross-complementing rodent repair deficiency (XPF), *Serratia marcescens* nuclease (Nuc), *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Escherechia coli* Uvr ABC and other DNA nucleases.

Recombinant: Recombinant means to be produced by recombinant DNA technology.

Hybrid DNA Molecule: A hybrid DNA molecule is a double stranded DNA molecule which includes one DNA strand from a first DNA molecule and a second, complementary DNA strand from a second DNA molecule. The first and second DNA molecules may come from the same source or from different sources.

PCR Product: A PCR product is a polynucleotide molecule produced by a polymerase chain reaction (PCR). PCR procedures are well known in the art and exemplified in *Current Protocols in Molecular Biology,* ed. F. M. Ausubel, et al. Massachusetts General Hospital and Harvard Medical School 1987, which is hereby incorporated by reference.

Flow Cytometry: Flow cytometry is the passage of cells, microspheres or beads, one at a time, through a specific sensing or detection region for analysis of the particular cell, microsphere or bead. Single cells, microspheres or bead are passed through a sensing or detection zone of a flow cytometer which consists of a focused laser light source and a detection system for the measurement of scattered light and electronic properties by means of hydrodynamic focusing. Automatic flow cytometers are well known in the art and the present invention is not limited to the use of any particular flow cytometer.

Detection Agents: Detection agents are chemical moieties which permit detection or identification of an entity. Detection agents may be radioactive, fluorescent, chemilluminescent, etc. Preferred detection agents include streptavidin-phycoerythrin (SA-phycoerythrin) which binds to biotinylated substrates. In addition, green fluorescent protein, and Alexa fluorescent dyes, all of which are detected by fluorescent signal can be used. Furthermore, radioactive labels such as $P^{32}$ and $S^{35}$ often used for gel based assays but also can be used in a solid support assay. Chemiluminescent detection agents such as luciferase can also be used for detection.

Solid Support: A solid support is an entity or device to which DNA is coupled and utilized for DNA mutation or SNP detection. Solid supports which find use in the invention include but are not limited to beads or microspheres for flow cytometry; dip sticks for dip stick DNA analysis technology; glass slides and DNA chips.

Taking into account these definitions, the present invention concerns the use of DNA mutation binding proteins for identifying, detecting and mapping DNA sequence variation, single nucleotide polymorphisms, DNA mutations including DNA mismatches, and damaged DNA. The methods of the invention include the use flow cytometry, dipstick technology, glass slides and DNA chip technologies for detection. The invention has widespread use in identifying and characterizing DNA sequence variation. The present invention has widespread advantages for detection of any of a number of mutations in the genomic DNA of an individual or organism and has the advantages of being both rapid and extremely accurate in effecting the detection of such mutations. The invention has widespread use in mutation detection. The invention finds wide applicability in diagnosis of a number of genetically associated disorders as well in other applications where identification of genetic mutations may be important.

I. DNA Sequence Variation, SNP, DNA Mutation and Disease Detection

The methods of this invention concern the use of DNA mutation binding proteins for identifying, detecting and mapping DNA sequence variations, single nucleotide polymorphisms, DNA mutations including DNA mismatches and damaged DNA. A DNA sequence variation and DNA mutations or mutated DNA are changes in a DNA sequence from a normal or wildtype sequence to a mutated or different sequence. DNA mutations include genetic mutations, single base pair mutations, point mutations, DNA mismatches, DNA insertions, DNA deletions, DNA transversions, DNA transitions, frameshift mutations, damaged DNA, and other changes or alterations in a normal or wild type DNA sequence. DNA mutations can result in disease expression. In some circumstances the genetic sequence variability has no effect host organism. In other circumstances the genetic variability can be lethal.

Single Nucleotide Polymorphisms (SNPs) represent single nucleotide changes in DNA sequences between normal or wildtype sequences and mutant or different DNA sequences. As with DNA mutations, SNPs can result in disease expression. In some circumstances the disease resulting from the SNP is known. In other circumstances, indentification of the SNP is the first step toward identification of the molecular basis for a disease.

Numerous diseases can be detected by the methods of the invention. Such diseases can be mutant sequences resulting in SNPs or they can be caused by other mutations. Exemplary diseases include without limitation, diseases such as cystic fibrosis, generalized myotonia and myotonia congenita, hyperkalemic periodic paralysis, hereditary ovalocytosis, hereditary spherocytosis and glucose malabsorption; which are associated with mutations in the genes encoding ion transporters; multiple endocrine neoplasia, which is associated with mutations in the MEN2a, b, and MEN1 genes; familial medullary thyroid carcinoma, and Hirschsprung's disease, which are associated with mutations in the ret proto-oncogene; familial hypercholesterolemia, which is associated with mutations in the LDL receptor gene; neurofibromatosis and tuberous sclerosis, which are associated with mutations in the NF1 gene, and NF type 2 gene; breast and ovarian cancer, which are associated with mutations in the BRCA1, BRCA2, BRCA3 genes; familial adenomatous polyposis, which is associated with mutations in the APC gene; severe combined immunodeficiency, which is associated with mutations in the adenosine deaminase gene; xeroderma pigmentosum, which is associated with mutations in the XPAC gene; Cockayne's syndrome, which is associated with mutations in the ERCC6 excision repair gene; fragile X, which is associated with mutations in the fmrl gene; Duchenne's muscular dystrophy, which is associated with mutations in the Duchenne muscular dystrophy gene; myotonic dystrophy, which is associated with mutations in the myotonic dystrophy protein kinase gene; bulbar muscular dystrophy, which is associated with mutations in the androgen receptor genes; Huntington's disease, which is associated with mutations in the Huntington's gene; Peutz-jegher's syndrome; Lesch-Nyhan syndrome, which is associated with mutations in the HPRT gene; Tay-Sachs disease, which is associated with mutations in the HEXA gene; congenital adrenal hyperplasia, which is associated with mutations in the steroid 21-hydroxylase gene; primary hypertension, which is associated with mutations in the angiotensin gene; hereditary non-polyposis, which is associated with mutations in the hNMLH1 gene; colorectal carcinoma, which is associated with mutations in the 2 mismatch repair genes; colorectal cancer, which is associated with mutations in the APC gene; forms of Alzheimer's disease which have been associated with the apolipoprotein E gene, retinoblastoma, which is associated with mutations in the Rb gene; Li-Fraumeui syndrome, which is associated with mutations in the p53 gene; various malignancies and diseases that are associated with translocations: e.g., in the bcr/abl, bcl-2 gene; chromosomes 11 to 14 and chromosomes 15 to 17 transpositions.

In addition to human diseases, the present invention provides for techniques for the analysis of DNA mutations and SNPs in any organism. Such organisms include plants, humans, non-human animals and mircrorganisms including bacteria, yeast and algae.

II. DNA Mutation Binding Proteins

DNA mutation binding proteins are proteins and peptides capable of detecting DNA mutations and binding to such mutated DNA. DNA mutation binding proteins find use in the methods of the invention for detecting DNA mutations and SNPs. Such DNA mutation binding proteins may be used alone or in combination with a nuclease in a chimeric protein. In some cases, partial (but fully active) fragments of the full-length protein find use in the invention as explained in more detail below. DNA mutation binding proteins which find use in the invention include but are not limited to the following proteins:

*Thermus thermophilus* Mut S (TthMuts) is a thermostabile (heat stable) protein which functions in mismatch repair. This protein recognizes all mismatches, and, as such finds widespread use in the techniques of the invention. It is useful for mismatch recognition. It is particularly useful in the invention because of its thermostability and ability to recognize all mismatches.

Human Mut S homologue 2 (hMSH-2) and active fractions thereof function in mismatch repair, has ATPase activity and recognizes primarily G-T mismatches. It is useful for DNA mismatch recognition.

Human Xeroderma pigmentosum complementation group A (XPA) and active fractions thereof function in nucleotide excision repair. The protein primarily recognizes UV induced DNA damage. The protein is useful for DNA damage recognition.

Human Xeroderma pigmentosum complementation group C(XPC) and active fractions thereof function in nucleotide excision repair. The protein primarily recognizes UV induced DNA damage and is useful for DNA damage recognition.

*Mehtanococcus thermoautotropicum* thymine DNA glycosylase(TDG) is a thermostabile protein which recognizes T/G mismatches. This protein is particularly useful because of its DNA mismatch recognition and thermostability.

Human Xeroderma pigmentosum complementation group E (XPE) functions in nucleotide excision repair. The protein primarily recognizes UV induced DNA damage and is useful for DNA damage recognition.

*Escherechia coli* Fapy-DNA glycosylase recognizes DNA damage by oxidative injury. *Escherechia coli* endonuclease III recognizes primarily apurinic (abasic) sites. *Escherechia coli* endonuclease IV also recognizes primarily apurinic (abasic) sites. *Escherechia coli* T4 endonuclease recognizes pyrimidine dimers (UV damage). *Escherechia coli* uracil DNA glycosylase recognizes uracil-containing DNA. *Escherechia coli* A/G-specific adenine DNA glycosylase (MutY) recognizes G/A mismatches.

1. Chimeric Proteins

The DNA mutation binding proteins of the invention may be in the form of a chimeric protein. The chimeric proteins generally have sequences presented by the formulae:

A-L-B and B-L-A wherein A is a peptide having DNA mutation binding activity and capable of binding to mutated DNA such as those identified above, B is a peptide having nuclease activity and L is a linker peptide. The chimeric proteins are linked in such a manner as to produce a single protein which retains the biological activity of both A and B.

a. DNA Mutation Binding Proteins (A)

The various DNA mutation binding proteins and active fragments thereof outlined above may be used with the chimeric proteins of the invention. The DNA mutation binding proteins may be located at the N-or the C-terminus of the chimeric peptide. The chimeric peptide may or may not contain a linker peptide separating the DNA mutation binding protein from the nuclease.

b. Nucleases: (B)

Nucleases are proteins capable of cleaving or cutting DNA. Nucleases which find use in the chimeric proteins of the invention include but are not limited to the following proteins:

The N-terminus of XPF functions in nucleotide excision repair in complex with ERCC1 and XPA to repair various forms of DNA damage. The N-terminus of XPF contains an endonuclease function and thus functions in the chimeras to cut DNA. The N-terminus of XPF appears to be nonspecific and can cut both double and single stranded DNA.

*Serratia marcescens* nuclease (Nuc) is a very stable, nonspecific nuclease that serves a protective role in *S. marcescens*. In the chimeras, this nuclease functions to cut DNA.

*Escherechia coli* Fapy-DNA glycosylase (Fpg) functions in the excision of 8-oxoguanine and formamidopyrimidines. This enzyme removes these nucleotides and leaves a gap in the DNA sequence.

*Escherechia coli* endonuclease III is an endonuclease that functions to repair DNA damaged by radiation, oxidation and UV light.

*Escherechia coli* exonuclease III functions to repair abasic sites, and DNA damaged by oxidation and alkylation.

*Escherechia coli* endonuclease IV functions to repair abasic sites, and DNA damaged by oxidation and alkylation.

*Escherechia coli* T4 endonuclease repairs UV damaged DNA by removing the damaged base.

*Escherechia coli* uracil DNA glycosylase removed deaminated cytosine or uracil from DNA.

*Escherechia coli* A/G-specific adenine DNA glycosylase cuts at G/A mismatches and oxidative damage.

*Escherechia coli* TDG cuts at G/T mismatches and deaminated cytosine or uracil.

c. Linker Peptides: (L)

Linker peptides are short peptides with random coil structures used to link two peptides or proteins in the chimeric proteins of the invention. Linker peptides are designed to maintain the activity and native folded structure of the two linked peptides or proteins. In particular, the linker peptides of this invention are designed so as not to interrupt the tertiary structure of the nucleases or the DNA binding domains of the DNA binding proteins. The length of the linker is not critical so long as the peptides retain their activity in the chimera. The linker peptide generally consists of 8 amino acids rich in glycine and proline or other amino acids, known to disrupt protein secondary structure. For example, the sequence GSGPSPGS (SEQ ID NO:17) finds use in the invention. However, in some circumstances the linker peptides will be as short as zero amino acids where the nuclease and DNA binding protein retain activity in the absence of a linker peptide. In other circumstances the peptide will have up to 5, 6, 7, 8 9 10, 11–15, 16–20 or 21–30 amino acids.

2. Polypeptide Variants

In addition to the full-length nuclease and DNA mutation binding protein sequences described above, various functional domains or active fragments for proteins such as XPF, XPA and hMSH-2 have been identified and find use alone and in the chimeric proteins of the invention. These sequences are included in the full-length sequences described therein. Such functional domains include amino acid sequences 637–877 of hMSH2 depicted in SEQ ID NO:1; amino acid sequences 98–219 of XPA depicted in SEQ ID NO: 9; amino acid sequences 12–378 of XPF depicted in SEQ ID NO: 11. These functional domains for the DNA mutation binding proteins and the nucleases can be used in the chimeric proteins of the invention. The functional domains of the DNA mutation binding proteins hMSH2 and XPA also find use with flow cytometry detection without the use of a nuclease with the chimera. Use of functional domains can simplify protein expression and purification since smaller protein domains are generally well defined structurally and are often more stable in vitro than full-length proteins.

The present invention also includes the use of proteins having amino acid sequences similar to those of the native proteins mentioned herein, but into which modifications are naturally provided (e.g., allelic variations in the nucleotide sequence which may result in amino acid changes in the polypeptides) or deliberately engineered modifications. Such modifications in the sequences may include the replacement, insertion or deletion of one or more amino acid residues in the coding sequence. For example, the modified protein may contain one or more additional amino acids at one or both ends of the polypeptide chain; may have an amino acid sequence which differs from that of the naturally-occurring protein; or may be an active fragment of the naturally-occurring protein. The term “substantially identical,” is used herein to encompass such potential modifications, and specifically herein means that a particular subject sequence, for example, a mutant sequence, varies from the native sequence by one or more substitutions, deletions, or additions, the net effect of which is to retain biological activity of the protein when derived as a chimeric fusion protein.

As illustrative modifications of the proteins of this invention, one acidic amino acid, such as aspartic acid, may be substituted for another acidic amino acid such as glutamic acid; or a basic amino acid, such as lysine, arginine or histidine may be substituted for another basic amino acid; or a non-polar amino acid, such as glycine, alanine, leucine or isoleucine may be substituted for another non-polar amino acid.

3. Protein Purification

The DNA mutation binding proteins and the chimeric proteins of the invention are generally purified to some degree prior to use.

a. Isolation of DNA Mutation Binding Proteins

The DNA mutation binding proteins of the invention are generally purified prior to use in the invention. However, there is no requirement that the proteins be completely purified. In many cases, partially purified proteins will work in the invention.

Protein purification techniques are well known to those of skill in the art. These techniques involve, at one level, the crude fractionation of the host cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography (FPLC) or even HPLC.

Various techniques suitable for use in protein purification will be well known to those of skill in the art. These include, for example, precipitation with ammonium sulfate, PEG, antibodies and the like or by heat denaturation, followed by centrifugation; chromatography such as ion exchange, gel filtration, reverse phase, hydroxylapatite and, affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified DNA mutation binding protein or peptide.

b. Isolation of Chimeric Proteins

The chimeric proteins of the invention are produced by recombinant technology. As a first step, a chimeric cDNA is produced by linking two cDNAs by overlap extension PCR methodology as described in Innis, M. A. et al. (1990) *PCR Protocols: A Guide to Methods and Applications*, Academic Press, San Diego, Calif. and as detailed in the Example section below. Four PCR primers are required to produce each chimeric cDNA as detailed in the Examples below In the first PCR reaction, primer 1 amplifies the N-terminal coding region of the first protein while incorporating an Nde I restriction site and primer 2 amplifies the C-terminal coding region of the first protein while incorporating half of the linker. In a second PCR reaction, primer 3 amplifies the N-terminal coding region of the second protein while incorporating the other half of the linker and primer 4 amplifies the C-terminal coding region of the second protein while incorporating a second unique restriction site. A third PCR reaction uses the products of the first two PCR reactions as a template and the end primers 1 and 4 to produce the chimeric PCR product.

The full length chimeric PCR products are digested at unique restriction sites and subcloned into a suitable vector such as the pET28 or pET31 expression vector available from Novagen. Once cloned into a suitable cloning vector, the chimeric protein may be produced in large quantities in a host for the vector. Specific examples of chimeric protein synthesis are illustrated in the Example section below.

In most circumstances, it will be desirable to purify the chimeric proteins or variants thereof. Protein purification techniques are well known to those of skill in the art as discussed above. As is generally known in the art, it is believed that the order of conducting the various purification steps may be changed, or that certain steps may be omitted, and still result in a suitable method for the preparation of a substantially purified chimeric protein or peptide.

In one embodiment, the chimeric proteins of the invention are expressed with an N-terminal His-tag. Expression conditions are optimized for soluble expression of the chimeric protein. Nickel affinity chromatography can be used for purification of the chimeric proteins using the affinity of the His-tag for metal ions.

There is no general requirement that the chimeric protein always be provided in their most purified state. Indeed, it is contemplated that less substantially purified products will have utility in certain embodiments. Partial purification may be accomplished by using fewer purification steps in combination, or by utilizing different forms of the same general purification scheme.

III. DNA Mutation Detection

Various techniques find use in the methods of the invention. The methods of the invention include the use flow cytometry, dipstick technology, glass slides and DNA chip technologies for detection of mutations and SNPs.

1. General Approach

A general approach for detecting a DNA mutation using a solid support in accordance with this invention is as follows. Beads or microspheres for flow cytometry; dip sticks for dip stick DNA analysis technology; glass slides and DNA chips are all collectively referred to herein as solid supports.

Beads or microspheres for use in flow cytometry (5.0 $\mu$m polystyrene microspheres, for example) are available commercially (e.g. Luminex Corp., Austin, Tex.). The surfaces of the commercially available beads can be carboxylated for attachment of DNA. The DNA attached to the carboxylated surface contains a “unilinker” at the 5' end of the DNA molecule. This “unilinker” is a common linker used in attachments of DNA to beads or microspheres in flow cytometry. Such linkers are commercially available from Operon. DNA may be purchased from Operon that already contains the linker.

Dipsticks for DNA analysis may be made by procedures well known in the art. Dipsticks made of plastic, acrylic or other suitable material are carboxylated by procedures well known in the art to produce a carboxylated dip stick surface. DNA is then attached to the carboxylated surface. The DNA attached to the carboxylated surface contains a “unilinker” at the 5' end of the DNA molecule. This “unilinker” is a common linker used in attachments of DNA to beads or microspheres in flow cytometry. Such linkers are commercially available from Operon. DNA may be purchased from Operon that already contains the linker.

Glass slides for DNA analysis may be made by procedures well known in the art. The surfaces of the glass slide are carboxylated by procedures well known in the art to produce carboxylated glass slide surfaces. DNA is then attached to the carboxylated surfaces. The DNA attached to the carboxylated surfaces contains a "unilinker" at the 5' end of the DNA molecule. This "unilinker" is a common linker used in attachments of DNA to beads or microspheres in flow cytometry. Such linkers are commercially available from Operon. DNA may be purchased from companies like Operon that already contains the linker.

DNA chips and their use in DNA analysis are described in U.S. Pat. No. 5,837,832 which is hereby incorporated by reference.

In a first step, DNA samples of interest are coupled to solid supports by techniques known in the art (e.g., carbodiimide coupling, or other means) to produce aliquots of solid supports having DNA coupled thereto. Generally, the solid surface is carboxylated. The DNA may be single or double stranded and will include DNA mutations for detection. Such DNA can be coupled as single stranded DNA or it can be coupled as double stranded DNA and converted to single stranded DNA. The DNA will include a unilinker attached to the 5' end to faciliate coupling. Such unilinkers are available commercially from Operon.

DNA mutations are detected using DNA mutation binding proteins. The DNA mutation binding proteins are generally coupled to a detection agent such as biotin. The DNA mutation binding protein/detection agent is incubated with the DNA coupled to the solid support. A preferred detection agent is biotin/streptavidin-phycoerythrin. The biotinylated DNA mutation binding protein binds to the mutated DNA and the detection agent bound to the mutation binding protein is detected after addition of the streptavidin-phycoerythrin which binds strongly to biotin and yields a detectable fluorescent signal.

In another format of the invention, the DNA mutation binding protein may be in the form of a chimeric protein. The chimeric proteins of the invention have sequences presented by the formulae A-L-B and B-L-A where A is a peptide having DNA mutation binding activity and capable of binding to mutated DNA, B is a peptide having nuclease activity and L is a linker peptide.

When the chimeric protein is utilized the mutation analysis, the detection agent such as biotin is coupled to the DNA on the solid support rather than to the mutation binding protein. The chimeric protein is incubated with the support coupled DNA, the DNA mutation binding protein binds to mutated DNA and the nuclease activity of the chimera cleaves the DNA from the support thereby removing the detection agent. The solid supports are analyzed for the presence and the absence of the detection agents. DNA sequences containing mutated DNA are identified with the chimeras by those supports without a detectable detection agent.

2. Detection of Mutations Using Flow Cytometry

The speed and accuracy of flow cytometry makes it an ideal analytical tool for use in the methods of the invention.

Flow cytometry systems are available commercially, e.g., Luminex Inc., Austin Tex. The microspheres are encoded with differing amounts of fluorescent dyes allowing detection of up to 100 different beads to which different forms of DNA are attached. The 100 beads are read simultaneously with the flow cytometer.

DNA may be coupled to flow cytometry beads by procedures well known in the art as detailed in the Example section below. Briefly, beads are incubated with the coupling agent, EDC [1-Ethyl-3-(3-Dimethylaminopropyl) carbodiimide Hydrocholride] (available from Pierce). The treated beads are washed with mild detergent such as Tween 20 and SDS. The beads are then incubated with a suitable annealing buffer for the coupling or annealing of the DNA.

Flow cytometry beads can be analyzed individually or in multiplex fashion (more than one bead per assay). Flow cytometry assays may be conducted with DNA mutation binding proteins alone or with chimeric proteins. Depending on whether the DNA is labeled or the DNA binding protein is labeled, different assay buffers are utilized as detailed in the Example section below.

Generally, wild type DNA is coupled to the beads and the sample DNA is annealed later for analysis. However, in some circumstances, the sample DNA may be coupled to the beads and the wild type (WT) DNA is annealed for the analysis. The DNA may be single stranded or it may be double stranded and converted to single stranded for hybridization.

DNA is labeled when the chimeric proteins are utilized for mutation detection. Biotin labeled DNA may be purchased from Operon. Alternatively, biotin labeled DNA can be prepared by procedures well known in the art. However, obtaining pre-labeled DNA is preferred because labeling after the fact can introduce label on the bases themselves rather than at one end of the DNA. The labeled single strand DNA is coupled to the beads.

Once the DNA has been coupled to the beads, the complimentary strand is then annealed (this is generally test sample such as a patient's DNA sample that has been amplified by PCR) as detailed in the Example section.

After coupling and annealing of the DNA samples, the DNA mutation binding protein is added.

Where the DNA mutation binding protein is used directly for analysis (in the absence of the chimera), the DNA mutation-binding protein is labeled rather than the DNA. DNA mutation binding proteins may be labeled with labels such a biotin as detailed in the Example section below. The streptavidin-phycoerythrin then binds to biotin to give the detection signal. Other suitable protein labels include green fluorescent protein and Alexa dyes which can be detected directly.

When the chimeric proteins are utilized the DNA bound to the bead is labeled with a label such as biotin. The chimeric proteins are incubated with the beads and a decrease in signal is monitored by flow cytometry. A decrease in signal indicates that the DNA mutation binding protein has bound to the mutation and the nuclease has cleaved the DNA thereby removing the signal. Where the DNA mutation binding protein is utilized alone, the DNA mutation-binding protein is labeled and incubated with the beads. Where the DNA mutation binding protein recognizes a mutation, the protein would bind to the DNA on a bead and an increase in signal would be detected by flow cytometry.

Thus if the DNA mutation binding protein recognizes damage or mismatch on the bead, reporter fluorescence is detected on that specific bead. Alternatively, the DNA can be biotinylated and if the chimera preferentially cleaves damage or mismatches then the beads containing those DNAs are not detected (the beads themselves are detected but the fluorescent signal on the beads is not detected—so one can detect both negative and positive signal) because the biotin to which the reporter would bind has been removed. However, any DNA that is not cleaved (undamaged DNA) is detected by the fluorescent reporter.

3. Detection of Disease Causing Mutations

Specific mutations leading to diseases can be detected using the techniques of this invention. Wild type DNA sequences are compared to a sample of interest to determine if the sample of interest contains a known DNA mutation. A DNA sample, e.g. from a patient, is amplified by PCR using specific primers flanking the gene sequence of interest with the potential mutation. A library of wild type DNA is obtained. Such wild type DNA can be purchased from a commercial source such as Operon, Alameda, Calif. This library contains sequences for the wild type DNA sequences of the gene of interest. For example, to test for known BRCA1 mutations, one uses a single strand of BRCA1 DNA from the library of approximately 200 bases where the suspected mutation site is centered in those 200 bases. This strand contains wild type sequence so one can check for the mutations in a patient sample by the formation of a mismatch between the wildtype sequence and the sample sequence. Any known DNA mutation leading to disease including but not limited to those diseases outlined above can be tested.

In an alternative embodiment to test for the mutation is to use DNA of approximately 200 bases where the suspected mutation site is centered in that 200 bases and the strand contains the mutant sequence. In this embodiment, a mismatch with the patient's sample will be formed if the patient does not carry the mutant sequence. Alternatively, if a mismatch were not detected, that would suggest that the patient might carry the disease gene.

Both embodiments can be performed to improve the accuracy of the testing.

The single stranded DNA (either WT or mutant) can either be covalently attached to a bead or to some other solid support such as a dipstick or glass slide or a chip by procedures well known in the art. The DNA may be attached as double stranded DNA and then converted to single stranded through exposure of the double stranded DNA to elevated temperatures or increase stringency buffers. Alternatively, single stranded DNA is used directly.

A PCR amplified patient DNA sample is then annealed to the solid supported wild type and mutant DNA by adding the amplified patient sample to the solid supported DNA, heating to 90° C., and slowly cooling. This allows the patient sample to anneal to the DNA on the solid support.

Next, a biotinylated DNA mutation binding protein such as thermophilic MutS (or thermophilic Muts with some other detectable label) which binds specifically to mismatches is incubated with the annealed DNA. The biotinylated thermophilic MutS binds to the mutated DNA and is detected with streptavidin-phycoerythrin which binds strongly to biotin and yields a detectable fluorescent signal.

If a mismatch is present, thermophilic MutS will bind and a signal will be detected. Negative and positive control are used to validate the method.

The results obtained from these types of experiments are interpreted as follows:

For wild type (WT) DNA on bead or solid support+patient sample, a detectable match indicates that the patient does not have the mutation; a detectable mismatch means the patient does have the mutation.

For mutant DNA on bead or solid support+patient sample, a detectable match means the patient does have the mutation; a mismatch means the patient does not have the mutation.

Most patients with mutations will be heterozygous (i.e., they will carry a normal and mutant copy of that gene). In this case both WT and mutant DNA on bead or solid support will produce a match and a mismatch. This result would mean the patient carries one copy of the mutation and is at risk for the disease tested.

In order to improve the accuracy of the testing, it is important that appropriate control reactions are carried out. Such control reactions include attaching to two different solid supports the 200 base single strand substrate containing WT DNA. On two other solid supports, 200 base single strand substrate containing the mutation is attached. Next, both WT and mutant DNA complimentary strands are annealed to the WT and the mutant DNA on the solid support. The biotinylated DNA mutation binding protein such as MutS preferentially detects the mismatched DNA as evidenced by increased signal for the mismatch substrate.

If the necessary control reactions have worked properly, the following results should be obtained:

1. WT DNA on bead+WT complimentary strand=match (no or very low signal)
2. WT DNA on bead+mutant complimentary strand mismatch (strong signal)
3. mutant DNA on bead+WT complimentary strand=mismatch (strong signal)
4. mutant DNA on bead+mutant complimentary strand=match (no or very low signal)

IV. SNP Analysis

Single Nucleotide Polymorphisms (SNP) can be detected using the techniques of the invention. The SNPs can be known or unknown.

1. Known SNPs

Known SNPs can be identified in test samples using the same procedures outlined above for DNA mutation analysis. Native or wild type DNA is attached to a solid support such as flow cytometry beads. Next, the test DNA sample is isolated. The DNA may be amplified by PCR using oligos that flank the SNP. The DNA sample is incubated with the native or wild type DNA attached to the solid support. Finally, the mixture is incubated with a labeled DNA mutation binding protein. A detected mismatch is indicative of a SNP. The test sample may be isolated from a patient.

In an alternative embodiment, two solid supports are utilized. Native or wild type DNA is coupled to one support. DNA containing the known mutation is coupled to the other support. A DNA sample is incubated with both solid supports under conditions that allows DNA hybridization. Finally, the mixture is incubated with a labeled DNA mutation binding protein. If the sample DNA has a SNP, the native DNA-support will show a mismatch and the mutant DNA-support will show no signal due to the match. If the sample DNA does not have the mutation, the native support will show a match and the mutant support will show a mismatch.

The most efficient solid support for known SNP analysis is flow cytometry. A library of DNA molecules of interest can be coupled to the beads. Such DNA can be produced by PCR. For example, if one is attempting to identify a SNP in a particular gene such as a BRCA breast cancer gene, one would PCR a blood sample from a candidate to amplify the DNA using oligos that flank the region of interest. The PCR sample is then annealed to the beads containing the BRCA native DNA in sections of 100–200 bases with overlap to ensure SNP detection in the entire gene. A DNA mutation binding protein such as thermophilic MutS protein which recognizes all DNA mismatches is labeled with a detectable label such as biotin and is then incubated with the beads. Streptavidin Phycoerythrin can be used as a reporter. If the DNA mutation binding protein (MutS) protein detects a DNA mutation, it binds to the DNA which is bound to the bead forming a DNA mutation binding protein—DNA—bead complex. The biotin attached to the DNA mutation-binding protein (MutS) is detected by the reporter using flow cytometry.

The ability to assay 100 beads (each with a different form of DNA attached) per sample using flow cytometry in a matter of seconds makes the genomic approach to SNP detection feasible. This approach makes it possible to narrow down the SNP to approximately 100 bases which can then be sequenced to identify the exact nature of the SNP or change in the sequence. The DNA sequencing could be done from the initial PCR reaction used to anneal to the beads thus simplifying the SNP detection greatly.

2. Unknown SNPs

The techniques of the invention can be extended to a genome wide search of SNPs. For genome wide search for SNPs, flow cytometry is the preferred form of detection. In one embodiment, a library of beads with wildtype DNA is attached in 200–500 base fragments where each fragment overlaps with the next by ~30 bases to insure that all DNA is read. Preferably, smaller fragments such 200 bases are used since it is estimated that a SNP occurs every 1000 base pairs and it is desirable to narrow down the SNP to limit the amount of sequencing needed. As described above, the patient sample is amplified and annealed to the beads containing WT DNA sequence.

One hundred (100) beads (which can read in mutliplex fashion—at the same time due to the ability to detect each bead by its fluorescent signature) can be read in one test well. Therefore in 96 well format, 9600 sections of 200 bases can be read in less than an hour which correlates with 1,920,000 bases checked for SNPs on each 96 well plate. Mismatches can be detected in minutes thereby reflecting a SNP in the respective 200 base fragment on that bead. If that fragment corresponds to a DNA sequence of interest, further sequencing (from the original PCR sample used to anneal to the beads) will identify the exact SNP sequence.

V. DNA Sequence Variation Detection

DNA sequence variation can be analyzed using the techniques of the invention. Often, differences exist in similar DNA regions isolated from two individuals of a species. Such differences in DNA sequence are known as genetic sequence variation. Genetic sequence variation may result in phenotypic differences in the two individuals or may have no phenotypic effect whatsoever. Similarly, the genetic sequence variation may have a profound effect on the host of the different genetic sequence or it may have no effect whatsoever.

Comparisons between two DNA samples can lead to useful genetic information. For example, with the various genome projects, reference or control sequences are available to use for comparison purposes. New DNA samples isolated from similar or dissimilar organisms can be compared to the known sequences using the techniques of the invention. Similarly, two different unknown samples can be compared. Single nucleotide polymorphisms, DNA mutations, etc. can be identified and analyzed using the techniques of the invention.

A first DNA sample is attached to a solid support such as flow cytometry beads. The first DNA sample may be a known sample or an unknown DNA sample. Next, a test sample of DNA is isolated. The test sample may be a PCR product. The test sample is then incubated with the DNA attached to the solid support under conditions suitable to permit DanA hybridization between the two DNA samples. DNA sequence differences are detected as DNA mismatches or other "mutations" in the hybrid DNA.

The invention having been fully described is now exemplified by the following non-limiting examples.

EXAMPLES

Example 1

DNA Mutation Binding Protein Purification

The TthMutS protein was expressed for pET in BL21 (DE3) cells (available from Novagen). The pET 21 MutS expression construct was transformed into BL21 (DE3) cells for amplification. After plating on selection media, colonies were picked and grown up in 2 liters Luria broth (LB) media+carbamicillin (50 $\mu$g/ml) at 25° C. at 125 rpm overnight. The cultures were induced with 0.3 mM IPTG when the optical density of the cultures reached 0.6–1.0 at 600 nm to induce synthesis of the MutS protein from the cloned cDNA. At induction, the speed of the shaker was increased to 225 rpm. The cultured cells were harvested after 4 hours of growth by centrifugation. The pellets were then frozen at –80° C. The pellets were thawed on ice and resuspended in 200 ml of HepA buffer (20 mM Tris, 0.5 mM DTT, 0.5 mM EDTA, 100 mM NaCl, 10% glycerol, pH 7.5). One ml of 1 mg/ml lysozyme and 2 ml of 20% Triton X-100 were added to the resuspended pellet. The resuspended pellet mixture was left on ice for 30 minutes until the cell suspension became viscous. After the 30 minute period, the suspension was sonicated for 4×30 seconds. The sonicated mixture was then centrifuged for 30 minutes at 11–13K rpm. The pellet was resuspended in HepA buffer+6M urea and rocked overnight at 4° C. to solubilize the proteins.

After the overnight incubation, the solubilized mixture was centrifuged for 30 minutes at 11–1 3K rpm. The supernatant was collected and 200 ml of HepA buffer (pH 7.5) was added to reduce the urea concentration to 3M. The mixture was then filtered and run on a 5 ml heparin column (Pharmacia) on a Pharmacia GradiTrac Protein Purification system at 4° C. Proteins were separated on a 200 ml gradient from 100% HepA/0% HepB (HepA with 1 M NaCl) to 0% HepA/100% HepB. Five milliliter (ml) fractions were collected. Purity was assessed by SDS-PAGE. The purest fractions were pooled and stored frozen at –80° C. for storage.

Example 2

Biotin Labeling of DNA Mutation Binding Protein

Fifty (50) pmol of MutS protein from Example 1 in 200 uL PBS was labeled with biotin by addition of 4 uL of a fresh 1 mg/mL solution of biotin (available from Pierce) in PBS. The reaction was incubated at room temperature for 1 h after which excess biotin was removed by dialysis against PBS for 1 h.

Example 3

Coupling of DNA to Microspheres

Each stock vial of beads was sonicated and vortexed. Two hundred microliters of beads were aliquoted to an eppendorf tube. The tube was spun for 1 minute at 14K and the supernatant was removed. Fifty $\mu$l of 0.1M MES, pH 4.5. was added and the mixture was vortexed. Next, 1 $\mu$l of 1 mM oligo was added and the mixture was vortexed. Next, 2.5 $\mu$l of fresh 10 mg/ml EDC was added. The mixture was vortexed and then allowed to sit in the dark for 30 m at room temperature. 2.5 $\mu$l of fresh 10 mg/ml EDC was then added and the reaction was allowed to sit for an additional 30 minutes. The mixture was centrifuged the supernatant was removed. The beads were washed with 200 $\mu$l 0.02% Tween-20 followed by 200 $\mu$l 0.1% SDS. Next, 200 $\mu$l annealing buffer (10 mM Tris pH 7.4, 200 mM NaCl, 5 mM $MgCl_2$) was added.

Complimentary oligos were annealed to the strand on the bead to produce double-stranded substrate. As examples, a perfect complimentary strand was annealed to a bead to produce a match or double-stranded complimentary DNA, cholesterol containing oligo was annealed to a bead to produce damaged substrate and a mismatch containing oligo was annealed to a bead to produce a mismatched substrate. The beads were then heated to 80° C. in the dark. The reaction was cooled slowly to room temperature to allow the oligos to anneal. The beads were washed once with 200 μl annealing buffer. Next, 200 μl annealing buffer was added. The mixture was then vortexed.

Example 4

Flow Cytometry Analysis

Mutant DNA was analyzed using biotinylated MutS (example 2) and flow cytometry. A 50 base pair substrate containing complimentary DNA (match) was attached to one bead. A 50 base pair substrate containing one mismatch was attached to another bead. The biotinylated MutS preferentially detects the mismatched DNA as evidenced by increased signal for the mismatch substrate.

The LX100 Flow Cytometer instrument is available from from Luminex Corp., Austin, Tex. XY platform on the LX100 allows assays to be analyzed in 96 well format using filter bottom plates from Millipore.

Biotinylated MutS (ranging from 0.1 to 10 pmols) was added to beads coupled with the DNA substrates. (5000 beads are used per reaction. Beads can be analyzed individually or in multiplex fashion, i.e. more than one kind of bead per assay.) The mixture was incubated for 30 min at 37° C. and washed with 200 uL PBST. Next, SA-PE (streptavidin-phycoerytherin fluorescent dye) was added and the reaction was incubated with gentle shaking for 5 min at room temperature in the dark. The reaction mixture was washed with PBST (PBS with 0.02% Tween). Two hundred uL PBST was then added.

The beads are read on the LX100 to determine the change in reporter fluorescence of beads. In the case shown (FIG. 1), DNA is not biotinylated but the MutS protein is biotinylated. Binding buffer is utilized and an increase in reporter fluorescence marks a binding event (detection of mismatch).

For activity or ability to bind to mismatches, binding buffer (50 mM Tris pH 7.5, 50 mM KCl, 10 mM MgCl2, 5 mM DTT, 2 mM ATP,15 mM EDTA) was used. The data is shown in FIG. 1. All data are reported as change in mean fluorescence intensity (MFI). To one bead is attached a 50 base pair substrate containing complimentary DNA (match). To the second beads is attached a 50 base pair substrate containing a mismatch. The MutS protein binds to the mismatched DNA preferentially as evidenced by the increase in signal on the mismatch containing bead.

Example 5

Illustrative of the invention, the following chimeras were isolated and purified.

| Chimera # | Chimera |
|---|---|
| 1 | XPF (fragment)-linker-XPA (fragment) |
| 2 | XPF (fragment)-linker-hMSH2 (fragment) |
| 3 | XPA (fragment)-linker-XPF (fragment) |
| 4 | hMSH2 (fragment)-linker-XPF (fragment) |
| 5 | Nuc (full)-linker-hMSH2 (fragment) |
| 6 | Nuc (full)-linker-XPA (fragment) |
| 7 | MutS (full)-linker-XPF (fragment) |
| 8 | XPF (fragment)-linker-MutS (full) |
| 9 | Nuc (full)-linker-MutS (full) |

-continued

| Chimera # | Chimera |
|---|---|
| 10 | XPA (full)-linker-XPF (fragment) |
| 11 | XPF (fragment)-linker-XPA (full) |
| 12 | Nuc (full)-linker-XPA (full) |

The linker peptides all had the following acid sequence: GSGPSPGS (SEQ ID NO:17).

The chimeric peptides are produced by recombinant technology. As a first step, a chimeric cDNA is produced by linking two cDNAs by overlap PCR extension technology. The primers used to produce the chimeric cDNA's are identified by the region of the peptide encoded by cDNA. For example, chimera #1 includes XPF at the N-terminus of the chimeric peptide and XPA at the C-terminus of the chimeric peptide. In contrast, chimera 3 includes XPA (fragment) at the N-terminus and XPF at the C-terminus of the chimeric peptide.

Example 6

Synthesis of Chimeras 1–6 a) XPF, XPA, hMSH-2 and NucA

The cDNA's for chimeras 1–6 were synthesized in a multistep PCR procedure. As a first step, XPF at the C and N termini, XPA at the C and N termini, hMSH2 at the C and N termini and NucA at the N-terminus were synthesized by PCR.

For the PCR reactions, 100 ng cDNA template was used for each reaction. XPA and XPF were cloned at Lawrence Livermore National Laboratory (LLNL) Livermore, Calif. U.S.A. The XPF cDNA template is available from LLNL. The XPA cDNA template is available from LLNL. The hMSH2 cDNA template is available from Dr. Adrian Whitehouse, St. James University, UK. The nuc cDNA template is available from Dr. Michael Benedik, Baylor College of Medicine, Tex. The PCR reactions contained a pair of primers with 100 pmol of each primer, 100 μM each dNTP, 10 μl 10×buffer (final concentration 20 mM Tris-HCl, 50 mM KCl, 2 mM $MgCl_2$, pH 8.4). One μl of Taq polymerase enzyme was used. The reaction volume was brought to 100 μl with water. The PCR conditions were as follows: 94° C. for 3 minutes; 94° C., 1 min; 50° C., 1 min; and 72° C. for 3 minutes. The cycle was repeated 25 times and the final product stored at 4° C. Gibco Platinum Taq polymerase was utilized. The dNTPs were obtained from Perkin Elmer.

The primer pairs as outlined below were utilized to produce the indicated portion of the cDNA chimera. Each primer pair was utilized in a PCR reaction with the corresponding cDNA as a template. For example, for XPE at the N-terminus, the XPF cDNA template was utilized with primers having sequences depicted as SEQ ID NO:43 and 44 as indicated below to produce the XPF at the N-terminus PCR product.

(1) XPF (fragment) at N-terminus ctc cat atg gcg ccg ctg ctg gag (SEQ ID NO: 43)

act acc agg act agg acc act acc gtt get ttc tag gac cag (SEQ ID NO: 44)

(2) XPF (fragment) at C-terminus ggt agt ggt cct agt cct ggt agt atg gcg ccg ctg ctg gag (SEQ ID NO: 45)

ctc gag ctc tca gtt gct ttc tag gac cag (SEQ ID NO: 46)

(3) XPA (fragment) at N-terminus ctc cat atg gaa ttt gat tat gta ata tgc g (SEQ ID NO: 47)

act acc agg act agg acc act acc aaa ttt ctt ctg ttt cat ttt ttc tcg g (SEQ ID NO: 48)

(4) XPA (fragment) at C-terminus ggt agt ggt cct agt cct ggt agt atg gaa ttt gat tat gta ata tgc g (SEQ ID NO: 49)

ctc gag ctc tca aaa ttt ctt ctg ttt cat ttt ttc tcg g (SEQ ID NO: 50)

(5) hMSH2 (fragment) at N-terminus ctc cat atg tcc agg cat gct tgt gtt g (SEQ ID NO: 51)

act acc agg act agg acc act acc tct ttc cag ata gca ctt c (SEQ ID NO: 52)

(6) hMSH2 (fragment) at C-terminus ggt agt ggt cct agt cct ggt agt tcc agg cat gct tgt gtt g (SEQ ID NO: 53)

ctc gag ctc tca tct ttc cag ata gca ctt c (SEQ ID NO: 54)

(7) Nuc at N-terminus ctc cca tgg gct tta aca aca aga tgt tgg cct tgg ccg cc (SEQ ID NO: 55)

act acc agg act agg acc act acc gtt ttt gca gcc cat caa ctc cgg (SEQ ID NO: 56)

b) Synthesis of Chimeras 1–6

The PCR reaction products from a) above were utilized as template for a second PCR reaction to produce chimeric cDNAs 1–6. These PCR reaction products can be mixed and matched in various combinations in subsequent PCR reactions to produce various cDNA chimeras.

For chimera 1, the PCR reaction products XPF at the N-terminus and XPA at the C-terminus were utilized as template in the second PCR reaction.

For chimera 2, the PCR reaction products XPF at the N-terminus and hMSH2 at the C-terminus were utilized as template in the second PCR reaction.

For chimera 3, the PCR reaction product XPA at the N-terminus and XPF at the C-terminus were utilized as template in the second PCR reaction.

For chimera 4, the PCR reaction product hMSH2 at the N-terminus and XPF at the C-terminus were utilized as template in the second PCR reaction.

For chimera 5, the PCR reaction products Nuc at the N-terminus and hMSH2 at the C-terminus were utilized as template in the second PCR reaction.

For chimera 6, the PCR reaction products Nuc at the N-terminus and XPA at the C-terminus were utilized as template in the second PCR reaction.

Each second PCR reaction contained 100 ng of template as indicated above, 100 pmol of each primer as indicated below, 100 μM each dNTP, 10 μl 10×buffer (final concentration 20 mM Tris-HCl, 50 mM KCl, 2 mM $MgCl_2$, pH 8.4. One μl of Taq polymerase enzyme was used. The reaction volume was brought to 100 μl with water. The PCR conditions were as follows: 94° C. for 3 minutes; 94° C., 1 min; 50° C., 1 min; and 72° C. for 3 minutes. The cycle was repeated 30 times and the final product stored at 4° C. Gibco Platinum Taq polymerase was utilized. The dNTPs were obtained from Perkin Elmer.

The primers for the second PCR reactions were as follows:

(1) Chimera 1: XPF (fragment)-linker-XPA (fragment)

ctc cat atg gcg ccg ctg (SEQ ID NO: 57)

ctc gag ctc tca aaa ttt c (SEQ ID NO: 58)

(2) Chimera 2: XPF (fragment)-linker-hMSH2 (fragment)

ctc cat atg gcg ccg ctg (SEQ ID NO: 59)

ctc gag ctc tea tct ttc (SEQ ID NO: 60)

(3) Chimera 3: XPA fragment-linker-XPF (fragment)

ctc cat atg gaa ttt gat (SEQ ID NO: 61)

ctc gag ctc tca gtt gct (SEQ ID NO: 62)

(4) Chimera 4: hMSH2 (fragment)-linker-XPF (fragment)

ctc cat atg tcc agg cat (SEQ ID NO: 63)

ctc gag ctc tca gtt gct (SEQ ID NO: 64)

(5) Chimera 5: NucA-linker-hMSH2 (fragment)

ctc cca tgg gct tta aca (SEQ ID NO: 65)

ctc gag ctc tca tct ttc (SEQ ID NO: 66)

(6) Chimera 6: NucA-linker-XPA (fragment)

ctc cca tgg gct tta aca (SEQ ID NO: 67)

ctc gag ctc tca aaa ttt c (SEQ ID NO: 68)

Example 7

Synthesis of Chimeras 7–9 a) MutS, XPF (Fragment) and Nuc

The cDNAs for chimeras 7–9 were synthesized in a multistep PCR procedure. As a first step, MutS at the N-terminus, MutS at the C-terminus, XPF domain at the N- and C-termini and Nuc at the N-terminus were synthesized. For the PCR reactions, 100 ng cDNA template was used for each reaction. The MutS cDNA template is available from Dr. Adrian Whitehouse, St. James University, UK. The XPF cDNA template is available from LLNL. The nuc cDNA template is available from Dr. Michael Benedik, Baylor College of Medicine, Tex. Each PCR reaction contained a pair of PCR primers 100 pmol of each primer indicated below, 100 μM each dNTP, 10 μl 10×buffer (final concentration 20 mM Tris-HCl, 50 mM KCl, 2 mM $MgCl_2$, pH 8.4). One μl of Taq polymerase enzyme was used in the reaction. The reaction volume was brought to 100 μl with water. The PCR conditions were as follows: 94° C. for 5 minutes; 94° C., 1 min; 60° C., 1 min; and 72° C. for 1.5 minutes. The cycle was repeated 30 times and the final product stored at 4° C. Gibco Platinum Taq polymerase was utilized. The dNTPs were obtained from Perkin Elmer.

The primer pairs as outlined below were utilized. Each primer pair was utilized in a PCR reaction with the corresponding cDNA as a template. For example, for MutS at the N-terminus, the Mut-S cDNA template was utilized with the primers depicted below having been assigned SEQ ID NO:'s 69 and 70 in a PCR reaction to produce the MutS at the N-terminus PCR product.

(1) MutS at N-terminus ctc cat atg ggg ggg tat ggc gga gtt aag (SEQ ID NO: 69)

act acc agg act agg acc act acc ccc ctt cat gct acc cag ggg gag (SEQ ID NO: 70)

(2) MutS at C-terminus ggt agt ggt cct agt cct ggt agt atg ggg ggg tat ggc gga gtt aag (SEQ ID NO: 71)

ctc gtc gac tca ccc ctt cat gct acc cag ggg (SEQ ID NO: 72)

(3) NucA at N-terminus ctc cat atg cgc ftt aac aac aag atg ttg gcc ttg gcc gcc (SEQ ID NO: 73)

act acc agg act agg acc act acc gtt ttt gca gcc cat caa ctc cgg (SEQ ID NO: 74)

(4) XPF (Fragment) at N-terminus ctc cat atg gcg ccg ctg ctg gag (SEQ ID NO: 75)

ggt agt ggt cct agt cct ggt agt gtt gct ttc tag gac cag (SEQ ID NO: 76)

(5) XPF (Fragment) at C-terminus act acc agg act agg acc act acc atg gcg ccg ctg ctg gag (SEQ ID NO: 77)

ctc gtc gac tca gtt gct ttc tag gac cag (SEQ ID NO: 78)

b) Synthesis of Chimeras 7–9

The PCR reaction products from a) above were utilized as template for a second PCR reaction to produce chimeric cDNAs 7–9. These PCR reaction products can be mixed and matched in various combinations in subsequent PCR reactions to produce various cDNA chimeras.

For chimera 7, the PCR reaction products MutS at the N-terminus and XPF domain at the C-terminus were utilized as template in a second PCR reaction.

For chimera 8, the PCR reaction products XPF domain at the N-terminus and MutS at the C-terminus were utilized as template in a second PCR reaction.

For chimera 9, the PCR reaction products NucA at the N-terminus and MutS at the C-terminus were utilized in a second PCR reaction.

Each second PCR reaction contained 100 ng of template as indicated above and 100 pmol of each primer as indicated below. Each reaction contained 100 $\mu$M for each dNTP from Perkin Elmer, 10 $\mu$l 10×buffer (final concentration 20 mM Tris-HCl, 50 mM KCl, 2 mM $MgCl_2$, pH 8.4). One $\mu$l Taq polymerase was utilized. The reaction volume was brought to 100 $\mu$l with water. The PCR conditions were as follows: 94° C. for 1 minute; 94° C. for 30 seconds, 68° C. for 3 minutes for 30 repetitions. Next, the reaction was run at 68° C. for 3 minutes followed by 15 minutes at 15° C. Finally, the reaction products were stored at 4° C. A Clontech Advantage PCR kit was utilized along with the Klen Taq polymerase.

Chimera 7: MutS-linker-XPF (fragment)
ctc cat atg ggg ggg tat ggc gga gtt aag (SEQ ID NO: 79)
ctc gtc gac tca gtt gct ttc tag gac cag ttc c (SEQ ID NO: 80)
Chimera 8: XPF-linker-MutS (fragment)
ctc cat atg gcg ccg ctg ctg gag tac (SEQ ID NO: 81)
ctc gtc gac tca ccc ctt cat gct acc cag ggg (SEQ ID NO: 82)
Chimera 9: Nuc-linker-MutS
ctc cat atg cgc ttt aac aac aag atg ttg gcc ttg gcc gcc c (SEQ ID NO: 83)
ctc gtc gac tca ccc ctt cat gct acc cag ggg (SEQ ID NO: 84)

Example 8

Synthesis of Chimeras 10–12 a) XPA, Nuc and XPF

The cDNAs for chimeras 1–6 were synthesized in a multistep PCR procedure. As a first step, XPA at the C and N termini, XPF at the C and N termini and NucA at the N-terminus were synthesized.

One hundred (100) ng CDNA template was used for each PCR reaction. XPF was cloned at LLNL and the cDNA is available from LLVL. XPA was cloned at LLNL and the cDNA is available from LLNL. The Nuc cDNA template is available from Dr. Michael Benedik, Baylor College of Medicine, Tex. Each PCR reaction contained 100 pmol of each primer indicated below, 100 $\mu$M each dNTP (from Perkin Elmer) 10 $\mu$l 10×buffer (final concentration 20 mM tris-HCl, 50 mM KCl, 2 mM $MgCl_2$, pH 8.4). One $\mu$l Taq polymerase including 2 mM $MgCl_2$ was utilized. The reaction volume was brought to 100 $\mu$l with water. The PCR reaction conditions were as follows: 94° C. for 3 minutes; 94° C. for 1 minute, 60° C. for 1 minute and 72° C. for 3 minutes repeated 30 times. The reaction products were stored at 4° C. Gibco Platinum Taq Polymerase was utilized.

The following primer pairs were utilized. Each primer pair was utilized in a PCR reaction with the corresponding cDNA as a template. For example, for XPA at the N-terminus, the XPA cDNA template was utilized with the primers depicted below having been assigned SEQ ID NO:'s 85 and 86.

(1) XPA at N-terminus
ctc cat atg gcg gcg gcc gac g (SEQ ID NO: 85)
act acc agg act agg acc act acc gtt cat ggc cac aca tag tac aag (SEQ ID NO: 86)
(2) XPA at C-terminus
ggt agt ggt cct agt cct ggt agt atg gcg gcg gcc gac g (SEQ ID NO: 87)
ctc gag ctc tca gtt cat ggc cac aca tag tac aag (SEQ ID NO: 88)
(3) NucA at N-terminus
ctc cat atg cgc ttt aac aac aag atg ttg gcc ttg gcc gcc (SEQ ID NO: 89)
act acc agg act agg acc act acc gtt ttt gca gcc cat caa ctc cgg (SEQ ID NO: 90)
(4) XPF (fragment) at N-terminus
ctc cat atg gcg ccg ctg ctg gag (SEQ ID NO: 91)
ggt agt ggt cct agt cct ggt agt gtt gct ttc tag gac cag (SEQ ID NO: 92)
(5) XPF (fragment) at C-terminus
act acc agg act agg acc act acc atg gcg ccg ctg ctg gag (SEQ ID NO: 93)
ctc gag ctc tca gtt gct ttc tag gac cag (SEQ ID NO: 94)

b) Synthesis of Chimeras 10–12

The PCR reaction products from a) above were utilized as template for a second PCR reaction to product chimeric cDNAs 10–12. These PCR reaction products can be mixed and matched in various combinations in subsequent PCR reactions to produce various cDNA chimera.

For chimera 10, the PCR reaction products XPA at the N-terminus and XPF at the C-terminus were utilized as template in a second PCR reaction.

For chimera 11, the PCR reaction products XPF at the N-terminus and XPA at the C-terminus were utilized as a template in a second PCR reaction.

For chimera 12, the PCR reaction products XPF at the N-terminus and XPA at the C-terminus were utilized as a template in a second PCR reaction.

Each second PCR reaction contained 100 ng of template as indicated above and 100 pmol of each primer as indicated below. Each reaction contained 100 $\mu$M each dNTP from Perkin Elmer and 10 $\mu$l 10×buffer (final concentration 20 mM Tris-HCl, 50 mM KCl, 2 mM $MgCl_2$ pH 8.4). One $\mu$l Taq polymerase in 2 mM $MgCl_2$ was utilized. The reaction volume was brought to 100 $\mu$l with water.

The PCR reaction conditions were as follows: 94° C. for 1 minute followed by 94° C. for 30 seconds, 68° C. for 3 minutes times 30 cycles. Next, the reaction was heated for 68° C. for 3 minutes followed by 15 minutes at 15° C. The reaction products were stored at 4° C. A Clontech Advantage PCR kit was utilized.

Chimera 10: XPA (full)-linker-XPF (fragment)
ctc cat atg gcg gcg gcc gac g (SEQ ID NO: 95)
ctc gag ctc tca gtt gct ttc tag gac cag ttc c (SEQ ID NO: 96)
Chimera 11: XPF (fragment)-linker-XPA (full)
ctc cat atg gcg ccg ctg ctg gag tac (SEQ ID NO: 97)
ctc gag ctc tca gtt cat ggc cac aca tag tac aag (SEQ ID NO: 98)
Chimera 12: Nuc-linker-XPA (full)
ctc cat atg cgc ttt aac aac aag atg ttg (SEQ ID NO: 99)
ctc gag ctc tca gtt cat ggc cac aca tag tac aag (SEQ ID NO: 100)

Example 9

Chimeric Protein Synthesis

Chimeras 1–4 were cut with Nde I and Sac I for subcloning. Chimeras 5–6 were cut with Nco I and Sac I for subcloning. Chimeras 8–9 were cut with Nde I and Sal I for subcloning. Chimeras 10–12 were cut with Nde I and Sac I for subcloning.

The chimeric cDNAs from Examples 1–4 were purified by gel electrophoresis and cloned into plasmids. Chimeric cDNAs 1–4 and 7–12 were subcloned into pET 28 available from Novagen. Chimeric cDNAs 5–6 were subcloned into pET 31 available from Novagen. The pET 28 and pET 31 chimeric expression constructs were transformed into BL21 (DE3) cells for amplification. After plating on selection media, colonies were picked and grown up in 2 liters Luria broth (LB) media+kanamycin (30 μg/ml) at 25° C. at 125 rpm overnight. The cultures were induced with 0.3 mM IPTG when the optical density of the cultures reached 0.6–1.0 at 600 nm to induce synthesis of the chimeric protein from the cloned cDNA. At induction, the speed of the shaker was increased to 225 rpm. The cultured cells were harvested after 4 hours of growth by contrifugation. The pellets were then frozen at −80° C.

Example 10

Chimeric Protein Purification

The pellets from example 5 were thawed on ice and resuspended in 200 ml of HepA buffer (20 mM Tris, 0.5 mM DTT, 0.5 mM EDTA, 100 mM NaCl, 10% glycerol, pH 7.5). One ml of 1 mg/ml lysozyme and 2 ml of 20% Triton X-100 were added to the resuspended pellet. The resuspended pellet mixture was left on ice for 30 minutes until the cell suspension became viscous. After the 30 minute period, the suspension was sonicated for 4×30 seconds. The sonicated mixture was then centrifuged for 30 minutes at 11–13K rpm. The pellet was resuspended in HepA buffer+6M urea and rocked overnight at 4° C. to solubilize the proteins.

After the overnight incubation, the solubilized mixture was centrifuged for 30 minutes at 11–13K rpm. The supernatant was collected and 200 ml of HepA buffer (pH 7.5) was added to reduce the urea concentration to 3M. The mixture was then filtered and run on a 5 ml heparin column (Pharmacia) on a Pharmacia GradiTrac Protein Purification system at 4° C. Proteins were separated on a 200 ml gradient from 100% HepA/0% hepB (HepA with 1 M NaCl) to 0% HepA/100% HepB. Five ml fractions were collected. Purity was assessed by SDS-PAGE. The purest fractions were pooled and stored frozen at −80° C. for storage.

The approximate molecular weights of the various purified chimeric proteins was as follows:

| Chimera | Approximate Molecular Weight |
|---|---|
| Chi 1 - XPF (fragment)-linker-XPA (fragment) | 54 kDa |
| Chi 2 - XPF (fragment)-linker-hMSH2 (fragment) | 68 kDa |
| Chi 3 - XPA (fragment)-linker-XPF (fragment) | 54 kDa |
| Chi 4 - hMSH2 (fragment)-linker-XPF (fragment) | 68 kDa |
| Chi 5 - Nuc (full)-linker-hMSH2 (fragment) | 57.5 kDa |
| Chi 6 - Nuc (full)-linker-XPA (fragment) | 43.6 kDa |
| Chi 7 - MutS (full)-linker-XPF (fragment) | 130 kDa |
| Chi 8 - XPF (fragment)-linker-MutS (full) | 130 kDa |
| Chi 9 - Nuc (full)-linker-MutS (full) | 120 kDa |
| Chi 10 - XPA (full)-linker-XPF (fragment) | 72 kDa |
| Chi 11 - XPF (fragment)-linker-XPA (full) | 72 kDa |
| Chi 12 - Nuc (full)-linker-XPA (full) | 61 kDa |

Example 11

Further Protein Purification

The chimeric proteins may be further purified, if desired. However, in most instances, the partially purified chimeras work sufficiently well in the invention. Useful purification columns include NTA (nickle affinity columns) Q and SP ion exchange columns, all available from Pharmacia.

For further protein purification, the purest fractions from Example 5 are pooled. Next, 2.5×volumes of water are added to reduce the salt concentration. Next, 1.7×volumes of buffer A for the selected column (as detailed below) are added. The pH of the protein solution is then adjusted appropriately for each column.

The buffers utilized in the purification protocols are outlined below:

Hep A (20 mM Tris, 0.5 mM DTT, 0.5 mM EDTA, 100 mM NaCl, 10% glycerol, pH 7.5)

NTA A (20 mM Tris, 200 mM NaCl, 5 mM BME, 10% glycerol, pH 75)

NTA B (NTA A with 500 mM imidazole)

Q A (20 mM Tris, 1 mM DTT, 100 mM NaCl, 10% glycerol, pH 8.5)

Q B (Q A with 1M NaCl)

SP A (20 mM MES, 1 mM DTT, 100 mM NaCl, 10% glycerol, pH 6.5)

SP B (SP A with 1 M NaCl)

Example 12

Assaying Chimeras for Activity (gel electrophoresis)

In some instances it will be helpful to determine the activity of the chimeras prior to their use in a flow cytometry assay. A standard assay for cleavage of supercoiled plasmid or genomic DNA was used to test purified proteins for endonuclease activity. The plasmid or genomic DNA was either undamaged (as supplied) or damaged for 30 minutes with a UV light source (using a Model UVGL-25 hand held UV lamp, 115 volts, 0.16 amps from UVP, Upland, Calif.).

The reaction mix contained 1 μg DNA in reaction buffer (20 mM Tris-HCl, pH 8.0, 20 mM NaCl, 5 mM $MgCl_2$, 1 mM DTT, 5% glycerol, and 50 μg/mL acetylated bovine serum albumin). Reactions were initiated by the addition of chimeras in the range of 10–200 ng in a total volume of 20 μL. Chimera 6 (Nuc-XPA) and Chimera 4 (MSH-XPF). Following incubation for 2 h at 37° C., SDS was added to a final concentration of 0.5% and incubated for an additional 30 min at 37° C. to disrupt protein-DNA complexes. To visualize digestion products, samples were subjected to electrophoresis on a 1 % agarose gel, stained for several min in 2 μg/mL ethidium bromide and destained in water. As a blank, reaction buffer was added in place of the protein sample.

The results show that the chimeras cleave more UV damaged DNA than undamaged DNA indicating that the DNA mutation binding protein is recognizing and binding to the UV light damaged DNA and the nuclease is cutting that DNA.

Example 13

Flow Cytometry Analysis: Chimeric Proteins and Thermophilic MutS Protein

Chimeric proteins may be used with flow cytometry to analyze DNA mutations. Substrates/Oligos. In order to produce single-stranded, double-stranded and damaged containing substrates 50 mer oligos were purchased from Operon, Alameda, Calif. The oligos can be ordered with or without biotin.

Coupling DNA to Beads. Four different beads were used, one each for single-stranded, double-stranded and damage (cholesterol), or mismatch containing double-stranded substrates.

Each stock vial of beads was sonicated and vortexed. Two hundred microliters of beads were aliquoted to an eppendorf tube. The tube was spun for 1 minute at 14K and the supernatant was removed. Fifty μl of 0.1M MES, pH 4.5. was added and the mixture was vortexed. Next, 1 μl of 1 mM Lum 10 oligo was added and the mixture was vortexed. Next, 2.5 μl of fresh 10 mg/ml EDC was added. The mixture was vortexed and then allowed to sit in the dark for 30 m at room temperature. 2.5 μl of fresh 10 mg/ml EDC was then added and the reaction was allowed to sit for an additional 30 minutes. The mixture was centrifuged the supernatant was removed. The beads were washed with 200 μl 0.02% Tween-20 followed by 200 μl 10.1% SDS. Next,200 μl annealing buffer (10 mM Tris pH 7.4, 200 mM NaCl, 5 mM MgCl2) was added.

Annealing DNA. Complimentary oligos were annealed to produce double-stranded substrate on the beads. A perfect complimentary oligo was annealed to one bead to produce a complimentary double stranded DNA. A cholesterol containing oligo was annealed to a bead to produce a damaged substrate. A mismatch containing oligo was annealed to a bead to produce a mismatched substrate. The remaining bead is left as single stranded DNA. The beads were then heated to 80(C. in the dark. The reaction was cooled slowly to room temperature to allow the oligos to anneal. The beads were washed once with 200 μl annealing buffer. Next, 200 μl annealing buffer was added. The mixture was then vortexed.

Counting Beads. Five μl annealed beads were added to 295 μl PBS (pH 7.6). Beads were counted by reading the events/sec on the LX100 Flow Cytometer for Luminex Inc.

Biotinylation of Proteins. Thermophilic MutS was labled with biotin. 20 pmoles of protein was dialyzed into PBS and brought to 200 uL. Four uL of 1 mg/mL biotin was added and the sample was allowed to incubate for 1 h at 25 C. Excess biotin was dialyzed away in PBS. The sample is stored at 4° C. until assayed.

Assays for Damage Detection using Chimeric Proteins. LX100 Flow Cytometer instrument from Luminex Corp., Austin, Tex. XY platform on the LX100 allows assays to be analyzed in 96 well format using filter bottom plates from Millipore. Chimeric proteins (ranging from 0.1 to 10 pmols) was added to beads coupled with the biotinylated DNA substrates. (5000 beads are used per reaction. Beads can be analyzed individually or in multiplex fashion, i.e. more than one kind of bead per assay.) The mixture was incubated for 30 min at 37° C. and washed with 200 uL PBST. Next, SA-PE (streptavidin-phycoerytherin fluorescent dye) was added and the reaction was incubated with gentle shaking for 5 min at room temperature in the dark. The reaction mixture was washed with PBST (PBS with 0.02% Tween). Two hundred uL PBST was then added.

The beads are read on the LX100 to determine the change in reporter fluorescence of beads. In the case shown (FIG. 2), DNA is biotinylated and the chimera is not, activity buffer is utilized and a decrease in reporter fluorescence marks a cleavage event (detection of damage).

For activity or ability to cut at damage or mismatches, activity buffer (50 mM Tris pH 7.5, 50 mM KCl, 10 mM MgCl2, 5 mM DTT, 2 mM ATP) was used.

Figure 2:
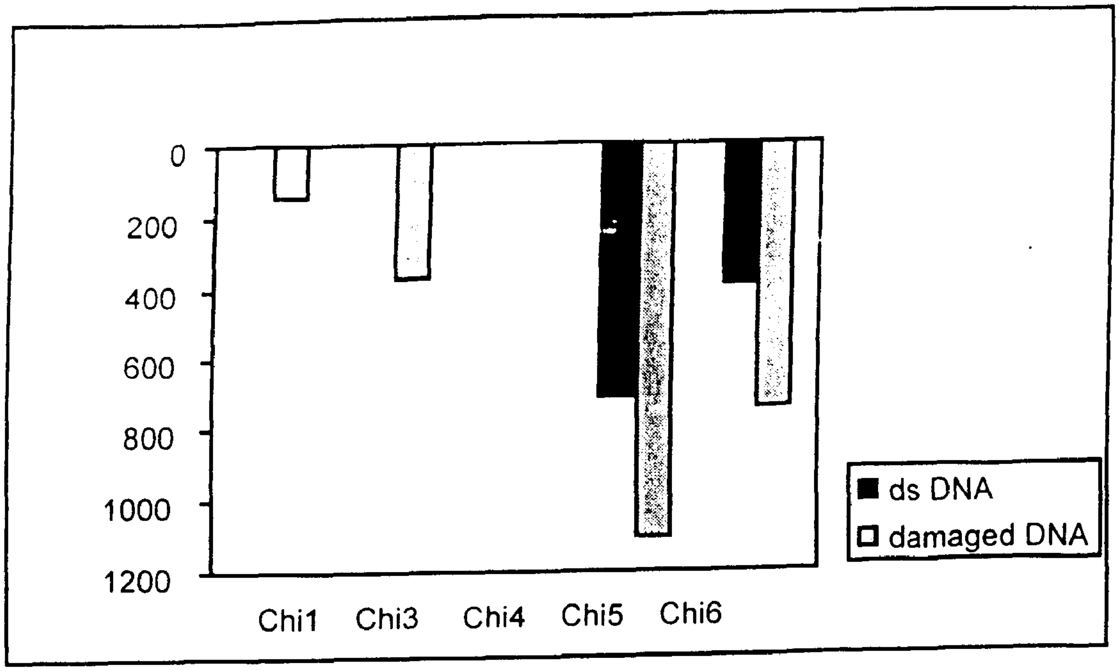
FIG. 2 shows the results of a flow cytometry assay comparing the mean fluorescent intensity detected for damaged and non-damaged DNA using a chimeric protein and biotin labeled DNA for detection.

The data is shown in FIG. 2. All data are reported as change in mean fluorescence intensity (MFI). To one bead is attached a 50 base pair biotinylated substrate containing complimentary DNA (undamaged). To the second beads is attached a 50 base pair biotinylated substrate containing a cholesterol adduct (mimics DNA damage). The DNA mutation binding protein binds to the damaged DNA and the nuclease of the chimera cleaves the damaged DNA as evidenced by decreased DNA binding and loss of signal for the cholesterol containing (damaged) substrate.

What is claimed is:

1. A method for detecting a DNA mutation in a DNA molecule, said method comprising the steps of:

a) obtaining a flow cytometry bead to which said DNA molecule is coupled;

b) forming a mixture by mixing said flow cytometry bead and a labeled DNA mutation binding protein, said labeled DNA mutation binding protein being capable of detecting DNA mutations and binding to such mutated DNA;

c) forming a reacted sample by incubating said mixture under conditions wherein if said DNA molecule includes mutated DNA, said DNA mutation binding protein binds to said mutated DNA; and d) analyzing said reacted sample by detecting the label on the flow cytometry bead to detect the DNA mutation or absence thereof.

2. The method of claim 1 wherein said DNA mutation binding protein is labelled with a chemilluminescent label or a fluorescent label.

3. The method of claim 1 wherein said label is biotin.

4. The method of claim 1 wherein said DNA molecule is a PCR product.

5. The method of claim 1 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

6. The method of claim 1 wherein said DNA mutation binding protein is *Thermus thermophilus* Mut S.

7. The method of claim 6 wherein *Thermus thermophilus* MutS has the amino acid sequence depicted in SEQ ID NO:15.

8. A method for detecting a DNA mutation in a DNA molecule, said method comprising the steps of:

a) obtaining a solid support coupled to said DNA molecule wherein said DNA molecule is labeled;

b) forming a mixture by mixing said solid support and a chimeric protein wherein said chimeric protein includes a labeled DNA mutation binding protein and a nuclease, said labeled DNA mutation binding protein being capable of detecting DNA mutations and binding to such mutated DNA;

c) forming a reacted sample by incubating said mixture under conditions wherein if said DNA molecule includes mutated DNA, said DNA mutation binding protein binds to said mutated DNA and said nuclease cleaves said DNA thereby removing said label from said DNA molecule coupled to said solid support; and d) analyzing said reacted sample by detecting the label or absence thereof on the solid support to detect the DNA mutation.

9. The method of claim 8 wherein said solid support is selected from the group consisting of flow cytometry beads, dip sticks, glass slides and DNA chips.

10. The method of claim 8 wherein said label is a chemilluminescent or a fluorescent label.

11. The method of claim 8 wherein said label is biotin.

12. The method of claim 8 wherein said chimeric protein has the formula A-L-B or B-L-A wherein A is said DNA mutation binding protein, L is a linker and B is said nuclease.

13. The method of claim 8 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

14. The method of claim 8 wherein said nuclease is selected from the group consisting of N-terminus of human excision repair cross-complementing rodent repair deficiency, *Serratia marcescens* nuclease, *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Escherechia coli* Uvr B and *Escherechia coli* Uvr C.

15. The method of claim 13 wherein said DNA mutation binding protein is *Thermus thermophilus* Mut S.

16. The method of claim 15 wherein *Thermus thermophilus* MutS has the amino acid sequence depicted in SEQ ID NO:15.

17. A method for flow cytometric analysis to detect a DNA mutation in a DNA molecule, said method comprising the steps of:

a) obtaining flow cytometry be ads coupled to said DNA molecule;

b) forming a mixture by mixing said beads and a labeled DNA mutation binding protein, said labeled DNA mutation binding protein being capable of detecting DNA mutations and binding to such mutated DNA;

c) forming a reacted sample by incubating said mixture under conditions wherein if said DNA molecule includes mutated DNA, said DNA mutation binding protein binds to said mutated DNA;

d) analyzing said reacted sample by flow cytometry to determine the amount of label on each bead analyzed; and e) detecting the DNA mutation or absence thereof by determining the amount of label on the beads.

18. The method of claim 17 wherein said DNA mutation binding protein is labeled with a fluorescent label or a chemilluminescent label.

19. The method of claim 17 wherein said label is biotin.

20. The method of claim 17 wherein said DNA molecule is a PCR product.

21. The method of claim 17 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

22. The method of claim 21 wherein said DNA mutation binding protein is *Thermus thermophilus* Mut S.

23. The method of claim 22 wherein *Thermus thermophilus* MutS has the amino acid sequence depicted in SEQ ID NO:15.

24. The method of claim 21 wherein human MutS homologue2 has the amino acid sequence depicted in SEQ ID NO:1.

25. The method of claim 21 wherein human MutS homologue2 has the amino acid sequence depicted in SEQ ID NO:3.

26. The method of claim 21 wherein xeroderma pigmentosum complementation group A has the amino acid sequence depicted in SEQ ID NO:7.

27. The method of claim 21 wherein xeroderma pigmentosum complementation group A has the amino acid sequence depicted in SEQ ID NO:9.

28. The method of claim 21 wherein xeroderma pigmentosum complementation group C has the amino acid sequence depicted in SEQ ID NO:19.

29. The method of claim 21 wherein xeroderma pigmentosum complementation group E has the amino acid sequence depicted in SEQ ID NO:21.

30. The method of claim 21 wherein *Escherechia coli* Fpapy DNA glycosylase has the amino acid sequence depicted in SEQ ID NO:23.

31. The method of claim 21 wherein *Escherechia coli* endonuclease III has the amino acid sequence depicted in SEQ ID NO:25.

32. The method of claim 21 wherein *Escherechia coli* exonuclease III has the amino acid sequence depicted in SEQ ID NO:29.

33. The method of claim 21 wherein *Escherechia coli* endonuclease IV has the amino acid sequence depicted in SEQ ID NO:31.

34. The method of claim 21 where T4 endonuclease has the amino acid sequence depicted in SEQ ID NO:39.

35. The method of claim 21 wherein *Escherechia coli* uracil DNA glycosylase has the amino acid sequence depicted in SEQ ID NO:35.

36. The method of claim 21 wherein *Escherechia coli* A/G-specific adenine DNA glycosylase has the amino acid sequence depicted in SEQ ID NO:37.

37. The method of claim 21 wherein *Escherechia coli* Uvr A has the amino acid sequence depicted in SEQ ID NO:101.

38. A method of d etecting a DNA mutation, comprising a) obtaining a DNA molecule;

b) coupling said DNA molecule to a flow cytometry bead to form a DNA-bead complex;

c) forming a mixture by mixing said DNA-bead complex with a labeled DNA mutation binding protein;

d) forming a reacted sample by incubating said mixture under conditions wherein if said DNA molecule includes a mutated DNA, said DNA mutation binding protein binds to said mutated DNA;

e) analyzing said reacted sample by flow cytometry to determine the amount of label on each bead analyzed; and f) detecting the DNA mutation or absence thereof by determining the amount of label on each bead.

39. The method of claim 38 wherein said DNA mutation binding protein is labeled with a fluorescent label or a chemilluminescent label.

40. The method of claim 38 wherein said DNA mutation binding protein is labeled with biotin.

41. The method of claim 38 wherein said DNA molecule is a PCR product.

42. The method of claim 38 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

43. The method of claim 42 wherein said DNA mutation binding protein is *Thermus thermophilus* Mut S.

44. The method of claim 43 wherein *Thermus thermophilus* MutS has the amino acid sequence depicted in SEQ ID NO:15.

45. A method of detecting a DNA mutation, comprising:

a) obtaining a DNA molecule;

b) attaching a label to said DNA molecule to form a labeled DNA molecule;

c) coupling said labeled DNA molecule to a flow cytometry bead to form a labeled DNA-bead complex;

d) forming a mixture by mixing said labeled DNA-bead complex with a chimeric protein wherein said chimeric protein includes a DNA mutation binding protein and a nuclease;

e) forming a reacted sample by incubating said mixture under conditions wherein if said DNA molecule includes mutated DNA said DNA mutation binding protein binds to said mutated DNA and said nuclease cleaves said labeled DNA from said bead;

f) analyzing said reacted sample by flow cytometry to determine the amount of label on each bead analyzed; and g) detecting the DNA mutation or absence thereof by determining the amount of label on the beads.

46. The method of claim 45 wherein said chimeric protein has the formula A-L-B or B-L-A wherein A is said DNA mutation binding protein, L is a linker and B is said nuclease.

47. The method of claim 45 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A and *Escherechia coli* Uvr B.

48. The method of claim 45 wherein said DNA mutation binding protein is *Thermus thermophilus* Mut S.

49. The method of claim 48 wherein *Thermus thermophilus* MutS has the amino acid sequence depicted in SEQ ID NO:15.

50. The method of claim 46 wherein said nuclease is selected from the group consisting of N-terminus of human excision repair cross-complementing rodent repair deficiency, *Serratia marcescens* nuclease, *Escherechia coli* Fpapy-DNA glycosylase; *Escherechia coli* endonuclease III; *Escherechia coli* endonuclease IV; T4 endonuclease; *Escherechia coli* uracil DNA glycosylase; *Escherechia coli* A/G-specific adenine DNA glycosylase, *Escherechia coli* Uvr B and *Escherechia coli* Uvr C.

51. The method of claim 45 wherein said label is biotin.

52. A method for detecting a DNA mutation in a DNA molecule, said method comprising the steps of:

a) obtaining a first DNA molecule;

b) coupling said first DNA molecule to a flow cytometry bead to form a DNA-bead complex;

c) obtaining a second DNA molecule;

d) forming a first mixture by mixing said second DNA molecule with said DNA-bead complex;

e) incubating said first mixture under conditions such that said second DNA molecule hybridizes to said first DNA molecule thereby forming a hybrid, double stranded DNA molecule coupled to said bead wherein said hybrid, double stranded DNA molecule includes one DNA strand from said first DNA molecule and one strand from said second DNA molecule;

f) obtaining a labeled DNA mutation binding protein, said labeled DNA mutation binding protein being capable of detecting DNA mutations and binding to such mutated DNA;

g) forming a second mixture by mixing said labeled DNA mutation binding protein with said hybrid, double stranded DNA molecule coupled to said bead;

h) forming a reacted sample by incubating said second mixture under conditions wherein if said hybrid, double stranded DNA molecule includes mutated DNA, said labeled DNA mutation binding protein binds to said mutated DNA and forms a labeled, hybrid, double stranded DNA-bead complex; and i) analyzing the reacted sample to detect the label or absence thereof on said hybrid, double stranded DNA-bead complex to thereby identify the DNA mutation.

53. The method of claim 52 wherein said DNA mutation is a DNA mismatch.

54. The method of claim 52 wherein said first DNA molecule is wild type DNA and said second DNA molecule is isolated from a host.

55. The method of claim 54 wherein said host is selected from the group consisting of humans, non-human animals, plants and microorganisms.

56. The method of claim 55 wherein said host is a human.

57. The method of claim 52 wherein said first DNA molecule is DNA isolated from a host and said second DNA molecule is wild type DNA.

58. The method of claim 57 wherein said host is selected from the group consisting of humans, non human animals, plants and microorganisms.

59. The method of claim 58 wherein said host is a human.

60. The method of claim 52 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A, *Escherechia coli* Uvr B and active fractions thereof.

61. The method of claim 60 wherein said DNA mutation binding protein is human MutS homologue2 or *Thermus thermophilus* Mut S.

62. The method of claim 61 wherein human MutS homologue2 has the amino acid sequence depicted in SEQ ID NO:1.

63. The method of claim 61 wherein human MutS homologue2 has the amino acid sequence depicted in SEQ ID NO:3.

64. The method of claim 61 wherein *Thermus thermophilus* MutS has the amino acid sequence depicted in SEQ ID NO:15.

65. The method of claim 52 wherein said label is a fluorescent label or a chemilluminescent label.

66. The method of claim 52 wherein said DNA mutation is a single nucleotide polymorphism in said first DNA molecule.

67. The method of claim 52 wherein said DNA mutation is a single nucleotide polymorphism in said second DNA molecule.

68. The method of claim 52 wherein said first DNA molecule and said second DNA molecule are single stranded.

69. The method of claim 52 wherein said label is biotin.

70. A method for detecting a single nucleotide polymorphism in a DNA molecule, said method comprising the steps of:

a) obtaining a first DNA molecule;

b) coupling said first DNA molecule to a flow cytometry bead to form a DNA bead complex;

c) obtaining a second DNA molecule;

d) forming a first mixture by mixing said second DNA molecule with said DNA-bead complex;

e) incubating said first mixture under conditions such that said second DNA molecule hybridizes to said first DNA molecule thereby forming a hybrid, double stranded DNA molecule coupled to said bead wherein said hybrid, double stranded DNA molecule includes one DNA strand from said first DNA molecule and one strand from said second DNA molecule;

f) obtaining a labeled DNA mutation binding protein, said labeled DNA mutation binding protein being capable of detecting DNA mutations and binding to such mutated DNA;

g) forming a second mixture by mixing said labeled DNA mutation binding protein with said hybrid, double stranded DNA molecule coupled to said bead;

h) forming a reacted sample by incubating said second mixture under conditions wherein if said hybrid, double stranded DNA molecule includes mutated DNA, said labeled DNA mutation binding protein binds to said mutated DNA and forms a labeled, hybrid, double stranded DNA-bead complex; and i) analyzing the reacted sample to detect the label or absence thereof on said hybrid, double stranded DNA-bead complex to thereby identify the single nucleotide polymorphism.

71. The method of claim 70 wherein said first DNA molecule is wild type DNA and said second DNA molecule is isolated from a host.

72. The method of claim 71 wherein said host is selected from the group consisting of humans, non-human animals, plants and microorganisms.

73. The method of claim 72 wherein said host is a human.

74. The method of claim 70 wherein said first DNA molecule is DNA isolated from a host and said second DNA molecule is wild type DNA.

75. The method of claim 74 wherein said host is selected from the group consisting of humans, non human animals, plants plants and microorganisms.

76. The method of claim 75 wherein said host is a human.

77. The method of claim 70 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, Escherechia Coli Uvr A, *Escherechia coli* Uvr B and active fractions thereof.

78. The method of claim 77 wherein said DNA mutation binding protein is human MutS homologue2 or *Thermus thermophilus* Mut S.

79. The method of claim 78 wherein human MutS homologue2 has the amino acid sequence depicted in SEQ ID NO:1.

80. The method of claim 78 wherein human MutS homologue2 has the amino acid sequence depicted in SEQ ID NO:3.

81. The method of claim 78 wherein *Thermus thermophilus* MutS has the amino acid sequence depicted in SEQ ID NO:15.

82. The method of claim 70 wherein said label is a fluorescent label or a chemilluminescent label.

83. The method of claim 70 wherein said first DNA molecule and said second DNA molecule are single stranded.

84. The method of claim 70 wherein said label is biotin.

85. A method for detecting a DNA sequence variation between two DNA molecules, said method comprising the steps of:

a) obtaining a first DNA molecule;

b) coupling said first DNA molecule to a flow cytometry bead to form a DNA-bead complex;

c) obtaining a second DNA molecule;

d) forming a first mixture by mixing said second DNA molecule with said DNA-bead complex;

e) incubating said first mixture under conditions such that said second DNA molecule hybridizes to said first DNA molecule thereby forming a hybrid, double stranded DNA molecule coupled to said bead wherein said hybrid, double stranded DNA molecule includes one DNA strand from said first DNA molecule and one strand from said second DNA molecule;

f) obtaining a labeled DNA mutation binding protein, said labeled DNA mutation binding protein being capable of detecting DNA mutations and binding to such mutated DNA;

g) forming a second mixture by mixing said labeled DNA mutation binding protein with said hybrid, double stranded DNA molecule coupled to said bead;

h) forming a reacted sample by incubating said second mixture under conditions wherein if said hybrid, double stranded DNA molecule includes mutated DNA, said labeled DNA mutation binding protein binds to said mutated DNA and forms a labeled, hybrid, double stranded DNA-bead complex; and i) analyzing the reacted sample to detect the label or absence thereof on said hybrid, double stranded DNA-bead complex to thereby identify the DNA sequence variation.

86. The method of claim 85 wherein said first DNA molecule is wild type DNA and said second DNA molecule is isolated from a host.

87. The method of claim 86 wherein said host is selected from the group consisting of humans, non-human animals, plants and microorganisms.

88. The method of claim 87 wherein said host is a human.

89. The method of claim 85 wherein said first DNA molecule is DNA isolated from a host and said second DNA molecule is wild type DNA.

90. The method of claim 88 wherein the DNA sequence variation is a single nucleotide polymorphism.

91. The method of claim 89 wherein said host is a human.

92. The method of claim 85 wherein said DNA mutation binding protein is selected from the group consisting of human MutS homologue2, xeroderma pigmentosum complementation group A, xeroderma pigmentosum complementation group C, xeroderma pigmentosum complementation group E, *Thermus thermophilus* Mut S, thymine DNA glycosylase, *Escherechia coli* Fpapy-DNA glycosylase, *Escherechia coli* endonuclease III, *Escherechia coli* exonuclease III, *Escherechia coli* endonuclease IV, T4 endonuclease, *Escherechia coli* uracil DNA glycosylase, *Escherechia coli* A/G-specific adenine DNA glycosylase, *Escherechia coli* Uvr A, *Escherechia coli* Uvr B and active fractions thereof.

93. The method of claim 92 wherein said DNA mutation binding protein is human MutS homologue2 or *Thermus thermophilus* Mut S.

94. The method of claim 93 wherein human MutS homologue2 has the amino acid sequence depicted in SEQ ID NO:1.

95. The method of claim 93 wherein human MutS homologue2 has the amino acid sequence depicted in SEQ ID NO:3.

96. The method of claim 93 wherein *Thermus thermophilus* MutS has the amino acid sequence depicted in SEQ ID NO:15.

97. The method of claim 85 wherein said label is a fluorescent label or a chemilluminescent label.

98. The method of claim 85 wherein said first DNA molecule is single stranded.

99. The method of claim 85 wherein said second DNA molecule is single stranded.

100. The method of claim 85 wherein said label is biotin.

* * * * *

SEQUENCE LISTING

```
<160> NUMBER OF SEQ ID NOS:  106

<210> SEQ ID NO 1
<211> LENGTH: 240
<212> TYPE: PRT
<213> ORGANISM: Homo sapiens

<400> SEQUENCE: 1

Ser Arg His Ala Cys Val Glu Val Gln Asp Glu Ile Ala Phe Ile Pro
  1               5                  10                  15

Asn Asp Val Tyr Phe Glu Lys Asp Lys Gln Met Phe His Ile Ile Thr
             20                  25                  30

Gly Pro Asn Met Gly Gly Lys Ser Thr Tyr Ile Arg Gln Thr Gly Val
         35                  40                  45

Ile Val Leu Met Ala Gln Ile Gly Cys Phe Val Pro Cys Glu Ser Ala
     50                  55                  60

Glu Val Ser Ile Val Asp Cys Ile Leu Ala Arg Val Gly Ala Gly Asp
 65                  70                  75                  80

Ser Gln Leu Lys Gly Val Ser Thr Phe Met Ala Glu Met Leu Glu Thr
                 85                  90                  95

Ala Ser Ile Leu Arg Ser Ala Thr Lys Asp Ser Leu Ile Ile Ile Asp
            100                 105                 110
```

-continued

```
Glu Leu Gly Arg Gly Thr Ser Thr Tyr Asp Gly Phe Gly Leu Ala Trp
        115                 120                 125

Ala Ile Ser Glu Tyr Ile Ala Thr Lys Ile Gly Ala Phe Cys Met Phe
    130                 135                 140

Ala Thr His Phe His Glu Leu Thr Ala Leu Ala Asn Gln Ile Pro Thr
145                 150                 155                 160

Val Asn Asn Leu His Val Thr Ala Leu Thr Thr Glu Glu Thr Leu Thr
                165                 170                 175

Met Leu Tyr Gln Val Lys Lys Gly Val Cys Asp Gln Ser Phe Gly Ile
            180                 185                 190

His Val Ala Glu Leu Ala Asn Phe Pro Lys His Val Ile Glu Cys Ala
        195                 200                 205

Lys Gln Lys Ala Leu Glu Leu Glu Glu Phe Gln Tyr Ile Gly Glu Ser
    210                 215                 220

Gln Gly Tyr Asp Ile Met Glu Pro Ala Ala Lys Lys Cys Tyr Leu Glu
225                 230                 235                 240


<210> SEQ ID NO 2
<211> LENGTH: 723
<212> TYPE: DNA
<213> ORGANISM: Homo sapiens

<400> SEQUENCE: 2

tccaggcatg cttgtgttga agttcaagat gaaattgcat ttattcctaa tgacgtatac     60

tttgaaaaag ataaacagat gttccacatc attactggcc ccaatatggg aggtaaatca    120

acatatattc gacaaactgg ggtgatagta ctcatggccc aaattgggtg ttttgtgcca    180

tgtgagtcag cagaagtgtc cattgtggac tgcatcttag cccgagtagg ggctggtgac    240

agtcaattga aaggagtctc cacgttcatg gctgaaatgt tggaaactgc ttctatcctc    300

aggtctgcaa ccaaagattc attaataatc atagatgaat tgggaagagg aacttctacc    360

tacgatggat ttgggttagc atgggctata tcagaataca ttgcaacaaa gattggtgct    420

ttttgcatgt ttgcaaccca ttttcatgaa cttactgcct tggccaatca gataccaact    480

gttaataatc tacatgtcac agcactcacc actgaagaga ccttaactat gctttatcag    540

gtgaagaaag gtgtctgtga tcaaagtttt gggattcatg ttgcagagct tgctaatttc    600

cctaagcatg taatagagtg tgctaaacag aaagccctgg aacttgagga gtttcagtat    660

attggagaat cgcaaggata tgatatcatg gaaccagcag caaagaagtg ctatctggaa    720

aga                                                                  723


<210> SEQ ID NO 3
<211> LENGTH: 934
<212> TYPE: PRT
<213> ORGANISM: Homo sapiens

<400> SEQUENCE: 3

Met Ala Val Gln Pro Lys Glu Thr Leu Gln Leu Glu Ser Ala Ala Glu
  1               5                  10                  15

Val Gly Phe Val Arg Phe Phe Gln Gly Met Pro Glu Lys Pro Thr Thr
             20                  25                  30

Thr Val Arg Leu Phe Asp Arg Gly Asp Phe Tyr Thr Ala His Gly Glu
         35                  40                  45

Asp Ala Leu Leu Ala Ala Arg Glu Val Phe Lys Thr Gln Gly Val Ile
     50                  55                  60

Lys Tyr Met Gly Pro Ala Gly Ala Lys Asn Leu Gln Ser Val Val Leu
```

-continued

```
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
        355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495
```

-continued

```
Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
        515                 520                 525

Glu Glu Lys Val Leu Arg Asn Asn Lys Asn Phe Ser Thr Val Asp Ile
    530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
        595                 600                 605

Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
        675                 680                 685

Ala Gln Ile Gly Cys Phe Val Pro Cys Glu Ser Ala Glu Val Ser Ile
    690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
        755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910
```

-continued

```
Ala Glu Val Ile Ala Lys Asn Asn Ser Phe Val Asn Glu Ile Ile Ser
        915                 920                 925

Arg Ile Lys Val Thr Thr
    930


<210> SEQ ID NO 4
<211> LENGTH: 2805
<212> TYPE: DNA
<213> ORGANISM: Homo sapiens

<400> SEQUENCE: 4

atggcggtgc agccgaagga gacgctgcag ttggagagcg cggccgaggt cggcttcgtg      60

cgcttctttc agggcatgcc ggagaagccg accaccacag tgcgcctttt cgaccggggc     120

gacttctata cggcgcacgg cgaggacgcg ctgctggccg cccgggaggt gttcaagacc     180

cagggggtga tcaagtacat ggggccggca ggagcaaaga atctgcagag tgttgtgctt     240

agtaaaatga attttgaatc ttttgtaaaa gatcttcttc tggttcgtca gtatagagtt     300

gaagtttata agaatagagc tggaaataag gcatccaagg agaatgattg gtatttggca     360

tataaggctt ctcctggcaa tctctctcag tttgaagaca ttctctttgg taacaatgat     420

atgtcagctt ccattggtgt tgtgggtgtt aaaatgtccg cagttgatgg ccagagacag     480

gttggagttg ggtatgtgga ttccatacag aggaaactag gactgtgtga attccctgat     540

aatgatcagt tctccaatct tgaggctctc ctcatccaga ttggaccaaa ggaatgtgtt     600

ttacccggag gagagactgc tggagacatg gggaaactga gacagataat tcaaagagga     660

ggaattctga tcacagaaag aaaaaaagct gacttttcca caaaagacat ttatcaggac     720

ctcaaccggt tgttgaaagg caaaaaggga gagcagatga atagtgctgt attgccagaa     780

atggagaatc aggttgcagt ttcatcactg tctgcggtaa tcaagttttt agaactctta     840

tcagatgatt ccaactttgg acagtttgaa ctgactactt ttgacttcag ccagtatatg     900

aaattggata ttgcagcagt cagagccctt aacctttttc agggttctgt tgaagatacc     960

actggctctc agtctctggc tgccttgctg aataagtgta aaacccctca aggacaaaga    1020

cttgttaacc agtggattaa gcagcctctc atggataaga acagaataga ggagagattg    1080

aatttagtgg aagcttttgt agaagatgca gaattgaggc agactttaca agaagattta    1140

cttcgtcgat tcccagatct taaccgactt gccaagaagt ttcaaagaca agcagcaaac    1200

ttacaagatt gttaccgact ctatcagggt ataaatcaac tacctaatgt tatacaggct    1260

ctggaaaaac atgaaggaaa acaccagaaa ttattgttgg cagtttttgt gactcctctt    1320

actgatcttc gttctgactt ctccaagttt caggaaatga tagaaacaac tttagatatg    1380

gatcaggtgg aaaaccatga attccttgta aaaccttcat ttgatcctaa tctcagtgaa    1440

ttaagagaaa taatgaatga cttggaaaag aagatgcagt caacattaat aagtgcagcc    1500

agagatcttg gcttggaccc tggcaaacag attaaactgg attccagtgc acagtttgga    1560

tattactttc gtgtaacctg taaggaagaa aaagtccttc gtaacaataa aaactttagt    1620

actgtagata tccagaagaa tggtgttaaa tttaccaaca gcaaattgac ttctttaaat    1680

gaagagtata ccaaaaataa aacagaatat gaagaagccc aggatgccat tgttaaagaa    1740

attgtcaata tttcttcagg ctatgtagaa ccaatgcaga cactcaatga tgtgttagct    1800

cagctagatg ctgttgtcag ctttgctcac gtgtcaaatg gagcacctgt tccatatgta    1860

cgaccagcca ttttggagaa aggacaagga agaattatat taaaagcatc caggcatgct    1920

tgtgttgaag ttcaagatga aattgcattt attcctaatg acgtatactt tgaaaaagat    1980
```

-continued

```
aaacagatgt tccacatcat tactggcccc aatatgggag gtaaatcaac atatattcga   2040

caaactgggg tgatagtact catggcccaa attgggtgtt ttgtgccatg tgagtcagca   2100

gaagtgtcca ttgtggactg catcttagcc cgagtagggg ctggtgacag tcaattgaaa   2160

ggagtctcca cgttcatggc tgaaatgttg gaaactgctt ctatcctcag gtctgcaacc   2220

aaagattcat taataatcat agatgaattg ggaagaggaa cttctaccta cgatggattt   2280

gggttagcat gggctatatc agaatacatt gcaacaaaga ttggtgcttt ttgcatgttt   2340

gcaacccatt ttcatgaact tactgccttg gccaatcaga taccaactgt taataatcta   2400

catgtcacag cactcaccac tgaagagacc ttaactatgc tttatcaggt gaagaaaggt   2460

gtctgtgatc aaagttttgg gattcatgtt gcagagcttg ctaatttccc taagcatgta   2520

atagagtgtg ctaaacagaa agccctggaa cttgaggagt ttcagtatat tggagaatcg   2580

caaggatatg atatcatgga accagcagca aagaagtgct atctggaaag agagcaaggt   2640

gaaaaaatta ttcaggagtt cctgtccaag gtgaaacaaa tgccctttac tgaaatgtca   2700

gaagaaaaca tcacaataaa gttaaaacag ctaaaagctg aagtaatagc aaagaataat   2760

agctttgtaa atgaaatcat ttcacgaata aaagttacta cgtga                     2805
```

<210> SEQ ID NO 5
<211> LENGTH: 266
<212> TYPE: PRT
<213> ORGANISM: Serratia marcescens

<400> SEQUENCE: 5

```
Met Arg Phe Asn Asn Lys Met Leu Ala Leu Ala Ala Leu Leu Phe Ala
  1               5                  10                  15

Ala Gln Ala Ser Ala Asp Thr Leu Glu Ser Ile Asp Asn Cys Ala Val
             20                  25                  30

Gly Cys Pro Thr Gly Gly Ser Ser Asn Val Ser Ile Val Arg His Ala
         35                  40                  45

Tyr Thr Leu Asn Asn Asn Ser Thr Thr Lys Phe Ala Asn Trp Val Ala
     50                  55                  60

Tyr His Ile Thr Lys Asp Thr Pro Ala Ser Gly Lys Thr Arg Asn Trp
 65                  70                  75                  80

Lys Thr Asp Pro Ala Leu Asn Pro Ala Asp Thr Leu Ala Pro Ala Asp
                 85                  90                  95

Tyr Thr Gly Ala Asn Ala Ala Leu Lys Val Asp Arg Gly His Gln Ala
            100                 105                 110

Pro Leu Ala Ser Leu Ala Gly Val Ser Asp Trp Glu Ser Leu Asn Tyr
        115                 120                 125

Leu Ser Asn Ile Thr Pro Gln Lys Ser Asp Leu Asn Gln Gly Ala Trp
    130                 135                 140

Ala Arg Leu Glu Asp Gln Glu Arg Lys Leu Ile Asp Arg Ala Asp Ile
145                 150                 155                 160

Ser Ser Val Tyr Thr Val Thr Gly Pro Leu Tyr Glu Arg Asp Met Gly
                165                 170                 175

Lys Leu Pro Gly Thr Gln Lys Ala His Thr Ile Pro Ser Ala Tyr Trp
            180                 185                 190

Lys Val Ile Phe Ile Asn Asn Ser Pro Ala Val Asn His Tyr Ala Ala
        195                 200                 205

Phe Leu Phe Asp Gln Asn Thr Pro Lys Gly Ala Asp Phe Cys Gln Phe
    210                 215                 220
```

-continued

```
Arg Val Thr Val Asp Glu Ile Glu Lys Arg Thr Gly Leu Ile Ile Trp
225                 230                 235                 240

Ala Gly Leu Pro Asp Asp Val Gln Ala Ser Leu Lys Ser Lys Pro Gly
                245                 250                 255

Val Leu Pro Glu Leu Met Gly Cys Lys Asn
            260                 265


<210> SEQ ID NO 6
<211> LENGTH: 801
<212> TYPE: DNA
<213> ORGANISM: Serratia marcescens

<400> SEQUENCE: 6

atgcgcttta acaacaagat gttggccttg gccgccctgc tgttcgccgc gcaggcgtcg     60

gccgacacgc tcgaatccat cgacaactgc gcggtcggct gcccgaccgg cggcagcagc    120

aacgtgtcta tcgtgcgcca tgcttatacg ttgaacaaca acagcaccac caagttcgcc    180

aactgggtgg cctatcacat caccaaagac acgccggcca gcggcaagac gcgcaactgg    240

aaaaccgatc cggctctcaa tccggcggac actctggcgc ccgccgatta caccggtgcc    300

aacgccgcgc tgaaggtcga tcgcggtcat caggcgccgc tggcctcgct ggcgggcgtt    360

tccgactggg aatcgttgaa ctacctgtcc aacatcacgc cgcaaaagtc cgatctgaac    420

cagggcgcct gggctcggct ggaagatcag gaacgcaagc tgatcgatcg cgccgatatc    480

tcctcggtct ataccgtgac cgggccgctg tatgagcgcg atatgggcaa actgccgggc    540

acccagaaag cgcacaccat ccccagcgcc tactggaagg taattttcat caacaacagc    600

ccggcggtga accactatgc cgccttcctg ttcgaccaga acacgccgaa gggcgccgat    660

ttctgccaat tccgcgtgac ggtggacgag atcgagaaac gcaccggcct gatcatctgg    720

gccggtctgc cggacgacgt gcaggcttcg ctgaagagca aaccgggcgt tctgccggag    780

ttgatgggct gcaaaaactg a                                              801


<210> SEQ ID NO 7
<211> LENGTH: 273
<212> TYPE: PRT
<213> ORGANISM: Homo sapiens

<400> SEQUENCE: 7

Met Ala Ala Ala Asp Gly Ala Leu Pro Glu Ala Ala Ala Leu Glu Gln
  1               5                  10                  15

Pro Ala Glu Leu Pro Ala Ser Val Arg Ala Ser Ile Glu Arg Lys Arg
             20                  25                  30

Gln Arg Ala Leu Met Leu Arg Gln Ala Arg Leu Ala Ala Arg Pro Tyr
         35                  40                  45

Ser Ala Thr Ala Ala Ala Ala Thr Gly Gly Met Ala Asn Val Lys Ala
     50                  55                  60

Ala Pro Lys Ile Ile Asp Thr Gly Gly Gly Phe Ile Leu Glu Glu Glu
 65                  70                  75                  80

Glu Glu Glu Glu Gln Lys Ile Gly Lys Val Val His Gln Pro Gly Pro
                 85                  90                  95

Val Met Glu Phe Asp Tyr Val Ile Cys Glu Glu Cys Gly Lys Glu Phe
            100                 105                 110

Met Asp Ser Tyr Leu Met Asn His Phe Asp Leu Pro Thr Cys Asp Asn
        115                 120                 125

Cys Arg Asp Ala Asp Asp Lys His Lys Leu Ile Thr Lys Thr Glu Ala
    130                 135                 140
```

-continued

```
Lys Gln Glu Tyr Leu Leu Lys Asp Cys Asp Leu Glu Lys Arg Glu Pro
145                 150                 155                 160

Pro Leu Lys Phe Ile Val Lys Lys Asn Pro His His Ser Gln Trp Gly
                165                 170                 175

Asp Met Lys Leu Tyr Leu Lys Leu Gln Ile Val Lys Arg Ser Leu Glu
            180                 185                 190

Val Trp Gly Ser Gln Glu Ala Leu Glu Glu Ala Lys Glu Val Arg Gln
        195                 200                 205

Glu Asn Arg Glu Lys Met Lys Gln Lys Lys Phe Asp Lys Lys Val Lys
    210                 215                 220

Glu Leu Arg Arg Ala Val Arg Ser Ser Val Trp Lys Arg Glu Thr Ile
225                 230                 235                 240

Val His Gln His Glu Tyr Gly Pro Glu Glu Asn Leu Glu Asp Asp Met
                245                 250                 255

Tyr Arg Lys Thr Cys Thr Met Cys Gly His Glu Leu Thr Tyr Glu Lys
            260                 265                 270

Met
```

<210> SEQ ID NO 8
<211> LENGTH: 822
<212> TYPE: DNA
<213> ORGANISM: Homo sapiens

<400> SEQUENCE: 8

```
atggcggcgg ccgacggggc tttgccggag gcggcggctt tagagcaacc cgcggagctg      60

cctgcctcgg tgcgggcgag tatcgagcgg aagcggcagc gggcactgat gctgcgccag     120

gcccggctgg ctgcccggcc ctactcggcg acggcggctg cggctactgg aggcatggct     180

aatgtaaaag cagccccaaa gataattgac acaggaggag gcttcatttt agaagaggaa     240

gaagaagaag aacagaaaat tggaaaagtt gttcatcaac caggacctgt tatggaattt     300

gattatgtaa tatgcgaaga atgtgggaaa gaatttatgg attcttatct tatgaaccac     360

tttgatttgc caacttgtga taactgcaga gatgctgatg ataaacacaa gcttataacc     420

aaaacagagg caaaacaaga atatcttctg aaagactgtg atttagaaaa aagagagcca     480

cctcttaaat ttattgtgaa gaagaatcca catcattcac aatggggtga tatgaaactc     540

tacttaaagt tacagattgt gaagaggtct cttgaagttt ggggtagtca agaagcatta     600

gaagaagcaa aggaagtccg acaggaaaac cgagaaaaaa tgaaacagaa gaaatttgat     660

aaaaaagtaa aagaattgcg gcgagcagta agaagcagcg tgtggaaaag ggagacgatt     720

gttcatcaac atgagtatgg accagaagaa aacctagaag atgacatgta ccgtaagact     780

tgtactatgt gtggccatga actgacatat gaaaaaatgt ga                        822
```

<210> SEQ ID NO 9
<211> LENGTH: 122
<212> TYPE: PRT
<213> ORGANISM: Homo sapiens

<400> SEQUENCE: 9

```
Met Glu Phe Asp Tyr Val Ile Cys Glu Glu Cys Gly Lys Glu Phe Met
  1               5                  10                  15

Asp Ser Tyr Leu Met Asn His Phe Asp Leu Pro Thr Cys Asp Asn Cys
             20                  25                  30

Arg Asp Ala Asp Asp Lys His Lys Leu Ile Thr Lys Thr Glu Ala Lys
         35                  40                  45
```

-continued

```
Gln Glu Tyr Leu Leu Lys Asp Cys Asp Leu Glu Lys Arg Glu Pro Pro
     50                  55                  60

Leu Lys Phe Ile Val Lys Lys Asn Pro His His Ser Gln Trp Gly Asp
 65                  70                  75                  80

Met Lys Leu Tyr Leu Lys Leu Gln Ile Val Lys Arg Ser Leu Glu Val
                 85                  90                  95

Trp Gly Ser Gln Glu Ala Leu Glu Glu Ala Lys Glu Val Arg Gln Glu
            100                 105                 110

Asn Arg Glu Lys Met Lys Gln Lys Lys Phe
        115                 120
```

<210> SEQ ID NO 10
<211> LENGTH: 366
<212> TYPE: DNA
<213> ORGANISM: Homo sapiens

<400> SEQUENCE: 10

```
atggaatttg attatgtaat atgcgaagaa tgtgggaaag aatttatgga ttcttatctt     60

atgaaccact ttgatttgcc aacttgtgat aactgcagag atgctgatga taaacacaag    120

cttataacca aaacagaggc aaaacaagaa tatcttctga aagactgtga tttagaaaaa    180

agagagccac ctcttaaatt tattgtgaag aagaatccac atcattcaca atggggtgat    240

atgaaactct acttaaagtt acagattgtg aagaggtctc ttgaagtttg ggtagtcaa    300

gaagcattag aagaagcaaa ggaagtccga caggaaaacc gagaaaaaat gaaacagaag    360

aaattt                                                               366
```

<210> SEQ ID NO 11
<211> LENGTH: 367
<212> TYPE: PRT
<213> ORGANISM: Homo sapiens

<400> SEQUENCE: 11

```
Met Ala Pro Leu Leu Glu Tyr Glu Arg Gln Leu Val Leu Glu Leu Leu
  1               5                  10                  15

Asp Thr Asp Gly Leu Val Val Cys Ala Arg Gly Leu Gly Ala Asp Arg
             20                  25                  30

Leu Leu Tyr His Phe Leu Gln Leu His Cys His Pro Ala Cys Leu Val
         35                  40                  45

Leu Val Leu Asn Thr Gln Pro Ala Glu Glu Glu Tyr Phe Ile Asn Gln
     50                  55                  60

Leu Lys Ile Glu Gly Val Glu His Leu Pro Arg Arg Val Thr Asn Glu
 65                  70                  75                  80

Ile Thr Ser Asn Ser Arg Tyr Glu Val Tyr Thr Gln Gly Gly Val Ile
                 85                  90                  95

Phe Ala Thr Ser Arg Ile Leu Val Val Asp Phe Leu Thr Asp Arg Ile
            100                 105                 110

Pro Ser Asp Leu Ile Thr Gly Ile Leu Val Tyr Arg Ala His Arg Ile
        115                 120                 125

Ile Glu Ser Cys Gln Glu Ala Phe Ile Leu Arg Leu Phe Arg Gln Lys
    130                 135                 140

Asn Lys Arg Gly Phe Ile Lys Ala Phe Thr Asp Asn Ala Val Ala Phe
145                 150                 155                 160

Asp Thr Gly Phe Cys His Val Glu Arg Val Met Arg Asn Leu Phe Val
                165                 170                 175
```

-continued

```
Arg Lys Leu Tyr Leu Trp Pro Arg Phe His Val Ala Val Asn Ser Phe
            180                 185                 190

Leu Glu Gln His Lys Pro Glu Val Val Glu Ile His Val Ser Met Thr
        195                 200                 205

Pro Thr Met Leu Ala Ile Gln Thr Ala Ile Leu Asp Ile Leu Asn Ala
    210                 215                 220

Cys Leu Lys Glu Leu Lys Cys His Asn Pro Ser Leu Glu Val Glu Asp
225                 230                 235                 240

Leu Ser Leu Glu Asn Ala Ile Gly Lys Pro Phe Asp Lys Thr Ile Arg
                245                 250                 255

His Tyr Leu Asp Pro Leu Trp His Gln Leu Gly Ala Lys Thr Lys Ser
            260                 265                 270

Leu Val Gln Asp Leu Lys Ile Leu Arg Thr Leu Leu Gln Tyr Leu Ser
        275                 280                 285

Gln Tyr Asp Cys Val Thr Phe Leu Asn Leu Leu Glu Ser Leu Arg Ala
    290                 295                 300

Thr Glu Lys Ala Phe Gly Gln Asn Ser Gly Trp Leu Phe Leu Asp Ser
305                 310                 315                 320

Ser Thr Ser Met Phe Ile Asn Ala Arg Ala Arg Val Tyr His Leu Pro
                325                 330                 335

Asp Ala Lys Met Ser Lys Lys Glu Lys Ile Ser Glu Lys Met Glu Ile
            340                 345                 350

Lys Glu Gly Glu Glu Thr Lys Lys Glu Leu Val Leu Glu Ser Asn
        355                 360                 365


<210> SEQ ID NO 12
<211> LENGTH: 1101
<212> TYPE: DNA
<213> ORGANISM: Homo sapiens

<400> SEQUENCE: 12

atggcgccgc tgctggagta cgagcgacag ctggtgctgg aactgctcga cactgacggg     60

ctagtagtgt gcgcccgcgg gctcggcgcg gaccggctcc tctaccactt tctccagctg    120

cactgccacc cagcctgcct ggtgctggtg ctcaacacgc agccggccga ggaggagtat    180

tttatcaatc agctgaagat agaaggagtt gaacacctcc ctcgccgtgt aacaaatgaa    240

atcacaagca acagtcgcta tgaagtttac acacaaggtg gtgttatatt tgcgacaagt    300

aggatacttg tggttgactt cttgactgat agaatacctt cagatttaat tactggcatc    360

ttggtgtata gagcccacag aataatcgag tcttgtcaag aagcattcat cttgcgcctc    420

tttcgccaga aaaacaaacg tggttttatt aaagctttca cagacaatgc tgttgccttt    480

gatactggtt tttgtcatgt ggaaagagtg atgagaaatc tttttgtgag gaaactgtat    540

ctgtggccaa ggttccatgt agcagtaaac tcatttttag aacagcacaa acctgaagtt    600

gtagaaatcc atgtttctat gacacctacc atgcttgcta tacagactgc tatactggac    660

attttaaatg catgtctaaa ggaactaaaa tgccataacc catcgcttga agtggaagat    720

ttatctttag aaaatgctat tggaaaacct tttgacaaga caatccgcca ttatctggat    780

cctttgtggc accagcttgg agccaagact aaatccttag ttcaggattt gaagatatta    840

cgaactttgc tgcagtatct ctctcagtat gattgtgtca catttcttaa tcttctggaa    900

tctctgagag caacggaaaa agcttttggt cagaattcag gttggctgtt tcttgactcc    960

agcacctcga tgtttataaa tgctcgagca agggtttatc atcttccaga tgccaaaatg   1020

agtaaaaaag aaaaaatatc tgaaaaaatg gaaattaaag aaggggaaga aacaaaaaag   1080
```

-continued gaactggtcc tagaaagcaa c 1101

<210> SEQ ID NO 13
<211> LENGTH: 906
<212> TYPE: PRT
<213> ORGANISM: Homo sapiens

<400> SEQUENCE: 13

Met Ala Pro Leu Leu Glu Tyr Glu Arg Gln Leu Val Leu Glu Leu Leu
1 5 10 15

Asp Thr Asp Gly Leu Val Val Cys Ala Arg Gly Leu Gly Ala Asp Arg
20 25 30

Leu Leu Tyr His Phe Leu Gln Leu His Cys His Pro Ala Cys Leu Val
35 40 45

Leu Val Leu Asn Thr Gln Pro Ala Glu Glu Glu Tyr Phe Ile Asn Gln
50 55 60

Leu Lys Ile Glu Gly Val Glu His Leu Pro Arg Arg Val Thr Asn Glu
65 70 75 80

Ile Thr Ser Asn Ser Arg Tyr Glu Val Tyr Thr Gln Gly Gly Val Ile
85 90 95

Phe Ala Thr Ser Arg Ile Leu Val Val Asp Phe Leu Thr Asp Arg Ile
100 105 110

Pro Ser Asp Leu Ile Thr Gly Ile Leu Val Tyr Arg Ala His Arg Ile
115 120 125

Ile Glu Ser Cys Gln Glu Ala Phe Ile Leu Arg Leu Phe Arg Gln Lys
130 135 140

Asn Lys Arg Gly Phe Ile Lys Ala Phe Thr Asp Asn Ala Val Ala Phe
145 150 155 160

Asp Thr Gly Phe Cys His Val Glu Arg Val Met Arg Asn Leu Phe Val
165 170 175

Arg Lys Leu Tyr Leu Trp Pro Arg Phe His Val Ala Val Asn Ser Phe
180 185 190

Leu Glu Gln His Lys Pro Glu Val Val Glu Ile His Val Ser Met Thr
195 200 205

Pro Thr Met Leu Ala Ile Gln Thr Ala Ile Leu Asp Ile Leu Asn Ala
210 215 220

Cys Leu Lys Glu Leu Lys Cys His Asn Pro Ser Leu Glu Val Glu Asp
225 230 235 240

Leu Ser Leu Glu Asn Ala Ile Gly Lys Pro Phe Asp Lys Thr Ile Arg
245 250 255

His Tyr Leu Asp Pro Leu Trp His Gln Leu Gly Ala Lys Thr Lys Ser
260 265 270

Leu Val Gln Asp Leu Lys Ile Leu Arg Thr Leu Leu Gln Tyr Leu Ser
275 280 285

Gln Tyr Asp Cys Val Thr Phe Leu Asn Leu Leu Glu Ser Leu Arg Ala
290 295 300

Thr Glu Lys Ala Phe Gly Gln Asn Ser Gly Trp Leu Phe Leu Asp Ser
305 310 315 320

Ser Thr Ser Met Phe Ile Asn Ala Arg Ala Arg Val Tyr His Leu Pro
325 330 335

Asp Ala Lys Met Ser Lys Lys Glu Lys Ile Ser Glu Lys Met Glu Ile
340 345 350

Lys Glu Gly Glu Glu Thr Lys Lys Glu Leu Val Leu Glu Ser Asn Pro
355 360 365

-continued

```
Lys Trp Glu Ala Leu Thr Glu Val Leu Lys Glu Ile Glu Ala Glu Asn
    370                 375                 380

Lys Glu Ser Glu Ala Leu Gly Gly Pro Gly Gln Val Leu Ile Cys Ala
385                 390                 395                 400

Ser Asp Asp Arg Thr Cys Ser Gln Leu Arg Asp Tyr Ile Thr Leu Gly
                405                 410                 415

Ala Glu Ala Phe Leu Leu Arg Leu Tyr Arg Lys Thr Phe Glu Lys Asp
            420                 425                 430

Ser Lys Ala Glu Glu Val Trp Met Lys Phe Arg Lys Glu Asp Ser Ser
        435                 440                 445

Lys Arg Ile Arg Lys Ser His Lys Arg Pro Lys Asp Pro Gln Asn Lys
    450                 455                 460

Glu Arg Ala Ser Thr Lys Glu Arg Thr Leu Lys Lys Lys Lys Arg Lys
465                 470                 475                 480

Leu Thr Leu Thr Gln Met Val Gly Lys Pro Glu Glu Leu Glu Glu Glu
                485                 490                 495

Gly Asp Val Glu Glu Gly Tyr Arg Arg Glu Ile Ser Ser Ser Pro Glu
            500                 505                 510

Ser Cys Pro Glu Glu Ile Lys His Glu Glu Phe Asp Val Asn Leu Ser
        515                 520                 525

Ser Asp Ala Ala Phe Gly Ile Leu Lys Glu Pro Leu Thr Ile Ile His
    530                 535                 540

Pro Leu Leu Gly Cys Ser Asp Pro Tyr Ala Leu Thr Arg Val Leu His
545                 550                 555                 560

Glu Val Glu Pro Arg Tyr Val Val Leu Tyr Asp Ala Glu Leu Thr Phe
                565                 570                 575

Val Arg Gln Leu Glu Ile Tyr Arg Ala Ser Arg Pro Gly Lys Pro Leu
            580                 585                 590

Arg Val Tyr Phe Leu Ile Tyr Gly Gly Ser Thr Glu Glu Gln Arg Tyr
        595                 600                 605

Leu Thr Ala Leu Arg Lys Glu Lys Glu Ala Phe Glu Lys Leu Ile Arg
    610                 615                 620

Glu Lys Ala Ser Met Val Val Pro Glu Glu Arg Glu Gly Arg Asp Glu
625                 630                 635                 640

Thr Asn Leu Asp Leu Val Arg Gly Thr Ala Ser Ala Asp Val Ser Thr
                645                 650                 655

Asp Thr Arg Lys Ala Gly Gly Gln Glu Gln Asn Gly Thr Gln Gln Ser
            660                 665                 670

Ile Val Val Asp Met Arg Glu Phe Arg Ser Glu Leu Pro Ser Leu Ile
        675                 680                 685

His Arg Arg Gly Ile Asp Ile Glu Pro Val Thr Leu Glu Val Gly Asp
    690                 695                 700

Tyr Ile Leu Thr Pro Glu Met Cys Val Glu Arg Lys Ser Ile Ser Asp
705                 710                 715                 720

Leu Ile Gly Ser Leu Asn Asn Gly Arg Leu Tyr Ser Gln Cys Ile Ser
                725                 730                 735

Met Ser Arg Tyr Tyr Lys Arg Pro Val Leu Leu Ile Glu Phe Asp Pro
            740                 745                 750

Ser Lys Pro Phe Ser Leu Thr Ser Arg Gly Ala Leu Phe Gln Glu Ile
        755                 760                 765

Ser Ser Asn Asp Ile Ser Ser Lys Leu Thr Leu Leu Thr Leu His Phe
    770                 775                 780
```

-continued

```
Pro Arg Leu Arg Ile Leu Trp Cys Pro Ser Pro His Ala Thr Ala Glu
785                 790                 795                 800

Leu Phe Glu Glu Leu Lys Gln Ser Lys Pro Gln Pro Asp Ala Ala Thr
                805                 810                 815

Ala Leu Ala Ile Thr Ala Asp Ser Glu Thr Leu Pro Glu Ser Glu Lys
            820                 825                 830

Tyr Asn Pro Gly Pro Gln Asp Phe Leu Leu Lys Met Pro Gly Val Asn
        835                 840                 845

Ala Lys Asn Cys Arg Ser Leu Met His His Val Lys Asn Ile Ala Glu
    850                 855                 860

Leu Ala Ala Leu Ser Gln Asp Glu Leu Thr Ser Ile Leu Gly Asn Ala
865                 870                 875                 880

Ala Asn Ala Lys Gln Leu Tyr Asp Phe Ile His Thr Ser Phe Ala Glu
                885                 890                 895

Val Val Ser Lys Gly Lys Gly Lys Lys Glx
            900                 905


<210> SEQ ID NO 14
<211> LENGTH: 2718
<212> TYPE: DNA
<213> ORGANISM: Homo sapiens

<400> SEQUENCE: 14

atggcgccgc tgctggagta cgagcgacag ctggtgctgg aactgctcga cactgacggg     60

ctagtagtgt gcgcccgcgg gctcggcgcg gaccggctcc tctaccactt tctccagctg    120

cactgccacc cagcctgcct ggtgctggtg ctcaacacgc agccggccga ggaggagtat    180

tttatcaatc agctgaagat agaaggagtt gaacacctcc ctcgccgtgt aacaaatgaa    240

atcacaagca acagtcgcta tgaagtttac acacaaggtg gtgttatatt tgcgacaagt    300

aggatacttg tggttgactt cttgactgat agaatacctt cagatttaat tactggcatc    360

ttggtgtata gagcccacag aataatcgag tcttgtcaag aagcattcat cttgcgcctc    420

tttcgccaga aaaacaaacg tggttttatt aaagctttca cagacaatgc tgttgccttt    480

gatactggtt tttgtcatgt ggaaagagtg atgagaaatc tttttgtgag gaaactgtat    540

ctgtggccaa ggttccatgt agcagtaaac tcatttttag aacagcacaa acctgaagtt    600

gtagaaatcc atgtttctat gacacctacc atgcttgcta tacagactgc tatactggac    660

attttaaatg catgtctaaa ggaactaaaa tgccataacc catcgcttga agtggaagat    720

ttatctttag aaaatgctat tggaaaacct tttgacaaga caatccgcca ttatctggat    780

cctttgtggc accagcttgg agccaagact aaatccttag ttcaggattt gaagatatta    840

cgaactttgc tgcagtatct ctctcagtat gattgtgtca catttcttaa tcttctggaa    900

tctctgagag caacggaaaa agcttttggt cagaattcag gttggctgtt tcttgactcc    960

agcacctcga tgtttataaa tgctcgagca agggtttatc atcttccaga tgccaaaatg   1020

agtaaaaaag aaaaaatatc tgaaaaaatg gaaattaaag aaggggaaga aacaaaaaag   1080

gaactggtcc tagaaagcaa cccaaagtgg gaggcactga ctgaagtatt aaaagaaatt   1140

gaggcagaaa ataaggagag tgaagctctt ggtggtccag gtcaagtact gatttgtgca   1200

agtgatgacc gaacatgttc ccagctgaga gactatatca ctcttggagc ggaggccttc   1260

ttattgaggc tctacaggaa aacctttgag aaggatagca aagctgaaga agtctggatg   1320

aaatttagga aggaagacag ttcaaagaga attaggaaat ctcacaaaag acctaaagac   1380

ccccaaaaca aagaacgggc ttctaccaaa gaaagaaccc tcaaaaagaa aaaacggaag   1440
```

-continued

```
ttgaccttaa ctcaaatggt aggaaaacct gaagaactgg aagaggaagg agatgtcgag   1500

gaaggatatc gtcgagaaat aagcagtagc ccagaaagct gcccggaaga aattaagcat   1560

gaagaatttg atgtaaattt gtcatcggat gctgctttcg gaatcctgaa agaacccctc   1620

actatcatcc atccgcttct gggttgcagc gacccctatg ctctgacaag ggtactacat   1680

gaagtggagc caagatacgt ggttctttat gacgcagagc taacctttgt tcggcagctt   1740

gaaatttaca gggcgagtag gcctgggaaa cctctgaggg tttactttct tatatacgga   1800

ggttcaactg aggaacaacg ctatctcact gctttgcgga aagaaaagga agcttttgaa   1860

aaactcataa gggaaaaagc aagcatggtt gtccctgaag aaagagaagg cagagatgaa   1920

acaaacttag acctagtaag aggcacagca tctgcagatg tttccactga cactcggaaa   1980

gccggtggcc aggaacagaa tggtacacag caaagcatag ttgtggatat gcgtgaattt   2040

cgaagtgagc ttccatctct gatccatcgt cggggcattg acattgaacc cgtgacttta   2100

gaggttggag attacatcct cactccagaa atgtgcgtgg agcgcaagag tatcagtgat   2160

ttaatcggct ctttaaataa cggccgcctc tacagccagt gcatctccat gtcccgctac   2220

tacaagcgtc ccgtgcttct gattgagttt gaccctagca agcctttctc tctcacttcc   2280

cgaggtgcct tgtttcagga gatctccagc aatgacatta gttccaaact cactcttctt   2340

acacttcact tccccagact acggattctc tggtgcccct ctcctcatgc aacggcggag   2400

ttgtttgagg agctgaaaca aagcaagcca cagcctgatg cggcgacagc actggccatt   2460

acagcagatt ctgaaaccct tcccgagtca gagaagtata atcctggtcc ccaagacttc   2520

ttgttaaaaa tgccaggggt gaatgccaaa aactgccgct ccttgatgca ccacgttaag   2580

aacatcgcag aattagcagc cctgtcacaa gacgagctca cgagtattct ggggaatgct   2640

gcaaatgcca aacagcttta tgatttcatt cacacctctt ttgcagaagt cgtatcaaaa   2700

ggaaaaggga aaaagtga                                                 2718
```

```
<210> SEQ ID NO 15
<211> LENGTH: 819
<212> TYPE: PRT
<213> ORGANISM: Thermus thermophilus

<400> SEQUENCE: 15

Met Gly Gly Tyr Gly Gly Val Lys Met Glu Gly Met Leu Lys Gly Glu
  1               5                  10                  15

Gly Pro Gly Pro Leu Pro Pro Leu Leu Gln Gln Tyr Val Glu Leu Arg
             20                  25                  30

Asp Arg Tyr Pro Asp Tyr Leu Leu Leu Phe Gln Val Gly Asp Phe Tyr
         35                  40                  45

Glu Cys Phe Gly Glu Asp Ala Glu Arg Leu Ala Arg Ala Leu Gly Leu
     50                  55                  60

Val Leu Thr His Lys Thr Ser Lys Asp Phe Thr Thr Pro Met Ala Gly
 65                  70                  75                  80

Ile Pro Ile Arg Ala Phe Asp Ala Tyr Ala Glu Arg Leu Leu Lys Met
                 85                  90                  95

Gly Phe Arg Leu Ala Val Ala Asp Gln Val Glu Pro Ala Glu Glu Ala
            100                 105                 110

Glu Gly Leu Val Arg Arg Glu Val Thr Gln Leu Leu Thr Pro Gly Thr
        115                 120                 125

Leu Thr Gln Glu Ala Leu Leu Pro Arg Glu Ala Asn Tyr Leu Ala Ala
    130                 135                 140
```

-continued

```
Ile Ala Thr Gly Asp Gly Trp Gly Leu Ala Phe Leu Asp Val Ser Thr
145                 150                 155                 160

Gly Glu Phe Lys Gly Thr Leu Leu Lys Ser Lys Ser Ala Leu Tyr Asp
                165                 170                 175

Glu Leu Phe Arg His Arg Pro Ala Glu Val Leu Leu Ala Pro Glu Leu
            180                 185                 190

Arg Glu Asn Glu Ala Phe Val Ala Glu Phe Arg Lys Arg Phe Pro Val
        195                 200                 205

Met Leu Ser Glu Ala Pro Phe Glu Pro Gln Gly Glu Gly Pro Leu Ala
    210                 215                 220

Leu Arg Arg Ala Gln Gly Ala Leu Leu Ala Tyr Ala Arg Ala Thr Gln
225                 230                 235                 240

Gly Gly Ala Leu Ser Val Arg Pro Phe Arg Leu Tyr Asp Pro Gly Ala
                245                 250                 255

Phe Val Arg Leu Pro Glu Ala Ser Leu Lys Ala Leu Glu Val Phe Glu
            260                 265                 270

Pro Leu Arg Gly Gln Asp Thr Leu Phe Gly Val Leu Asp Glu Thr Arg
        275                 280                 285

Thr Ala Pro Gly Arg Arg Leu Leu Gln Ala Trp Leu Arg His Pro Leu
    290                 295                 300

Leu Glu Arg Gly Pro Leu Glu Ala Arg Leu Asp Arg Val Glu Arg Phe
305                 310                 315                 320

Val Arg Glu Gly Ala Leu Arg Glu Gly Val Arg Arg Leu Leu Phe Arg
                325                 330                 335

Leu Ala Asp Leu Glu Arg Leu Ala Thr Arg Leu Glu Leu Ser Arg Ala
            340                 345                 350

Ser Pro Arg Asp Leu Ala Ala Leu Arg Arg Ser Leu Glu Ile Leu Pro
        355                 360                 365

Glu Leu Lys Gly Leu Leu Gly Glu Glu Val Gly Leu Pro Asp Leu Ser
    370                 375                 380

Gly Leu Leu Glu Glu Leu Arg Ala Ala Leu Val Glu Asp Pro Pro Leu
385                 390                 395                 400

Lys Val Ser Glu Gly Gly Leu Ile Arg Glu Gly Tyr Asp Pro Asp Leu
                405                 410                 415

Asp Ala Leu Arg Arg Ala His Ala Glu Gly Val Ala Tyr Phe Leu Asp
            420                 425                 430

Leu Glu Ala Arg Glu Lys Glu Arg Thr Gly Ile Pro Thr Leu Lys Val
        435                 440                 445

Gly Tyr Asn Ala Val Phe Gly Tyr Tyr Leu Glu Val Thr Arg Pro Tyr
    450                 455                 460

Tyr Glu Lys Val Pro Gln Glu Tyr Arg Pro Val Gln Thr Leu Lys Asp
465                 470                 475                 480

Arg Gln Arg Tyr Thr Leu Pro Glu Met Lys Glu Arg Glu Arg Glu Leu
                485                 490                 495

Tyr Arg Leu Glu Ala Leu Ile Lys Arg Arg Glu Glu Glu Val Phe Leu
            500                 505                 510

Ala Leu Arg Glu Arg Ala Arg Lys Glu Ala Glu Ala Leu Arg Glu Ala
        515                 520                 525

Ala Arg Ile Leu Ala Glu Leu Asp Val Tyr Ala Ala Leu Ala Glu Val
    530                 535                 540

Ala Val Arg His Gly Tyr Thr Arg Pro Arg Phe Gly Glu Arg Leu Arg
545                 550                 555                 560
```

-continued

```
Ile Arg Ala Gly Arg His Pro Val Val Glu Arg Arg Thr Ala Phe Val
                565                 570                 575

Pro Asn Asp Leu Glu Met Ala His Glu Leu Val Leu Val Thr Gly Pro
            580                 585                 590

Asn Met Ala Gly Lys Ser Thr Phe Leu Arg Gln Thr Ala Leu Ile Ala
        595                 600                 605

Leu Leu Ala Gln Ile Gly Ser Phe Val Pro Ala Glu Glu Ala Glu Leu
    610                 615                 620

Pro Leu Phe Asp Gly Ile Tyr Thr Arg Ile Gly Ala Ser Asp Asp Leu
625                 630                 635                 640

Ala Gly Gly Lys Ser Thr Phe Met Val Glu Met Glu Glu Val Ala Leu
                645                 650                 655

Val Leu Lys Glu Ala Thr Glu Arg Ser Leu Val Leu Leu Asp Glu Val
            660                 665                 670

Gly Arg Gly Thr Ser Ser Leu Asp Gly Val Ala Ile Ala Thr Ala Leu
        675                 680                 685

Ala Glu Ala Leu His Glu Arg Arg Cys Tyr Thr Leu Phe Ala Thr His
    690                 695                 700

Tyr Phe Glu Leu Thr Ala Leu Ala Leu Pro Arg Leu Lys Asn Leu His
705                 710                 715                 720

Val Ala Ala Lys Glu Glu Glu Gly Gly Leu Val Phe Tyr His Gln Val
                725                 730                 735

Leu Pro Gly Pro Ala Ser Lys Ser Tyr Gly Val Glu Val Ala Glu Met
            740                 745                 750

Ala Gly Leu Pro Lys Glu Val Val Glu Arg Ala Arg Ala Leu Leu Ser
        755                 760                 765

Ala Met Ala Ala Arg Arg Glu Gly Ala Leu Glu Glu Val Leu Glu Arg
    770                 775                 780

Leu Leu Ala Leu Asp Pro Asp Arg Leu Thr Pro Leu Glu Ala Leu Arg
785                 790                 795                 800

Phe Leu His Glu Leu Lys Ala Leu Ala Leu Gly Leu Pro Leu Gly Ser
                805                 810                 815

Met Lys Gly


<210> SEQ ID NO 16
<211> LENGTH: 3283
<212> TYPE: DNA
<213> ORGANISM: Thermus thermophilus

<400> SEQUENCE: 16

tctagaaggt ccttaaggcg caccccacgg aaggtgacgt tccccacccc accccgtttc     60

caggggttgc ccgaggtgcg gggctggaag agggaacgcc cgttgccgga gcactggagg    120

accatggtca cctcgtgctg ggaagctcg aggagctcct tggcctcaaa ggtgaagggt    180

ttgtccacca gtccccccac ctccaccttc cacccgtcca ggctggcccc ctccacggtg    240

ttgtagccgg ggaggtccac gttgttgcgg atgtagagga tctccttagg ggtgcgctcg    300

ggctggctga ccaagaggtc ataaggagtt tccaaaacga tggggcgttg ggagagaacc    360

aagagcttgg ggtttttccc cttcaccaac tggtcggccg tgggggcttg ctgggcgaag    420

cctcggcttc ccgcggccaa aagcgctgcc cctaggccca tgagcttcag ggcggttcgc    480

cggctgacgc tttccatacc ttatccctcc ctccaagggt ccggggggac gtttgtcccc    540

actttccggt tgcccctaat ctaggtggca aacaacaccc atgtcaagtg ggggttaggg    600

ggtttttagc ccccgtttaa ggggctagga gaaagcgcta atggggggt atggcggagt    660
```

-continued

```
taagatggaa ggcatgctca agggcgaagg cccaggtcca cttccccctc ttctgcagca    720
gtacgtggag ctccgcgacc gctacccgga ctacctcctc ctcttccagg tgggggactt    780
ctacgagtgc ttcggggagg acgccgagcg cctcgcccgc gcgcttggcc tcgtcctcac    840
ccacaagacc agcaaggact tcaccacccc catggcgggg atccccataa gggcctttga    900
cgcctacgcc gaaaggcttc ttaagatggg cttccgcctg gcggtggccg accaggtgga    960
gcctgccgag gaggcggaag gcctggtgcg tcgggaggtg acccagctcc tcaccccggg   1020
gaccctcacc caggaggccc tcctccccg ggaggccaac tacctggccg ccatcgccac    1080
cggggacggg tggggtctgg cctttctgga cgtctccacg gggggagttca aggggaccct   1140
cctcaagagc aaaagtgccc tgtacgacga gcttttccgc caccggcccg ccgaggtcct   1200
tttggccccg gagctacggg agaacgaggc cttcgtggcc gagttccgga agcgctttcc   1260
cgtgatgctc tccgaggccc cctttgagcc ccaggggggag ggtcctttgg ccctgaggcg  1320
ggcccagggg gcgctccttg cctacgcccg ggccacccag gggggggcct tgagcgtgcg   1380
ccctttccgc ctctacgacc ccggggcctt cgtgcgccta ccggaggcga gcctgaaggc   1440
cctcgaggtc tttgaaccct tgcggggcca ggacaccctc tttggcgttc tggacgagac   1500
gcgaaccgcc cccggaagaa ggctcctcca ggcctggctc cgccaccccc ttctggaaag   1560
ggggcccttg gaggcgaggc ttgaccgggt ggagcgcttc gtgcgggagg gggccctacg   1620
cgagggggtg aggcgcctcc tcttccgcct cgccgacctg gagcgcctgg ccacgaggct   1680
ggagctttcc cgggcaagcc ccagggacct tgccgcccta aggcggagcc tggagatcct   1740
ccccgagctt aagggccttc tgggggagga ggtggggctt cccgacctct ccggcctttt   1800
ggaggagctt agggcggctt tggtggagga cccgcccctc aaggtctccg agggggggct   1860
catccgggag gggtacgacc cggacctgga cgccttgagg cgggcccacg ccgagggggt   1920
ggcctacttc ctggacctcg aggcccggga gaaggagagg acgggcatcc ccaccctcaa   1980
ggtggggtac aacgccgtct tcggctacta cctggaggtg acccggccct actacgagaa   2040
ggtgccccag gagtaccgcc ccgtccagac cctcaaggac cggcagcgct acaccctgcc   2100
ggagatgaag gaaagggagc gggagctcta ccgcctcgag gccctgatca aaaggcgcga   2160
ggaggaggtc ttccttgccc ttagggagcg ggcgaggaag gaggcggagg ccctaaggga   2220
ggcggcgagg atcctcgccg agcttgacgt ctacgccgcc ctcgccgagg tggcggtgcg   2280
ccacggctac acccggcccc gcttcgggga aaggcttcgg atcagggcgg ggcgccaccc   2340
ggtggtggag cgccgcaccg ccttcgtccc caacgacctg gagatggccc acgagctcgt   2400
cctcgtcacc gggcccaaca tggcggggaa gtccaccttc ctccgccaga ccgccctcat   2460
cgccctcctc gcccagatcg ggagcttcgt gcccgccgag gaggcggagc ttcccctctt   2520
tgacgggatc tacacgagga tcggggcctc ggacgacctc gccgggggga agagcacctt   2580
catggtggag atggaggagg tggccctggt gctcaaggag gccaccgaac gtagcctcgt   2640
cctcctggac gaggtgggcc ggggcacgag cagcctggac ggggtggcca tcgccaccgc   2700
cctcgccgag gccctgcacg agcggcggtg ctacaccctc ttcgccaccc actactttga   2760
gctcaccgcc ctcgcccttc cccggctcaa gaacctgcac gtggccgcca aggaggagga   2820
ggggggctc gtcttctacc accaggtcct ccccgggccc gcctccaaga gctacggggt     2880
ggaggtggcg gagatggcgg gcctgcccaa ggaggtggtg gagcgggccc gcgccctcct   2940
cagcgccatg gccgcgaggc gggagggcgc cctggaggag gtcttggagc gcctcctcgc   3000
```

-continued

```
cttagacccc gaccgcctca cccccctcga ggccctgagg ttcctccacg agctcaaggc   3060

cttggccctg ggcctccccc tgggtagcat gaaggggtga tccgccccct ccctccggag   3120

cttaggggcc tcctcgcccg gggcgaggtg ctccttacgg tgaaggacgc cgtgcgggag   3180

cttctggaaa acgccctgga cgctggggcc aggagggtgc gggtggagct ttggggcggg   3240

gggcttaagc ggcttgtggt ggaggacgac ggggagggga tcc                     3283
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:Linker

<400> SEQUENCE: 17

```
Gly Ser Gly Pro Ser Pro Gly Ser
  1               5
```

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Linker

<400> SEQUENCE: 18

```
ggtagtggtc ctagtcctgg tagt                                            24
```

<210> SEQ ID NO 19
<211> LENGTH: 823
<212> TYPE: PRT
<213> ORGANISM: Homo sapiens

<400> SEQUENCE: 19

```
Met Asn Glu Asp Ser Asn Glu Glu Glu Glu Glu Ser Glu Asn Asp Trp
  1               5                  10                  15

Glu Glu Val Glu Glu Leu Ser Glu Pro Val Leu Gly Asp Val Arg Glu
             20                  25                  30

Ser Thr Ala Phe Ser Arg Ser Leu Leu Pro Val Lys Pro Val Glu Ile
         35                  40                  45

Glu Ile Glu Thr Pro Glu Gln Ala Lys Thr Arg Glu Arg Ser Glu Lys
     50                  55                  60

Ile Lys Leu Glu Phe Glu Thr Tyr Leu Arg Arg Ala Met Lys Arg Phe
 65                  70                  75                  80

Asn Lys Gly Val His Glu Asp Thr His Lys Val His Leu Leu Cys Leu
                 85                  90                  95

Leu Ala Asn Gly Phe Tyr Arg Asn Asn Ile Cys Ser Gln Pro Asp Leu
            100                 105                 110

His Ala Ile Gly Leu Ser Ile Ile Pro Ala Arg Phe Thr Arg Val Leu
        115                 120                 125

Pro Arg Asp Val Asp Thr Tyr Tyr Leu Ser Asn Leu Val Lys Trp Phe
    130                 135                 140

Ile Gly Thr Phe Thr Val Asn Ala Glu Leu Ser Ala Ser Glu Gln Asp
145                 150                 155                 160

Asn Leu Gln Thr Thr Leu Glu Arg Arg Phe Ala Ile Tyr Ser Ala Arg
                165                 170                 175

Asp Asp Glu Glu Leu Val His Ile Phe Leu Leu Ile Leu Arg Ala Leu
            180                 185                 190
```

-continued

```
Gln Leu Leu Thr Arg Leu Val Leu Ser Leu Gln Pro Ile Pro Leu Lys
        195                 200                 205

Ser Ala Thr Ala Lys Gly Lys Lys Pro Ser Lys Glu Arg Leu Thr Ala
    210                 215                 220

Asp Pro Gly Gly Ser Ser Glu Thr Ser Ser Gln Val Leu Glu Asn His
225                 230                 235                 240

Thr Lys Pro Lys Thr Ser Lys Gly Thr Lys Gln Glu Glu Thr Phe Ala
                245                 250                 255

Lys Gly Thr Cys Arg Pro Ser Ala Lys Gly Lys Arg Asn Lys Gly Gly
            260                 265                 270

Arg Lys Lys Arg Ser Lys Pro Ser Ser Ser Glu Glu Asp Glu Gly Pro
        275                 280                 285

Gly Asp Lys Gln Glu Lys Ala Thr Gln Arg Arg Pro His Gly Arg Glu
    290                 295                 300

Arg Arg Val Ala Ser Arg Val Ser Tyr Lys Glu Glu Ser Gly Ser Asp
305                 310                 315                 320

Glu Ala Gly Ser Gly Ser Asp Phe Glu Leu Ser Ser Gly Glu Ala Ser
                325                 330                 335

Asp Pro Ser Asp Glu Asp Ser Glu Pro Gly Pro Pro Lys Gln Arg Lys
            340                 345                 350

Ala Pro Ala Pro Gln Arg Thr Lys Ala Gly Ser Lys Ser Ala Ser Arg
        355                 360                 365

Thr His Arg Gly Ser His Arg Lys Asp Pro Ser Leu Pro Ala Ala Ser
    370                 375                 380

Ser Ser Ser Ser Ser Ser Lys Arg Gly Lys Lys Met Cys Ser Asp Gly
385                 390                 395                 400

Glu Lys Ala Glu Lys Arg Ser Ile Ala Gly Ile Asp Gln Trp Leu Glu
                405                 410                 415

Val Phe Cys Glu Gln Glu Glu Lys Trp Val Cys Val Asp Cys Val His
            420                 425                 430

Gly Val Val Gly Gln Pro Leu Thr Cys Tyr Lys Tyr Ala Thr Lys Pro
        435                 440                 445

Met Thr Tyr Val Val Gly Ile Asp Ser Asp Gly Trp Val Arg Asp Val
    450                 455                 460

Thr Gln Arg Tyr Asp Pro Val Trp Met Thr Val Thr Arg Lys Cys Arg
465                 470                 475                 480

Val Asp Ala Glu Trp Trp Ala Glu Thr Leu Arg Pro Tyr Gln Ser Pro
                485                 490                 495

Phe Met Asp Arg Glu Lys Lys Glu Asp Leu Glu Phe Gln Ala Lys His
            500                 505                 510

Met Asp Gln Pro Leu Pro Thr Ala Ile Gly Leu Tyr Lys Asn His Pro
        515                 520                 525

Leu Tyr Ala Leu Lys Arg His Leu Leu Lys Tyr Glu Ala Ile Tyr Pro
    530                 535                 540

Glu Thr Ala Ala Ile Leu Gly Tyr Cys Arg Gly Glu Ala Val Tyr Ser
545                 550                 555                 560

Arg Asp Cys Val His Thr Leu His Ser Arg Asp Thr Trp Leu Lys Lys
                565                 570                 575

Ala Arg Val Val Arg Leu Gly Glu Val Pro Tyr Lys Met Val Lys Gly
            580                 585                 590

Phe Ser Asn Arg Ala Arg Lys Ala Arg Leu Ala Glu Pro Gln Leu Arg
        595                 600                 605

Glu Glu Asn Asp Leu Gly Leu Phe Gly Tyr Trp Gln Thr Glu Glu Tyr
```

-continued

```
    610                 615                 620

Gln Pro Pro Val Ala Val Asp Gly Lys Val Pro Arg Asn Glu Phe Gly
625                 630                 635                 640

Asn Val Tyr Leu Phe Leu Pro Ser Met Met Pro Ile Gly Cys Val Gln
                645                 650                 655

Leu Asn Leu Pro Asn Leu His Arg Val Ala Arg Lys Leu Asp Ile Asp
            660                 665                 670

Cys Val Gln Ala Ile Thr Gly Phe Asp Phe His Gly Gly Tyr Ser His
        675                 680                 685

Pro Val Thr Asp Gly Tyr Ile Val Cys Glu Glu Phe Lys Asp Val Leu
    690                 695                 700

Leu Thr Ala Trp Glu Asn Glu Gln Ala Val Ile Glu Arg Lys Glu Lys
705                 710                 715                 720

Glu Lys Lys Glu Lys Arg Ala Leu Gly Asn Trp Lys Leu Leu Ala Lys
                725                 730                 735

Gly Leu Leu Ile Arg Glu Arg Leu Lys Arg Arg Tyr Gly Pro Lys Ser
            740                 745                 750

Glu Ala Ala Ala Pro His Thr Asp Ala Gly Gly Gly Leu Ser Ser Asp
        755                 760                 765

Glu Glu Glu Gly Thr Ser Ser Gln Ala Glu Ala Ala Arg Ile Leu Ala
    770                 775                 780

Ala Ser Trp Pro Gln Asn Arg Glu Asp Glu Glu Lys Gln Lys Leu Lys
785                 790                 795                 800

Gly Gly Pro Lys Lys Thr Lys Arg Glu Lys Lys Ala Ala Ala Ser His
                805                 810                 815

Leu Phe Pro Phe Glu Lys Leu
            820


<210> SEQ ID NO 20
<211> LENGTH: 3455
<212> TYPE: DNA
<213> ORGANISM: Homo sapiens

<400> SEQUENCE: 20

gaaagaggaa aagaggctgc ggtcatcctg gggttcagc agatggtcca gcaaaaaaga     60

aagtggccaa ggtgactgtt aaatctgaaa acctcaaggt tataaaggat gaagccctca    120

gcgatgggga tgacctcagg gactttccaa gtgacctcaa gaaggcacac catctgaaga    180

gaggggctac catgaatgaa gacagcaatg aagaagagga agaaagtgaa aatgattggg    240

aagaggttga agaacttagt gagcctgtgc tgggtgacgt gagagaaagt acagccttct    300

ctcgatctct tctgcctgtg aagccagtgg agatagagat tgaaacgcca gagcaggcga    360

agacaagaga aagaagtgaa aagataaaac tggagtttga gacatatctt cggagggcga    420

tgaaacgttt caataaaggg gtccatgagg acacacacaa ggttcacctt ctctgcctgc    480

tagcaaatgg cttctatcga aataacatct gcagccagcc agatctgcat gctattggcc    540

tgtccatcat cccagcccgc tttaccagag tgctgcctcg agatgtggac acctactacc    600

tctcaaacct ggtgaagtgg ttcattggaa catttacagt taatgcagaa ctttcagcca    660

gtgaacaaga taacctgcag actacattgg aaaggagatt tgctatttac tctgctcgag    720

atgatgagga attggtccat atattcttac tgattctccg ggctctgcag ctcttgaccc    780

ggctggtatt gtctctacag ccaattcctc tgaagtcagc aacagcaaag ggaaagaaac    840

cttccaagga aagattgact gcggatccag gaggctcctc agaaacttcc agccaagttc    900
```

-continued

```
tagaaaacca caccaaacca aagaccagca aaggaaccaa acaagaggaa acctttgcta    960
agggcacctg caggccaagt gccaaaggga agaggaacaa gggaggcaga aagaaacgga   1020
gcaagccctc ctccagcgag gaagatgagg gcccaggaga caagcaggag aaggcaaccc   1080
agcgacgtcc gcatggccgg gagcggcggg tggcctccag ggtgtcttat aaagaggaga   1140
gtgggagtga tgaggctggc agcggctctg attttgagct ctccagtgga gaagcctctg   1200
atccctctga tgaggattcc gaacctggcc ctccaaagca gaggaaagcc cccgctcctc   1260
agaggacaaa ggctgggtcc aagagtgcct ccaggaccca tcgtgggagc catcgtaagg   1320
acccaagctt gccagcggca tcctcaagct cttcaagcag taaaagaggc aagaaaatgt   1380
gcagcgatgg tgagaaggca gaaaaaagaa gcatagctgg tatagaccag tggctagagg   1440
tgttctgtga gcaggaggaa aagtgggtat gtgtagactg tgtgcacggt gtggtgggcc   1500
agcctctgac ctgttacaag tacgccacca agcccatgac ctatgtggtg ggcattgaca   1560
gtgacggctg ggtccgagat gtcacacaga ggtacgaccc agtctggatg acagtgaccc   1620
gcaagtgccg ggttgatgct gagtggtggg ccgagacctt gagaccatac cagagcccat   1680
ttatggacag ggagaagaaa gaagacttgg agtttcaggc aaaacacatg gaccagcctt   1740
tgcccactgc cattggctta tataagaacc accctctgta tgccctgaag cggcatctcc   1800
tgaaatatga ggccatctat cccgagacag ctgccatcct tgggtattgt cgtggagaag   1860
cggtctactc cagggattgt gtgcacactc tgcattccag agacacgtgg ctgaagaaag   1920
caagagtggt gaggcttgga gaagtaccct acaagatggt gaaaggcttt tctaaccgtg   1980
ctcggaaagc ccgacttgct gagccccagc tgcgggaaga aaatgacctg ggcctgtttg   2040
gctactggca gacagaggag tatcagcccc cagtggccgt ggacgggaag gtgccccgga   2100
acgagtttgg gaatgtgtac ctcttcctgc ccagcatgat gcctattggc tgtgtccagc   2160
tgaacctgcc caatctacac cgcgtggccc gcaagctgga catcgactgt gtccaggcca   2220
tcactggctt tgatttccat ggcggctact cccatcccgt gactgatgga tacatcgtct   2280
gcgaggaatt caaagacgtg ctcctgactg cctgggaaaa tgagcaggca gtcattgaaa   2340
ggaaggagaa ggagaaaaag gagaagcggg ctctagggaa ctggaagttg ctggccaaag   2400
gtctgctcat cagggagagg ctgaagcgtc gctacgggcc caagagtgag gcagcagctc   2460
cccacacaga tgcaggaggt ggactctctt ctgatgaaga ggaggggacc agctctcaag   2520
cagaagcggc caggatactg gctgcctcct ggcctcaaaa ccgagaagat gaagaaaagc   2580
agaagctgaa gggtgggccc aagaagacca aaagggaaaa gaaagcagca gcttcccacc   2640
tgttcccatt tgagaagctg tgagctgagc gcccactaga ggggcaccca ccagttgctg   2700
ctgccccact acaggcccca cacctgccct gggcatgccc agcccctggt ggtgggggct   2760
tctctgctga gaaggcaaac tgaggcagca tgcacggagg cggggtcagg ggagacgagg   2820
ccaagctgag gaggtgctgc aggtcccgtc tggctccagc ccttgtcaga ttcacccagg   2880
gtgaagcctt caaagctttt tgctaccaaa gcccactcac cctttgagct acagaacact   2940
ttgctaggag atactcttct gcctcctaga cctgttcttt ccatctttag aaacatcagt   3000
ttttgtatgg aagccaccgg gagatttctg gatggtggtg catccgtgaa tgcgctgatc   3060
gtttcttcca gttagagtct tcatctgtcc gacaagttca ctcgcctcgg ttgcggacct   3120
aggaccattt ctctgcaggc cacttacctt cccctgagtc aggcttacta atgctgccct   3180
cactgcctct ttgcagtagg ggagagagca gagaagtaca ggtcatctgc tgggatctag   3240
ttttccaagt aacattttgt ggtgacagaa gcctaaaaaa agctaaaatc aggaaagaaa   3300
```

-continued

```
aggaaaaata cgaattgaaa attaaggaaa tgttagtaaa atagatcagt gttaaactag   3360

attgtattca ttactagata aaatgtataa agctctctgt actaaggaga aatgactttt   3420

ataacatttt gagaaaataa taaagcattt atcta                              3455


<210> SEQ ID NO 21
<211> LENGTH: 1140
<212> TYPE: PRT
<213> ORGANISM: Homo sapiens

<400> SEQUENCE: 21

Met Ser Tyr Asn Tyr Val Val Thr Ala Gln Lys Pro Thr Ala Val Asn
  1               5                  10                  15

Gly Cys Val Thr Gly His Phe Thr Ser Ala Glu Asp Leu Asn Leu Leu
             20                  25                  30

Ile Ala Lys Asn Thr Arg Leu Glu Ile Tyr Val Val Thr Ala Glu Gly
         35                  40                  45

Leu Arg Pro Val Lys Glu Val Gly Met Tyr Gly Lys Ile Ala Val Met
     50                  55                  60

Glu Leu Phe Arg Pro Lys Gly Glu Ser Lys Asp Leu Leu Phe Ile Leu
 65                  70                  75                  80

Thr Ala Lys Tyr Asn Ala Cys Ile Leu Glu Tyr Lys Gln Ser Gly Glu
                 85                  90                  95

Ser Ile Asp Ile Ile Thr Arg Ala His Gly Asn Val Gln Asp Arg Ile
            100                 105                 110

Gly Arg Pro Ser Glu Thr Gly Ile Ile Gly Ile Ile Asp Pro Glu Cys
        115                 120                 125

Arg Met Ile Gly Leu Arg Leu Tyr Asp Gly Leu Phe Lys Val Ile Pro
    130                 135                 140

Leu Asp Arg Asp Asn Lys Glu Leu Lys Ala Phe Asn Ile Arg Leu Glu
145                 150                 155                 160

Glu Leu His Val Ile Asp Val Lys Phe Leu Tyr Gly Cys Gln Ala Pro
                165                 170                 175

Thr Ile Cys Phe Val Tyr Gln Asp Pro Gln Gly Arg His Val Lys Thr
            180                 185                 190

Tyr Glu Val Ser Leu Arg Glu Lys Glu Phe Asn Lys Gly Pro Trp Lys
        195                 200                 205

Gln Glu Asn Val Glu Ala Glu Ala Ser Met Val Ile Ala Val Pro Glu
    210                 215                 220

Pro Phe Gly Gly Ala Ile Ile Ile Gly Gln Glu Ser Ile Thr Tyr His
225                 230                 235                 240

Asn Gly Asp Lys Tyr Leu Ala Ile Ala Pro Pro Ile Ile Lys Gln Ser
                245                 250                 255

Thr Ile Val Cys His Asn Arg Val Asp Pro Asn Gly Ser Arg Tyr Leu
            260                 265                 270

Leu Gly Asp Met Glu Gly Arg Leu Phe Met Leu Leu Leu Glu Lys Glu
        275                 280                 285

Glu Gln Met Asp Gly Thr Val Thr Leu Lys Asp Leu Arg Val Glu Leu
    290                 295                 300

Leu Gly Glu Thr Ser Ile Ala Glu Cys Leu Thr Tyr Leu Asp Asn Gly
305                 310                 315                 320

Val Val Phe Val Gly Ser Arg Leu Gly Asp Ser Gln Leu Val Lys Leu
                325                 330                 335

Asn Val Asp Ser Asn Glu Gln Gly Ser Tyr Val Val Ala Met Glu Thr
```

-continued

```
            340                 345                 350

Phe Thr Asn Leu Gly Pro Ile Val Asp Met Cys Val Val Asp Leu Glu
        355                 360                 365

Arg Gln Gly Gln Gly Gln Leu Val Thr Cys Ser Gly Ala Phe Lys Glu
    370                 375                 380

Gly Ser Leu Arg Ile Ile Arg Asn Gly Ile Gly Ile His Glu His Ala
385                 390                 395                 400

Ser Ile Asp Leu Pro Gly Ile Lys Gly Leu Trp Pro Leu Arg Ser Asp
                405                 410                 415

Pro Asn Arg Glu Thr Tyr Asp Thr Leu Val Leu Ser Phe Val Gly Gln
            420                 425                 430

Thr Arg Val Leu Met Leu Asn Gly Glu Glu Val Glu Glu Thr Glu Leu
        435                 440                 445

Met Gly Phe Val Asp Asp Gln Gln Thr Phe Phe Cys Gly Asn Val Ala
    450                 455                 460

His Gln Gln Leu Ile Gln Ile Thr Ser Ala Ser Val Arg Leu Val Ser
465                 470                 475                 480

Gln Glu Pro Lys Ala Leu Val Ser Glu Trp Lys Glu Pro Gln Ala Lys
                485                 490                 495

Asn Ile Ser Val Ala Ser Cys Asn Ser Ser Gln Val Val Val Ala Val
            500                 505                 510

Gly Arg Ala Leu Tyr Tyr Leu Gln Ile His Pro Gln Glu Leu Arg Gln
        515                 520                 525

Ile Ser His Thr Glu Met Glu His Glu Val Ala Cys Leu Asp Ile Thr
    530                 535                 540

Pro Leu Gly Asp Ser Asn Gly Leu Ser Pro Leu Cys Ala Ile Gly Leu
545                 550                 555                 560

Trp Thr Asp Ile Ser Ala Arg Ile Leu Lys Leu Pro Ser Phe Glu Leu
                565                 570                 575

Leu His Lys Glu Met Leu Gly Gly Glu Ile Ile Pro Arg Ser Ile Leu
            580                 585                 590

Met Thr Thr Phe Glu Ser Ser His Tyr Leu Leu Cys Ala Leu Gly Asp
        595                 600                 605

Gly Ala Leu Phe Tyr Phe Gly Leu Asn Ile Glu Thr Gly Leu Leu Ser
    610                 615                 620

Asp Arg Lys Lys Val Thr Leu Gly Thr Gln Pro Thr Val Leu Arg Thr
625                 630                 635                 640

Phe Arg Ser Leu Ser Thr Thr Asn Val Phe Ala Cys Ser Asp Arg Pro
                645                 650                 655

Thr Val Ile Tyr Ser Ser Asn His Lys Leu Val Phe Ser Asn Val Asn
            660                 665                 670

Leu Lys Glu Val Asn Tyr Met Cys Pro Leu Asn Ser Asp Gly Tyr Pro
        675                 680                 685

Asp Ser Leu Ala Leu Ala Asn Asn Ser Thr Leu Thr Ile Gly Thr Ile
    690                 695                 700

Asp Glu Ile Gln Lys Leu His Ile Arg Thr Val Pro Leu Tyr Glu Ser
705                 710                 715                 720

Pro Arg Lys Ile Cys Tyr Gln Glu Val Ser Gln Cys Phe Gly Val Leu
                725                 730                 735

Ser Ser Arg Ile Glu Val Gln Asp Thr Ser Gly Gly Thr Thr Ala Leu
            740                 745                 750

Arg Pro Ser Ala Ser Thr Gln Ala Leu Ser Ser Ser Val Ser Ser Ser
        755                 760                 765
```

-continued

```
Lys Leu Phe Ser Ser Ser Thr Ala Pro His Glu Thr Ser Phe Gly Glu
    770                 775                 780

Glu Val Glu Val His Asn Leu Leu Ile Ile Asp Gln His Thr Phe Glu
785                 790                 795                 800

Val Leu His Ala His Gln Phe Leu Gln Asn Glu Tyr Ala Leu Ser Leu
                805                 810                 815

Val Ser Cys Lys Leu Gly Lys Asp Pro Asn Thr Tyr Phe Ile Val Gly
            820                 825                 830

Thr Ala Met Val Tyr Pro Glu Glu Ala Glu Pro Lys Gln Gly Arg Ile
        835                 840                 845

Val Val Phe Gln Tyr Ser Asp Gly Lys Leu Gln Thr Val Ala Glu Lys
    850                 855                 860

Glu Val Lys Gly Ala Val Tyr Ser Met Val Glu Phe Asn Gly Lys Leu
865                 870                 875                 880

Leu Ala Ser Ile Asn Ser Thr Val Arg Leu Tyr Glu Trp Thr Thr Glu
                885                 890                 895

Lys Asp Val Arg Thr Glu Cys Asn His Tyr Asn Asn Ile Met Ala Leu
            900                 905                 910

Tyr Leu Lys Thr Lys Gly Asp Phe Ile Leu Val Gly Asp Leu Met Arg
        915                 920                 925

Ser Val Leu Leu Leu Ala Tyr Lys Pro Met Glu Gly Asn Phe Glu Glu
    930                 935                 940

Ile Ala Arg Asp Phe Asn Pro Asn Trp Met Ser Ala Val Glu Ile Leu
945                 950                 955                 960

Asp Asp Asp Asn Phe Leu Gly Ala Glu Asn Ala Phe Asn Leu Phe Val
                965                 970                 975

Cys Gln Lys Asp Ser Ala Ala Thr Thr Asp Glu Glu Arg Gln His Leu
            980                 985                 990

Gln Glu Val Gly Leu Phe His Leu Gly Glu Phe Val Asn Val Phe Cys
        995                 1000                1005

His Gly Ser Leu Val Met Gln Asn Leu Gly Glu Thr Ser Thr Pro Thr
   1010                1015                1020

Gln Gly Ser Val Leu Phe Gly Thr Val Asn Gly Met Ile Gly Leu Val
1025                1030                1035                1040

Thr Ser Leu Ser Glu Ser Trp Tyr Asn Leu Leu Leu Asp Met Gln Asn
               1045                1050                1055

Arg Leu Asn Lys Val Ile Lys Ser Val Gly Lys Ile Glu His Ser Phe
           1060                1065                1070

Trp Arg Ser Phe His Thr Glu Arg Lys Thr Glu Pro Ala Thr Gly Phe
       1075                1080                1085

Ile Asp Gly Asp Leu Ile Glu Ser Phe Leu Asp Ile Ser Arg Pro Lys
   1090                1095                1100

Met Gln Glu Val Val Ala Asn Leu Gln Tyr Asp Asp Gly Ser Gly Met
1105                1110                1115                1120

Lys Arg Glu Ala Thr Ala Asp Asp Leu Ile Lys Val Val Glu Glu Leu
               1125                1130                1135

Thr Arg Ile His
           1140


<210> SEQ ID NO 22
<211> LENGTH: 4221
<212> TYPE: DNA
<213> ORGANISM: Homo sapiens
```

-continued

<400> SEQUENCE: 22

```
cagcggcagt ggagttcgct gcgcgctgtt gggggccacc tgtcttttcg cttgtgtccc     60
tctttctagt gtcgcgctcg agtcccgacg ggccgctcca agcctcgaca tgtcgtacaa    120
ctacgtggta acggcccaga agcccaccgc cgtgaacggc tgcgtgaccg gacactttac    180
ttcggccgaa gacttaaacc tgttgattgc caaaaacacg agattagaga tctatgtggt    240
caccgccgag ggcttcggc  ccgtcaaaga ggtgggcatg tatgggaaga ttgcggtcat    300
ggagcttttc aggcccaagg gggagagcaa ggacctgctg tttatcttga cagcgaagta    360
caatgcctgc atcctggagt ataaacagag tggcgagagc attgacatca ttacgcgagc    420
ccatggcaat gtccaggacc gcattggccg cccctcagag accggcatta ttggcatcat    480
tgaccctgag tgccggatga ttggcctgcg tctctatgat ggccttttca aggttattcc    540
actagatcgc gataataaag aactcaaggc cttcaacatc cgcctggagg agctgcatgt    600
cattgatgtc aagttcctat atggttgcca agcacctact atttgctttg tctaccagga    660
ccctcagggg cggcacgtaa aaacctatga ggtgtctctc cgagaaaagg aattcaataa    720
gggcccttgg aaacaggaaa atgtcgaagc tgaagcttcc atggtgatcg cagtcccaga    780
gccctttggg ggggccatca tcattggaca ggagtcaatc acctatcaca atggtgacaa    840
atacctggct attgcccctc ctatcatcaa gcaaagcacg attgtgtgcc acaatcgagt    900
ggaccctaat ggctcaagat acctgctggg agacatggaa ggccggctct tcatgctgct    960
tttggagaag gaggaacaga tggatggcac cgtcactctc aaggatctcc gtgtagaact   1020
ccttggagag acctctattg ctgagtgctt gacatacctt gataatggtg ttgtgtttgt   1080
cgggtctcgc ctgggtgact cccagcttgt gaagctcaac gttgacagta atgaacaagg   1140
ctcctatgta gtggccatgg aaacctttac caacttagga cccattgtcg atatgtgcgt   1200
ggtggacctg gagaggcagg ggcaggggca gctggtcact tgctctgggg ctttcaagga   1260
aggttctttg cggatcatcc ggaatggaat tggaatccac gagcatgcca gcattgactt   1320
accaggcatc aaaggattat ggccactgcg gtctgaccct aatcgtgaga cttatgacac   1380
tttggtgctc tcttttgtgg gccagacaag agttctcatg ttaaatggag aggaggtaga   1440
agaaaccgaa ctgatgggtt tcgtggatga tcagcagact ttcttctgtg gcaacgtggc   1500
tcatcagcag cttatccaga tcacttcagc atcggtgagg ttggtctctc aagaacccaa   1560
agctctggtc agtgaatgga aggagcctca ggccaagaac atcagtgtgg cctcctgcaa   1620
tagcagccag gtggtggtgg ctgtaggcag ggccctctac tatctgcaga tccatcctca   1680
ggagctccgg cagatcagcc acacagagat ggaacatgaa gtggcttgct tggacatcac   1740
cccattagga gacagcaatg gactgtcccc tctttgtgcc attggcctct ggacggacat   1800
ctcggctcgt atcttgaagt tgccctcttt tgaactactg cacaaggaga tgctgggtgg   1860
agagatcatt cctcgctcca tcctgatgac cacctttgag agtagccatt acctcctttg   1920
tgccttggga gatggagcgc ttttctactt tgggctcaac attgagacag gtctgttgag   1980
cgaccgtaag aaggtgactt tgggcaccca gcccaccgta ttgaggactt ttcgttctct   2040
ttctaccacc aacgtctttg cttgttctga ccgccccact gtcatctata gcagcaacca   2100
caaattggtc ttctcaaatg tcaacctcaa ggaagtgaac tacatgtgtc cctcaattc    2160
agatggctat cctgacagcc tggcgctggc caacaatagc accctcacca ttggcaccat   2220
cgatgagatc cagaagctgc acattcgcac agttcccctc tatgagtctc caaggaagat   2280
ctgctaccag gaagtgtccc agtgtttcgg ggtcctctcc agccgcattg aagtccaaga   2340
```

-continued

```
cacgagtggg ggcacgacag ccttgaggcc cagcgctagc acccaggctc tgtccagcag   2400

tgtaagctcc agcaagctgt tctccagcag cactgctcct catgagacct cctttggaga   2460

agaggtggag gtgcataacc tacttatcat tgaccaacac acctttgaag tgcttcatgc   2520

ccaccagttt ctgcagaatg aatatgccct cagtctggtt tcctgcaagc tgggcaaaga   2580

ccccaacact tacttcattg tgggcacagc aatggtgtat cctgaagagg cagagcccaa   2640

gcagggtcgc attgtggtct ttcagtattc ggatggaaaa ctacagactg tggctgaaaa   2700

ggaagtgaaa ggggccgtgt actctatggt ggaatttaac gggaagctgt tagccagcat   2760

caatagcacg gtgcggctct atgagtggac aacagagaag gacgtgcgca ctgagtgcaa   2820

ccactacaac aacatcatgg ccctctacct gaagaccaag ggcgacttca tcctggtggg   2880

cgaccttatg cgctcagtgc tgctgcttgc ctacaagccc atggaaggaa actttgaaga   2940

gattgctcga gactttaatc ccaactggat gagtgctgtg gaaatcttgg atgatgacaa   3000

ttttctgggg gctgaaaatg cctttaactt gtttgtgtgt caaaaggata gcgctgccac   3060

cactgacgag gagcggcagc acctccagga ggttggtctt ttccacctgg gcgagtttgt   3120

caatgtcttt tgccacggct ctctggtaat gcagaatctg ggtgagactt ccacccccac   3180

acaaggctcg gtgctcttcg gcacggtcaa cggcatgata gggctggtga cctcactgtc   3240

agagagctgg tacaacctcc tgctggacat gcagaatcga ctcaataaag tcatcaaaag   3300

tgtggggaag atcgagcact ccttctggag atcctttcac accgagcgga agacagaacc   3360

agccacaggt ttcatcgacg gtgacttgat tgagagtttc ctggatatta gccgccccaa   3420

gatgcaggag gtggtggcaa acctacagta tgacgatggc agcggtatga agcgagaggc   3480

cactgcagac gacctcatca aggttgtgga ggagctaact cggatccatt agccaagggc   3540

agggggcccc tttgctgacc ctccccaaag gctttgccct gctgccctcc ccctcctctc   3600

caccatcgtc ttcttggcca tgggaggcct ttccctaagc cagctgcccc cagagccaca   3660

gttcccctat gtggaagtgg ggcgggcttc atagagactt gggaatgagc tgaaggtgaa   3720

acattttctc cctggatttt taccagtctc acatgattcc agccatcacc ttagaccacc   3780

aagccttgat tggtgttgcc agttgtcctc cttccgggga aggattttgc agttctttgg   3840

ctgaaaggaa gctgtgcgtg tgtgtgtgtg tatgtgtgtg tgtgtatgtg tatctcacac   3900

tcatgcattg tcctcttttt atttagattg gcagtgtagg gagttgtggg tagtggggaa   3960

gagggttagg agggtttcat tgtctgtgaa gtgagacctt ccttttactt ttcttctatt   4020

gcctctgaga gcatcaggcc tagaggcctg actgccaagc catgggtagc ctgggtgtaa   4080

aacctggaga tggtggatga tccccacgcc acagcccttt tgtctctgca aactgccttc   4140

ttcggaaaga agaaggtggg aggatgtgaa ttgttagttt ctgagtttta ccaaataaag   4200

tagaatataa gaagaaaaaa a                                             4221
```

```
<210> SEQ ID NO 23
<211> LENGTH: 269
<212> TYPE: PRT
<213> ORGANISM: Escherichia coli

<400> SEQUENCE: 23

Met Pro Glu Leu Pro Glu Val Glu Thr Ser Arg Arg Gly Ile Glu Pro
  1               5                  10                  15

His Leu Val Gly Ala Thr Ile Leu His Ala Val Val Arg Asn Gly Arg
             20                  25                  30
```

-continued

```
Leu Arg Trp Pro Val Ser Glu Glu Ile Tyr Arg Leu Ser Asp Gln Pro
        35                  40                  45

Val Leu Ser Val Gln Arg Arg Ala Lys Tyr Leu Leu Leu Glu Leu Pro
    50                  55                  60

Glu Gly Trp Ile Ile Ile His Leu Gly Met Ser Gly Ser Leu Arg Ile
 65                  70                  75                  80

Leu Pro Glu Glu Leu Pro Pro Glu Lys His Asp His Val Asp Leu Val
                85                  90                  95

Met Ser Asn Gly Lys Val Leu Arg Tyr Thr Asp Pro Arg Arg Phe Gly
            100                 105                 110

Ala Trp Leu Trp Thr Lys Glu Leu Glu Gly His Asn Val Leu Thr His
        115                 120                 125

Leu Gly Pro Glu Pro Leu Ser Asp Asp Phe Asn Gly Glu Tyr Leu His
    130                 135                 140

Gln Lys Cys Ala Lys Lys Lys Thr Ala Ile Lys Pro Trp Leu Met Asp
145                 150                 155                 160

Asn Lys Leu Val Val Gly Val Gly Asn Ile Tyr Ala Ser Glu Ser Leu
                165                 170                 175

Phe Ala Ala Gly Ile His Pro Asp Arg Leu Ala Ser Ser Leu Ser Leu
            180                 185                 190

Ala Glu Cys Glu Leu Leu Ala Arg Val Ile Lys Ala Val Leu Leu Arg
        195                 200                 205

Ser Ile Glu Gln Gly Gly Thr Thr Leu Lys Asp Phe Leu Gln Ser Asp
    210                 215                 220

Gly Lys Pro Gly Tyr Phe Ala Gln Glu Leu Gln Val Tyr Gly Arg Lys
225                 230                 235                 240

Gly Glu Pro Cys Arg Val Cys Gly Thr Pro Ile Val Ala Thr Lys His
                245                 250                 255

Ala Gln Arg Ala Thr Phe Tyr Cys Arg Gln Cys Gln Lys
            260                 265
```

<210> SEQ ID NO 24
<211> LENGTH: 1093
<212> TYPE: DNA
<213> ORGANISM: Escherichia coli

<400> SEQUENCE: 24

```
gatctacaaa gaagcgaaaa tcaaataatt ctcgctttga tgtaacaaaa aaacctcgct     60

ccggcggggt ttttgttatc tgcttgcccc catattgact gcatctgttc attcctggag    120

atgctatgcc tgaattaccc gaagttgaaa ccagccgccg cggcatagaa ccgcatctcg    180

ttggtgcaac cattcttcat gcagtggtgc gcaacggacg cttgcgctgg ccggtttcag    240

aagagatcta ccgtttaagc gaccaaccag tgcttagcgt gcagcggcgg gctaaatatc    300

tgctgctgga gctgcctgag ggctggatta tcattcattt agggatgtct ggcagcctgc    360

gcatccttcc agaagaactt ccccctgaaa agcatgacca tgtggatttg gtgatgagca    420

acggcaaagt gctgcgctac accgatccgc gccgctttgg tgcctggctg tggaccaaag    480

agctggaagg gcataatgtg ctgacccatc ttggaccgga gccgcttagc gacgatttca    540

atggtgagta tctgcatcag aagtgcgcga agaaaaaaac ggcgattaaa ccgtggctga    600

tggataacaa gctggtggta ggggtaggga atatctatgc cagcgaatca ctgtttgcgg    660

cggggatcca tccggatcgg ctggcgtcat cactgtcgct ggcagagtgt gaattgttag    720

ctcgggtgat taaagcggtg ttgctgcgtt cgattgagca gggtggtaca acgctgaaag    780
```

-continued

```
atttctgca aagtgatggt aaaccgggct atttcgctca ggaattgcag gtttacgggc    840

gaaaaggtga gccgtgtcgg gtgtgcggta cgccgattgt ggcgactaaa catgcgcagc    900

gggcaacgtt ttattgtcgg cagtgccaga agtaattcat gcgcgccgga tggcatacca    960

tccggcataa acgctacgct aacttcgcca tcagcgcctg atggacattc tccggcagga   1020

aatgggtgac atcgccctga tggcgcgcca cctctttcac caacgatgaa gagataaacg   1080

accactcttt cga                                                        1093
```

<210> SEQ ID NO 25
<211> LENGTH: 211
<212> TYPE: PRT
<213> ORGANISM: Escherichia coli

<400> SEQUENCE: 25

```
Met Asn Lys Ala Lys Arg Leu Glu Ile Leu Thr Arg Leu Arg Glu Asn
  1               5                  10                  15

Asn Pro His Pro Thr Thr Glu Leu Asn Phe Ser Ser Pro Phe Glu Leu
             20                  25                  30

Leu Ile Ala Val Leu Leu Ser Ala Gln Ala Thr Asp Val Ser Val Asn
         35                  40                  45

Lys Ala Thr Ala Lys Leu Tyr Pro Val Ala Asn Thr Pro Ala Ala Met
     50                  55                  60

Leu Glu Leu Gly Val Glu Gly Val Lys Thr Tyr Ile Lys Thr Ile Gly
 65                  70                  75                  80

Leu Tyr Asn Ser Lys Ala Glu Asn Ile Ile Lys Thr Cys Arg Ile Leu
                 85                  90                  95

Leu Glu Gln His Asn Gly Glu Val Pro Glu Asp Arg Ala Ala Leu Glu
            100                 105                 110

Ala Leu Pro Gly Val Gly Arg Lys Thr Ala Asn Val Val Leu Asn Thr
        115                 120                 125

Ala Phe Gly Trp Pro Thr Ile Ala Val Asp Thr His Ile Phe Arg Val
    130                 135                 140

Cys Asn Arg Thr Gln Phe Ala Pro Gly Lys Asn Val Glu Gln Val Glu
145                 150                 155                 160

Glu Lys Leu Leu Lys Val Val Pro Ala Glu Phe Lys Val Asp Cys His
                165                 170                 175

His Trp Leu Ile Leu His Gly Arg Tyr Thr Cys Ile Ala Arg Lys Pro
            180                 185                 190

Arg Cys Gly Ser Cys Ile Ile Glu Asp Leu Cys Glu Tyr Lys Glu Lys
        195                 200                 205

Val Asp Ile
    210
```

<210> SEQ ID NO 26
<211> LENGTH: 780
<212> TYPE: DNA
<213> ORGANISM: Escherichia coli

<400> SEQUENCE: 26

```
acctgattga tgaaagaatg aaaaagcgcc gtgctgaagc agctgcagaa cgtgcattgc     60

caacggtgaa acagggaatg tctgatgaat aaagcaaaac gcctggagat cctcactcgc    120

ctgcgtgaga acaatcctca tcccaccacc gagcttaatt tcagttcgcc ttttgaattg    180

ctgattgccg tactgctttc cgctcaggcg accgatgtca gtgttaataa ggcgacggcg    240

aaactctacc cggtggcgaa tacgcctgca gcgatgcttg aactgggcgt tgaaggggtg    300
```

-continued

```
aaaacctata tcaaaacgat tgggctttat aacagcaaag cagaaaatat catcaaaacc    360

tgccgtatct tgctggagca gcataatggc gaggttccgg aagatcgtgc tgcgcttgaa    420

gccctgcccg gcgtaggtcg taaaacagcc aacgtcgtat taaacactgc attcggctgg    480

ccgactattg ctgtcgacac gcacattttc cgcgtttgta atcgtactca atttgccccg    540

gggaaaaacg tcgaacaggt agaagaaaag ctactgaaag tggttccagc agagtttaaa    600

gtcgactgcc accattggtt gatcctgcac gggcgttata cctgcattgc ccgcaagccc    660

cgctgtggct cttgtattat tgaagatctt tgtgaataca aagagaaagt tgacatctga    720

agaaaagggg taacaccgat taccccattg ataacctttc tttatcctct tttaaaacat    780
```

<210> SEQ ID NO 27
<211> LENGTH: 263
<212> TYPE: PRT
<213> ORGANISM: Escherichia coli

<400> SEQUENCE: 27

```
Met Pro Glu Gly Pro Glu Ile Arg Arg Ala Ala Asp Asn Leu Glu Ala
  1               5                  10                  15

Ala Ile Lys Gly Lys Pro Leu Thr Asp Val Trp Phe Ala Phe Pro Gln
             20                  25                  30

Leu Lys Pro Tyr Gln Ser Gln Leu Ile Gly Gln His Val Thr His Val
        35                  40                  45

Glu Thr Arg Gly Lys Ala Leu Leu Thr His Phe Ser Asn Asp Leu Thr
     50                  55                  60

Leu Tyr Ser His Asn Gln Leu Tyr Gly Val Trp Arg Val Val Asp Thr
 65                  70                  75                  80

Gly Glu Glu Pro Gln Thr Thr Arg Val Leu Arg Val Lys Leu Gln Thr
                 85                  90                  95

Ala Asp Lys Thr Ile Leu Leu Tyr Ser Ala Ser Asp Ile Glu Met Leu
            100                 105                 110

Thr Pro Glu Gln Leu Thr Thr His Pro Phe Leu Gln Arg Val Gly Pro
        115                 120                 125

Asp Val Leu Asp Pro Asn Leu Thr Pro Glu Val Val Lys Glu Arg Leu
    130                 135                 140

Leu Ser Pro Arg Phe Arg Asn Arg Gln Phe Ala Gly Leu Leu Leu Asp
145                 150                 155                 160

Gln Ala Phe Leu Ala Gly Leu Gly Asn Tyr Leu Arg Val Glu Ile Leu
                165                 170                 175

Trp Gln Val Gly Leu Thr Gly Asn His Lys Ala Lys Asp Leu Asn Ala
            180                 185                 190

Ala Gln Leu Asp Ala Leu Ala His Ala Leu Leu Glu Ile Pro Arg Phe
        195                 200                 205

Ser Tyr Ala Thr Arg Gly Gln Val Asp Glu Asn Lys His His Gly Ala
    210                 215                 220

Leu Phe Arg Phe Lys Val Phe His Arg Asp Gly Glu Pro Cys Glu Arg
225                 230                 235                 240

Cys Gly Ser Ile Ile Glu Lys Thr Thr Leu Ser Ser Arg Pro Phe Tyr
                245                 250                 255

Trp Cys Pro Gly Cys Gln His
            260
```

<210> SEQ ID NO 28
<211> LENGTH: 1030

-continued

<212> TYPE: DNA
<213> ORGANISM: Escherichia coli

<400> SEQUENCE: 28
gcctgcatgg cgacggcgag cacgcactgg cgttcgcccg ccgactacgc tctgcatttg 60
ccgaaaaggg gattgttgtc gcagcataac cccgattaat aaagaatgaa aaaaggatat 120
caccatgcct gaaggcccgg agatccgccg tgcagcggat aacctggagg cggcgatcaa 180
aggcaaacca ctaactgatg tctggtttgc cttcccgcag ttaaaacctt atcaatcaca 240
acttatcggt caacacgtta cccatgtgga aacgcgtggt aaggcgttgt taactcattt 300
ttccaacgac ttaacgctct acagccataa tcagctttac ggcgtctggc gcgtggttga 360
taccggcgaa gagccgcaga ccacgcgagt attgcgggta aaactgcaaa cggctgacaa 420
aaccattctg ctttatagcg cctcggatat tgagatgttg accccggaac aactgaccac 480
gcatccgttt ttacaacgcg ttggtcccga tgtgctggat ccgaatctga cgccggaggt 540
ggtgaaagaa cgattattgt cgccgcgctt tcgtaaccgt cagtttgctg gattactgct 600
cgatcaggcg tttctggctg ggcttggcaa ttatttgcgg gtggagatcc tctggcaggt 660
tgggttgact ggaaatcata aagcgaaaga tctcaatgcg gcgcaactgg atgcactcgc 720
acacgcgtta ctggagattc ctcgattttc ctacgctacg cgggggcagg tggatgagaa 780
taagcatcat ggggcgctgt ttcgctttaa ggtttttcat cgagatggcg aaccgtgcga 840
acgttgtggc agcatcattg agaaaaccac gctgtcatct cgcccgtttt actggtgccc 900
tggctgccag cactaggccg accgcttcgg cgcataggtt gaaataaacc gcgcaatggc 960
aggccctgtc agcaaaatac tgaacaggcg tagggtttgc atcgccataa tgagcgccag 1020
acctgcaggc 1030

<210> SEQ ID NO 29
<211> LENGTH: 268
<212> TYPE: PRT
<213> ORGANISM: Escherichia coli

<400> SEQUENCE: 29

Met Lys Phe Val Ser Phe Asn Ile Asn Gly Leu Arg Ala Arg Pro His
1 5 10 15

Gln Leu Glu Ala Ile Val Glu Lys His Gln Pro Asp Val Ile Gly Leu
20 25 30

Gln Glu Thr Lys Val His Asp Asp Met Phe Pro Leu Glu Glu Val Ala
35 40 45

Lys Leu Gly Tyr Asn Val Phe Tyr His Gly Gln Lys Gly His Tyr Gly
50 55 60

Val Ala Leu Leu Thr Lys Glu Thr Pro Ile Ala Val Arg Arg Gly Phe
65 70 75 80

Pro Gly Asp Asp Glu Glu Ala Gln Arg Arg Ile Ile Met Ala Glu Ile
85 90 95

Pro Ser Leu Leu Gly Asn Val Thr Val Ile Asn Gly Tyr Phe Pro Gln
100 105 110

Gly Glu Ser Arg Asp His Pro Ile Lys Phe Pro Ala Lys Ala Gln Phe
115 120 125

Tyr Gln Asn Leu Gln Asn Tyr Leu Glu Thr Glu Leu Lys Arg Asp Asn
130 135 140

Pro Val Leu Ile Met Gly Asp Met Asn Ile Ser Pro Thr Asp Leu Asp
145 150 155 160

-continued

```
Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265


<210> SEQ ID NO 30
<211> LENGTH: 1246
<212> TYPE: DNA
<213> ORGANISM: Escherichia coli

<400> SEQUENCE: 30

gatcattgac gaaatttact ggaaattact gcgccattct gacgcagcgc gcaccaaaag     60

cgggcatttt ttgcgccatc gttgacatca ttaacaacca tcgatcaaat cacttaacaa    120

caggcggtaa gcaacgcgaa attctgctac catccacgca ctctttatct gaataaatgg    180

cagcgactat gaaatttgtc tcttttaata tcaacggcct gcgcgccaga cctcaccagc    240

ttgaagccat cgtcgaaaag caccaaccgg atgtgattgg cctgcaggag acaaaagttc    300

atgacgatat gtttccgctc gaagaggtgg cgaagctcgg ctacaacgtg ttttatcacg    360

ggcagaaagg ccattatggc gtggcgctgc tgaccaaaga gacgccgatt gccgtgcgtc    420

gcggctttcc cggtgacgac gaagaggcgc agcggcggat tattatggcg gaaatcccct    480

cactgctggg taatgtcacc gtgatcaacg gttacttccc gcagggtgaa agccgcgacc    540

atccgataaa attcccggca aaagcgcagt tttatcagaa tctgcaaaac tacctggaaa    600

ccgaactcaa acgtgataat ccggtactga ttatgggcga tatgaatatc agccctacag    660

atctggatat cggcattggc gaagaaaacc gtaagcgctg gctgcgtacc ggtaaatgct    720

ctttcctgcc ggaagagcgc gaatggatgg acaggctgat gagctggggg ttggtcgata    780

ccttccgcca tgcgaatccg caaacagcag atcgtttctc atggtttgat taccgctcaa    840

aaggttttga cgataaccgt ggtctgcgca tcgacctgct gctcgccagc caaccgctgg    900

cagaatgttg cgtagaaacc ggcatcgact atgaaatccg cagcatggaa aaaccgtccg    960

atcacgcccc cgtctgggcg accttccgcc gctaatttag cagctctcct ggctcaaact   1020

gggtcaggag aattaacctt gagaaaaatc aacaaactgt cagtaatgat ttgttgcctg   1080

ccgtcctttg ttataccgtc tctgcgtttt tagttgtctg accacttctc tattatcaag   1140

tttgatatag gaaactccac gatgaacgct gagcgtaaat ttctttttgc ctgtcttatt   1200

tttgcgctgg tcatttacgc tatccacgct ttcggtttat tcgatc                  1246


<210> SEQ ID NO 31
<211> LENGTH: 285
<212> TYPE: PRT
<213> ORGANISM: Escherichia coli

<400> SEQUENCE: 31
```

-continued

```
Met Lys Tyr Ile Gly Ala His Val Ser Arg Ala Gly Gly Leu Ala Asn
  1               5                  10                  15

Ala Ala Ile Arg Ala Ala Glu Ile Asp Ala Thr Ala Phe Ala Leu Phe
             20                  25                  30

Thr Lys Asn Gln Arg Gln Trp Arg Ala Ala Pro Leu Thr Thr Gln Thr
         35                  40                  45

Ile Asp Glu Phe Lys Ala Ala Cys Glu Lys Tyr His Tyr Thr Ser Ala
     50                  55                  60

Gln Ile Leu Pro His Asp Ser Tyr Leu Ile Asn Leu Gly His Pro Val
 65                  70                  75                  80

Thr Glu Ala Leu Glu Lys Ser Arg Asp Ala Phe Ile Asp Glu Met Gln
                 85                  90                  95

Arg Cys Glu Gln Leu Gly Leu Ser Leu Leu Asn Phe His Pro Gly Ser
            100                 105                 110

His Leu Met Gln Ile Ser Glu Glu Asp Cys Leu Ala Arg Ile Ala Glu
        115                 120                 125

Ser Ile Asn Ile Ala Leu Asp Lys Thr Gln Gly Val Thr Ala Val Ile
    130                 135                 140

Glu Asn Thr Ala Gly Gln Gly Ser Asn Leu Gly Phe Lys Phe Glu His
145                 150                 155                 160

Leu Ala Ala Ile Ile Asp Gly Val Glu Asp Lys Ser Arg Val Gly Val
                165                 170                 175

Cys Ile Asp Thr Cys His Ala Phe Ala Ala Gly Tyr Asp Leu Arg Thr
            180                 185                 190

Pro Ala Glu Cys Glu Lys Thr Phe Ala Asp Phe Ala Arg Thr Val Gly
        195                 200                 205

Phe Lys Tyr Leu Arg Gly Met His Leu Asn Asp Ala Lys Ser Thr Phe
    210                 215                 220

Gly Ser Arg Val Asp Arg His His Ser Leu Gly Glu Gly Asn Ile Gly
225                 230                 235                 240

His Asp Ala Phe Arg Trp Ile Met Gln Asp Asp Arg Phe Asp Gly Ile
                245                 250                 255

Pro Leu Ile Leu Glu Thr Ile Asn Pro Asp Ile Trp Ala Glu Glu Ile
            260                 265                 270

Ala Trp Leu Lys Ala Gln Gln Thr Glu Lys Ala Val Ala
        275                 280                 285
```

<210> SEQ ID NO 32
<211> LENGTH: 1020
<212> TYPE: DNA
<213> ORGANISM: Escherichia coli

<400> SEQUENCE: 32

```
catcgcataa accactacat cttgctctgt taaccgctat cattaccgtt ttcctccagc      60

gggtttaaca ggagtcctcg catgaaatac attggagcgc acgttagtcg tgctggcggt     120

ctggcaaatg ccgcaattcg cgccgccgaa atcgacgcaa ccgcgtttgc cttgttcacc     180

aaaaaccaac gtcagtggcg tgccgcaccg ctcacgacgc aaaccatcga tgaattcaaa     240

gccgcctgtg aaaaatatca ctacacatcg gcgcaaattc ttccccacga cagttatctg     300

attaacctcg gacatccggt cactgaagct ctggaaaaat cgcgcgatgc ctttatagat     360

gaaatgcagc gttgcgaaca gctggggctt tctttgctca acttccaccc tggcagccat     420

ctgatgcaga tttcagaaga ggattgcctt gcgcgtattg ccgaatccat caacattgcg     480

ctggataaaa ctcaaggtgt gacagcggtg atagaaaaca ccgccggtca gggcagtaac     540
```

-continued ttagggttta aattcgaaca tctcgcggcg attatcgacg gcgtggaaga taaatcccgc 600
gtcggcgtct gcattgatac ctgccatgct ttcgctgccg ggtatgattt gcgtactcca 660
gccgaatgcg agaaaacatt cgcggatttt gcccgtactg tcggctttaa gtatctgcgc 720
gggatgcacc ttaacgatgc gaaaagcacc tttggcagcc gcgttgaccg ccatcatagc 780
ctcggtgaag gcaatatcgg tcatgatgcg ttccgctgga tcatgcagga cgaccgtttc 840
gacggcattc cgctgatcct cgaaaccatc aacccggata tctgggcaga agagatcgcc 900
tggctgaaag cgcaacaaac tgaaaaagcg gtagcctgaa gatgaataac cgggaaaagg 960
agatccttgc aattttacgg cgtaacccgc tgattcagca gaacgaaatt gcggacatgc 1020

<210> SEQ ID NO 33
<211> LENGTH: 138
<212> TYPE: PRT
<213> ORGANISM: Artificial Sequence
<220> FEATURE:
<223> OTHER INFORMATION: Description of Artificial Sequence:Synthetic gene

<400> SEQUENCE: 33

Met Thr Arg Ile Asn Leu Thr Leu Val Ser Glu Leu Ala Asp Gln His
1 5 10 15

Leu Met Ala Glu Tyr Arg Glu Leu Pro Arg Val Phe Gly Ala Val Arg
20 25 30

Lys His Val Ala Asn Gly Lys Arg Val Arg Asp Phe Lys Ile Ser Pro
35 40 45

Thr Phe Ile Leu Gly Ala Gly His Val Thr Phe Phe Tyr Asp Lys Leu
50 55 60

Glu Phe Leu Arg Lys Arg Gln Ile Glu Leu Ile Ala Glu Cys Leu Lys
65 70 75 80

Arg Gly Phe Asn Ile Lys Asp Thr Thr Val Gln Asp Ile Ser Asp Ile
85 90 95

Pro Gln Glu Phe Arg Gly Asp Tyr Ile Pro His Glu Ala Ser Ile Ala
100 105 110

Ile Ser Gln Ala Arg Leu Asp Glu Lys Ile Ala Gln Arg Pro Thr Trp
115 120 125

Tyr Lys Tyr Tyr Gly Lys Ala Ile Tyr Ala
130 135

<210> SEQ ID NO 34
<211> LENGTH: 424
<212> TYPE: DNA
<213> ORGANISM: Artificial Sequence
<220> FEATURE:
<223> OTHER INFORMATION: Description of Artificial Sequence:Synthetic gene

<400> SEQUENCE: 34
cgatatgacg cgtatcaacc ttactttagt atccgagtta gctgaccaac acttaatggc 60
tgaataccgt gaattgccgc gtgtttttgg tgcagttcgt aagcacgtag caaacggtaa 120
acgtgttcgt gacttcaaaa tcagtcctac ttttatcctt ggcgcaggtc atgttacatt 180
cttctacgat aagctcgagt tcttacgcaa gcgtcaaatt gagcttatag ctgaatgttt 240
gaaacgtggc ttcaatatca aggatactac agtccaggac atcagtgaca ttcctcaaga 300
attccgtggt gattatattc cccatgaagc ttctattgct atatcacaag ctcgtttaga 360
tgaaaaaatt gcacaacgtc ctacttggta caaatactac ggtaaggcga tttatgcatg 420

-continued atag 424

<210> SEQ ID NO 35
<211> LENGTH: 229
<212> TYPE: PRT
<213> ORGANISM: Escherichia coli

<400> SEQUENCE: 35

Met Ala Asn Glu Leu Thr Trp His Asp Val Leu Ala Glu Glu Lys Gln
1 5 10 15

Gln Pro Tyr Phe Leu Asn Thr Leu Gln Thr Val Ala Ser Glu Arg Gln
20 25 30

Ser Gly Val Thr Ile Tyr Pro Pro Gln Lys Asp Val Phe Asn Ala Phe
35 40 45

Arg Phe Thr Glu Leu Gly Asp Val Lys Val Val Ile Leu Gly Gln Asp
50 55 60

Pro Tyr His Gly Pro Gly Gln Ala His Gly Leu Ala Phe Ser Val Arg
65 70 75 80

Pro Gly Ile Ala Ile Pro Pro Ser Leu Leu Asn Met Tyr Lys Glu Leu
85 90 95

Glu Asn Thr Ile Pro Gly Phe Thr Arg Pro Asn His Gly Tyr Leu Glu
100 105 110

Ser Trp Ala Arg Gln Gly Val Leu Leu Leu Asn Thr Val Leu Thr Val
115 120 125

Arg Ala Gly Gln Ala His Ser His Ala Ser Leu Gly Trp Glu Thr Phe
130 135 140

Thr Asp Lys Val Ile Ser Leu Ile Asn Gln His Arg Glu Gly Val Val
145 150 155 160

Phe Leu Leu Trp Gly Ser His Ala Gln Lys Lys Gly Ala Ile Ile Asp
165 170 175

Lys Gln Arg His His Val Leu Lys Ala Pro His Pro Ser Pro Leu Ser
180 185 190

Ala His Arg Gly Phe Phe Gly Cys Asn His Phe Val Leu Ala Asn Gln
195 200 205

Trp Leu Glu Gln Arg Gly Glu Thr Pro Ile Asp Trp Met Pro Val Leu
210 215 220

Pro Ala Glu Ser Glu
225

<210> SEQ ID NO 36
<211> LENGTH: 1532
<212> TYPE: DNA
<213> ORGANISM: Escherichia coli

<400> SEQUENCE: 36
gttaacgttc aggtgttgac caccttcaac gcgaacttct ggtttcactt ctactggaac 60
ttcacggtat tcaatgtcac ccagtttgct tactgcaacc acttcatctt ctgcataacc 120
tgcttttgca acgatgcaac gcgcttcgcc tttttcgctg tccagcagcc agaaagagtt 180
cagcagatcg tcgttagcgg ctttagtaat ctggatacct gtaatcatgt gatgcctccc 240
cggcaaaatt atttgatttg ttcagcctgt cgcggccaat tggtaaaacc attgttgctt 300
gagtgtatat atactcctca aacacccttg aatctttgat ttaaatcaat aaaaaccaca 360
catcaagtat ggtcgcaaat ggattttatt gttttacatc aacttatgcg ggtgtgaaat 420
tttaccaatt tacatttttt tgcactcgtt taagtctaaa aaatgagcat gattttgttc 480

-continued

```
tgtagaaaga agcagttaag ctaggcggat tgaagattcg caggagagcg agatggctaa    540

cgaattaacc tggcatgacg tgctggctga agagaagcag caaccctatt ttcttaatac    600

ccttcagacc gtcgccagcg agcggcagtc cggcgtcact atctacccac cacaaaaaga    660

tgtctttaac gcgttccgct ttacagagtt gggtgacgtt aaagtggtga ttctcggcca    720

ggatccttat cacggaccgg gacaggcgca tggtctggca ttttccgttc gtcccggcat    780

tgccattcct ccgtcattat tgaatatgta taaagagctg gaaaatacta ttccgggctt    840

cacccgccct aatcatggtt atcttgaaag ctgggcgcgt cagggcgttc tgctactcaa    900

tactgtgttg acggtacgcg caggtcaggc gcattcccac gccagcctcg gctgggaaac    960

cttcaccgat aaagtgatca gcctgattaa ccagcatcgc gaaggcgtgg tgtttttgtt   1020

gtggggatcg catgcgcaaa agaaaggggc gattatagat aagcaacgcc atcatgtact   1080

gaaagcaccg catccgtcgc cgctttcggc gcatcgtgga ttctttggct gcaaccattt   1140

tgtgctggca aatcagtggc tggaacaacg tggcgagacg ccgattgact ggatgccagt   1200

attaccggca gagagtgagt aaatttgcgg ggaaatgccg gatggcagag ttgccacccg   1260

gctgatttat caggctttat tctgacgcca ccattcacca agcaaaacgc cggttgcgac   1320

agagatattc agcccggcaa cgttgcccgt accgtcaatc ttcacgcgca gatcgttcgg   1380

atcgcgtgcg gcatccggta acccttcata ttcctgaccc agcaccagta ccatttttcgc  1440

tggcagacta gttttgaaca gcggtttacc ctgctcgctg gaagtggtca ctacggtgta   1500

acctgctgac ggaaatcatc cagcacgtta ac                                 1532
```

<210> SEQ ID NO 37
<211> LENGTH: 350
<212> TYPE: PRT
<213> ORGANISM: Escherichia coli

<400> SEQUENCE: 37

```
Met Gln Ala Ser Gln Phe Ser Ala Gln Val Leu Asp Trp Tyr Asp Lys
  1               5                  10                  15

Tyr Gly Arg Lys Thr Leu Pro Trp Gln Ile Asp Lys Thr Pro Tyr Lys
             20                  25                  30

Val Trp Leu Ser Glu Val Met Leu Gln Gln Thr Gln Val Ala Thr Val
         35                  40                  45

Ile Pro Tyr Phe Glu Arg Phe Met Ala Arg Phe Pro Thr Val Thr Asp
     50                  55                  60

Leu Ala Asn Ala Pro Leu Asp Glu Val Leu His Leu Trp Thr Gly Leu
 65                  70                  75                  80

Gly Tyr Tyr Ala Arg Ala Arg Asn Leu His Lys Ala Ala Gln Gln Val
                 85                  90                  95

Ala Thr Leu His Gly Gly Lys Phe Pro Glu Thr Phe Glu Glu Val Ala
            100                 105                 110

Ala Leu Pro Gly Val Gly Arg Ser Thr Ala Gly Ala Ile Leu Ser Leu
        115                 120                 125

Ser Leu Gly Lys His Phe Pro Ile Leu Asp Gly Asn Val Lys Arg Val
    130                 135                 140

Leu Ala Arg Cys Tyr Ala Val Ser Gly Trp Pro Gly Lys Lys Glu Val
145                 150                 155                 160

Glu Asn Lys Leu Trp Ser Leu Ser Glu Gln Val Thr Pro Ala Val Gly
                165                 170                 175

Val Glu Arg Phe Asn Gln Ala Met Met Asp Leu Gly Ala Met Ile Cys
```

-continued

```
            180                 185                 190

Thr Arg Ser Lys Pro Lys Cys Ser Leu Cys Pro Leu Gln Asn Gly Cys
        195                 200                 205

Ile Ala Ala Ala Asn Asn Ser Trp Ala Leu Tyr Pro Gly Lys Lys Pro
    210                 215                 220

Lys Gln Thr Leu Pro Glu Arg Thr Gly Tyr Phe Leu Leu Leu Gln His
225                 230                 235                 240

Glu Asp Glu Val Leu Leu Ala Gln Arg Pro Pro Ser Gly Leu Trp Gly
                245                 250                 255

Gly Leu Tyr Cys Phe Pro Gln Phe Ala Asp Glu Glu Ser Leu Arg Gln
            260                 265                 270

Trp Leu Ala Gln Arg Gln Ile Ala Ala Asp Asn Leu Thr Gln Leu Thr
        275                 280                 285

Ala Phe Arg His Thr Phe Ser His Phe His Leu Asp Ile Val Pro Met
    290                 295                 300

Trp Leu Pro Val Ser Ser Phe Thr Gly Cys Met Asp Glu Gly Asn Ala
305                 310                 315                 320

Leu Trp Tyr Asn Leu Ala Gln Pro Pro Ser Val Gly Leu Ala Ala Pro
                325                 330                 335

Val Glu Arg Leu Leu Gln Gln Leu Arg Thr Gly Ala Pro Val
            340                 345                 350


<210> SEQ ID NO 38
<211> LENGTH: 2293
<212> TYPE: DNA
<213> ORGANISM: Escherichia coli

<400> SEQUENCE: 38

agcttgcatg cagatcagac cttcccaggc cagataaccg ctgccgtcaa aggccagttt      60

gttcggttcg ataacctcgt taataaaatc atcaacggtt ttatcaatct gttcttccga     120

tgtaccttcc gggaatcgcc atgccaccga aaatcctaat tcctggaatt cgtcgatgtg     180

catttttttta cgcagacgac ggctacggtt ctttgccatt atttcaccct ctcgaacatt     240

aagtcccata ctccgtgacc aagacgatga ccacgttgtt caaatttcgt caccggacgt     300

gatgccggac gcggtacgta atcattgctc tctgacaggt ttttataacc gtcaatagaa     360

gacatcactt caagcatatg ttccgcataa ggttcccagt cggtcgccat atggaatacg     420

ccccccagct gcagtttgct ttttaccagt tcggcaaacg gcacctgaac gatacggcgt     480

ttattatggc gcgctttgtg ccacgggtca gggaaaaaga gctgcaccat gcgcaatgaa     540

ttgtcaggaa tcattttatg cagcacttca accgcatcgt gacacatcac gcgcaggttg     600

cttaaacctt cttcatgcgc agaagccagg cacgcaccaa cgcccggtga atgcacttca     660

atgccgagga agtcctgctc agggcgatct ttagccattg ccaccagcga cgcccccatg     720

ccaaaaccaa tctcaagcgt caccggcgct tcacggccaa aaagcgcggg gaaatccagc     780

atatcttcgc tgaactcaac gcccatcacc ggccagtagt tttccagcgc atgttcctgg     840

cctttggtca gtcggcccct ggcggcgcac aaaactacgg atacggcgca gtgggcggcc     900

gttttcatca aattccggtg aaatgacgtc gtttttcata aaggtttagt cgcttgtgaa     960

agtgttctga aaacgggcat tatccaaagt tagttgccgg atgcaagcat gataaggccg    1020

tggctgcgga aagttccggt ttacaccctg ccgtcgctgt gctgcaatct tgcccccaac    1080

aacagtgaat tcggtgacca tgcaagcgtc gcaattttca gcccaggttc tggactggta    1140

cgataaatac gggcgaaaaa ctctgccctg gcaaattgac aagacgccct acaaagtatg    1200
```

-continued

```
gctctcagaa gtgatgttgc aacaaactca ggttgcgacc gttatcccct attttgaacg   1260

ctttatggcg cgcttcccga cggtgaccga tctcgccaat gcgccgctcg acgaagttct   1320

ccacttgtgg accgggcttg gctattacgc ccgcgcgcgc aatctgcata aagcggcaca   1380

acaagtggcg accttacacg gcggtaaatt cccggaaacc tttgaggaag ttgcagcact   1440

gccgggcgtc gggcgttcca ccgcaggcgc gattctctcg ctttctctgg gtaagcactt   1500

tccgattctc gacggtaacg tcaaacgcgt gctggcgcgc tgctatgctg taagcggctg   1560

gcctgggaaa aaagaggtcg agaataaatt atggagtttg agcgagcagg tgacgcccgc   1620

ggttggcgtg gaacggttta atcaggcgat gatggatttg ggtgcgatga tttgtacgcg   1680

ctcgaaaccg aaatgttcgc tctgtccgct acaaaacgga tgtattgccg ccgccaacaa   1740

tagctgggcg ctttatccgg gcaaaaaacc gaaacagacg ctgccggagc gcaccggcta   1800

ctttttgcta ttacagcacg aagatgaagt attgctggcg cagcgtccgc cgagcggatt   1860

gtggggcggt ttatactgtt tcccgcagtt tgccgacgaa gaaagtttgc ggcagtggct   1920

ggcgcaacgg cagattgctg ccgataacct gacgcaactg accgcgtttc ggcatacctt   1980

cagccatttc cacttagata ttgtgcctat gtggcttccc gtgtcgtcat tcaccggctg   2040

catggatgaa ggcaatgcgc tctggtataa cttagcgcaa ccgccgtcag ttggcctagc   2100

ggctcccgtg gagcgtttgt tacagcagtt acgcactggc gcgccggttt agcgcgtgag   2160

tcgataaaga ggatgattta tgagcagaac gattttttgt actttcctgc aacgtgaagc   2220

agaaggtcag gattttcagc tgtaccccgg cgagctggga aaacgcatct ataacgagat   2280

cctctacgcg acg                                                      2293
```

```
<210> SEQ ID NO 39
<211> LENGTH: 138
<212> TYPE: PRT
<213> ORGANISM: Artificial Sequence
<220> FEATURE:
<223> OTHER INFORMATION: Description of Artificial Sequence:Synthetic
      gene

<400> SEQUENCE: 39

Met Thr Arg Ile Asn Leu Thr Leu Val Ser Glu Leu Ala Asp Gln His
  1               5                  10                  15

Leu Met Ala Glu Tyr Arg Glu Leu Pro Arg Val Phe Gly Ala Val Arg
             20                  25                  30

Lys His Val Ala Asn Gly Lys Arg Val Arg Asp Phe Lys Ile Ser Pro
         35                  40                  45

Thr Phe Ile Leu Gly Ala Gly His Val Thr Phe Phe Tyr Asp Lys Leu
     50                  55                  60

Glu Phe Leu Arg Lys Arg Gln Ile Glu Leu Ile Ala Glu Cys Leu Lys
 65                  70                  75                  80

Arg Gly Phe Asn Ile Lys Asp Thr Thr Val Gln Asp Ile Ser Asp Ile
                 85                  90                  95

Pro Gln Glu Phe Arg Gly Asp Tyr Ile Pro His Glu Ala Ser Ile Ala
            100                 105                 110

Ile Ser Gln Ala Arg Leu Asp Glu Lys Ile Ala Gln Arg Pro Thr Trp
        115                 120                 125

Tyr Lys Tyr Tyr Gly Lys Ala Ile Tyr Ala
    130                 135

<210> SEQ ID NO 40
```

-continued

<211> LENGTH: 424
<212> TYPE: DNA
<213> ORGANISM: Artificial Sequence
<220> FEATURE:
<223> OTHER INFORMATION: Description of Artificial Sequence:Synthetic gene

<400> SEQUENCE: 40

```
cgatatgacg cgtatcaacc ttactttagt atccgagtta gctgaccaac acttaatggc     60

tgaataccgt gaattgccgc gtgtttttgg tgcagttcgt aagcacgtag caaacggtaa    120

acgtgttcgt gacttcaaaa tcagtcctac ttttatcctt ggcgcaggtc atgttacatt    180

cttctacgat aagctcgagt tcttacgcaa gcgtcaaatt gagcttatag ctgaatgttt    240

gaaacgtggc ttcaatatca aggatactac agtccaggac atcagtgaca ttcctcaaga    300

attccgtggt gattatattc cccatgaagc ttctattgct atatcacaag ctcgtttaga    360

tgaaaaaatt gcacaacgtc ctacttggta caaatactac ggtaaggcga tttatgcatg    420

atag                                                                  424
```

<210> SEQ ID NO 41
<211> LENGTH: 410
<212> TYPE: PRT
<213> ORGANISM: Homo sapiens

<400> SEQUENCE: 41

```
Met Glu Ala Glu Asn Ala Gly Ser Tyr Ser Leu Gln Gln Ala Gln Ala
  1               5                  10                  15

Phe Tyr Thr Phe Pro Phe Gln Gln Leu Met Ala Glu Ala Pro Asn Met
             20                  25                  30

Ala Val Val Asn Glu Gln Gln Met Pro Glu Glu Val Pro Ala Pro Ala
         35                  40                  45

Pro Ala Gln Glu Pro Val Gln Glu Ala Pro Lys Gly Arg Lys Arg Lys
     50                  55                  60

Pro Arg Thr Thr Glu Pro Lys Gln Pro Val Glu Pro Lys Lys Pro Val
 65                  70                  75                  80

Glu Ser Lys Lys Ser Gly Lys Ser Ala Lys Pro Lys Glu Lys Gln Glu
                 85                  90                  95

Lys Ile Thr Asp Thr Phe Lys Val Lys Arg Lys Val Asp Arg Phe Asn
            100                 105                 110

Gly Val Ser Glu Ala Glu Leu Leu Thr Lys Thr Leu Pro Asp Ile Leu
        115                 120                 125

Thr Phe Asn Leu Asp Ile Val Ile Ile Gly Ile Asn Pro Gly Leu Met
    130                 135                 140

Ala Ala Tyr Lys Gly His His Tyr Pro Gly Pro Gly Asn His Phe Trp
145                 150                 155                 160

Lys Cys Leu Phe Met Ser Gly Leu Ser Glu Val Gln Leu Asn His Met
                165                 170                 175

Asp Asp His Thr Leu Pro Gly Lys Tyr Gly Ile Gly Phe Thr Asn Met
            180                 185                 190

Val Glu Arg Thr Thr Pro Gly Ser Lys Asp Leu Ser Ser Lys Glu Phe
        195                 200                 205

Arg Glu Gly Gly Arg Ile Leu Val Gln Lys Leu Gln Lys Tyr Gln Pro
    210                 215                 220

Arg Ile Ala Val Phe Asn Gly Lys Cys Ile Tyr Glu Ile Phe Ser Lys
225                 230                 235                 240

Glu Val Phe Gly Val Lys Val Lys Asn Leu Glu Phe Gly Leu Gln Pro
```

-continued

```
            245                 250                 255

His Lys Ile Pro Asp Thr Glu Thr Leu Cys Tyr Val Met Pro Ser Ser
            260                 265                 270

Ser Ala Arg Cys Ala Gln Phe Pro Arg Ala Gln Asp Lys Val His Tyr
        275                 280                 285

Tyr Ile Lys Leu Lys Asp Leu Arg Asp Gln Leu Lys Gly Ile Glu Arg
    290                 295                 300

Asn Met Asp Val Gln Glu Val Gln Tyr Thr Phe Asp Leu Gln Leu Ala
305                 310                 315                 320

Gln Glu Asp Ala Lys Lys Met Ala Val Lys Glu Glu Lys Tyr Asp Pro
            325                 330                 335

Gly Tyr Glu Ala Ala Tyr Gly Gly Ala Tyr Gly Glu Asn Pro Cys Ser
            340                 345                 350

Ser Glu Pro Cys Gly Phe Ser Ser Asn Gly Leu Ile Glu Ser Val Glu
        355                 360                 365

Leu Arg Gly Glu Ser Ala Phe Ser Gly Ile Pro Asn Gly Gln Trp Met
    370                 375                 380

Thr Gln Ser Phe Thr Asp Gln Ile Pro Ser Phe Ser Asn His Cys Gly
385                 390                 395                 400

Thr Gln Glu Gln Glu Glu Glu Ser His Ala
            405                 410


<210> SEQ ID NO 42
<211> LENGTH: 3410
<212> TYPE: DNA
<213> ORGANISM: Homo sapiens

<400> SEQUENCE: 42

gcaccaggcg cccagtggag ccgtttggga gaattgcctg cgccacgcag cggggccgga     60

caggcggtaa ggatctgatt aggctttcga acttgagttt gactgatgtc ttctgtgtgg    120

tgtccgctaa atcccacagc atataggatc agtcgcattg gttataaggt ttgcttctgg    180

ctgggtgcgg tggctcatgc ctgtaatcca acattgggag gccaaggcag gcggaccacc    240

tgaagtcggg agcttgagtc cagccactgt ctgggtactg ccagccatcg ggcccaggtc    300

tctggggttg tcttaccgca gtgagtacca cgcggtacta cagagaccgg ctgcccgtgt    360

gcccggcagg tggagccgcc gcatcagcgg cctcggggaa tggaagcgga gaacgcgggc    420

agctattccc ttcagcaagc tcaagctttt tatacgtttc catttcaaca actgatggct    480

gaagctccta atatggcagt tgtgaatgaa cagcaaatgc cagaagaagt tccagcccca    540

gctcctgctc aggaaccagt gcaagaggct ccaaaaggaa gaaaaagaaa acccagaaca    600

acagaaccaa aacaaccagt ggaacccaaa aaacctgttg agtcaaaaaa atctggcaag    660

tctgcaaaac caaaagaaaa acaagaaaaa attacagaca catttaaagt aaaaagaaaa    720

gtagaccgtt ttaatggtgt ttcagaagct gaacttctga ccaagactct ccccgatatt    780

ttgaccttca atctggacat tgtcattatt ggcataaacc cgggactaat ggctgcttac    840

aaagggcatc attaccctgg acctggaaac catttttgga agtgtttgtt tatgtcaggg    900

ctcagtgagg tccagctgaa ccatatggat gatcacactc taccagggaa gtatggtatt    960

ggatttacca acatggtgga aaggaccacg cccggcagca aagatctctc cagtaaagaa   1020

tttcgtgaag gaggacgtat tctagtacag aaattacaga aatatcagcc acgaatagca   1080

gtgtttaatg gaaaatgtat ttatgaaatt tttagtaaag aagtttttgg agtaaaggtt   1140

aagaacttgg aatttgggct tcagccccat aagattccag acacagaaac tctctgctat   1200
```

-continued

```
gttatgccat catccagtgc aagatgtgct cagtttcctc gagcccaaga caaagttcat   1260
tactacataa aactgaagga cttaagagat cagttgaaag gcattgaacg aaatatggac   1320
gttcaagagg tgcaatatac atttgaccta cagcttgccc aagaggatgc aaagaagatg   1380
gctgttaagg aagaaaaata tgatccaggt tatgaggcag catatggtgg tgcttacgga   1440
gaaaatccat gcagcagtga accttgtggc ttctcttcaa atgggctaat tgagagcgtg   1500
gagttaagag gagaatcagc tttcagtggc attcctaatg ggcagtggat gacccagtca   1560
tttacagacc aaattccttc ctttagtaat cactgtggaa cacaagaaca ggaagaagaa   1620
agccatgctt aagaatggtg cttctcagct ctgcttaaat gctgcagttt taatgcagtt   1680
gtcaacaagt agaacctcag tttgctaact gaagtgtttt attagtattt tactctagtg   1740
gtgtaattgt aatgtagaac agttgtgtgg tagtgtgaac cgtatgaacc taagtagttt   1800
ggaagaaaaa gtagggtttt tgtatactag cttttgtatt tgaattaatt atcattccag   1860
ctttttatat actatatttc atttatgaag aaattgattt tcttttggga gtcactttta   1920
atctgtaatt ttaaaataca agtctgaata tttatagttg attcttaact gtgcataaac   1980
ctagatatac cattatccct tttataccta agaagggcat gctaataatt accactgtca   2040
aagaggcaaa ggtgttgatt tttgtatata agttaagcct cagtggagtc tcatttgtta   2100
gtttttagtg gtaactaagg gtaaactcag ggttccctga gctatatgca cactcagacc   2160
tctttgcttt accagtggtg tttgtgagtt gctcagtagt aaaaactggc ccttacctga   2220
cagagccctg gctttgacct gctcagccct gtgtgttaat cctctagtag ccaattaact   2280
actctggggt ggcaggttcc agagaatcga gtagaccttt tgccactcat ctgtgtttta   2340
cttgagacat gtaaatatga tagggaagga actgaatttc tccattcata tttataacca   2400
ttctagtttt atcttccttg gctttaagag tgtgccatgg aaagtgataa gaaatgaact   2460
tctaggctaa gcaaaaagat gctggagata tttgatactc tcatttaaac tggtgcttta   2520
tgtacatgag atgtactaaa ataagtaata tagaattttt cttgctaggt aaatccagta   2580
agccaataat tttaaagatt ctttatctgc atcattgctg tttgttacta taaattaaat   2640
gaacctcatg gaaaggttga ggtgtatacc tttgtgattt tctaatgagt tttccatggt   2700
gctacaaata atccagacta ccaggtctgg tagatattaa agctgggtac taagaaatgt   2760
tatttgcatc ctctcagtta ctcctgaata ttctgatttc atacgtaccc agggagcatg   2820
ctgttttgtc aatcaatata aaatatttat gaggtctccc ccacccccag gaggttatat   2880
gattgctctt ctctttataa taagagaaac aaattcttat tgtgaatctt aacatgcttt   2940
ttagctgtgg ctatgatgga ttttattttt tcctaggtca agctgtgtaa aagtcattta   3000
tgttatttaa atgatgtact gtactgctgt ttacatggac gttttgtgcg ggtgctttga   3060
agtgccttgc atcagggatt aggagcaatt aaattatttt ttcacgggac tgtgtaaagc   3120
atgtaactag gtattgcttt ggtatataac tattgtagct ttacaagaga ttgttttatt   3180
tgaatgggga aaataccctt taaattatga cggacatcca ctagagatgg gtttgaggat   3240
tttccaagcg tgtaataatg atgtttttcc taacatgaca gatgagtagt aaatgttgat   3300
atatcctata catgacagtg tgagactttt tcattaaata atattgaaag attttaaaat   3360
tcatttgaaa gtctgatggc ttttacaata aaagatatta agaattgtta              3410
```

<210> SEQ ID NO 43
<211> LENGTH: 24
<212> TYPE: DNA

-continued

```
<213> ORGANISM: Artificial Sequence
<220> FEATURE:
<223> OTHER INFORMATION: Description of Artificial Sequence:PCR Primer

<400> SEQUENCE: 43

ctccatatgg cgccgctgct ggag                                            24


<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 44

actaccagga ctaggaccac taccgttgct ttctaggacc ag                        42


<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 45

ggtagtggtc ctagtcctgg tagtatggcg ccgctgctgg ag                        42


<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 46

ctcgagctct cagttgcttt ctaggaccag                                      30


<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 47

ctccatatgg aatttgatta tgtaatatgc g                                    31


<210> SEQ ID NO 48
<211> LENGTH: 52
<212> TYPE: DNA
<213> ORGANISM: Artificial Sequence
<220> FEATURE:
<223> OTHER INFORMATION: Description of Artificial Sequence:PCR Primer

<400> SEQUENCE: 48

actaccagga ctaggaccac taccaaattt cttctgtttc attttttctc gg             52


<210> SEQ ID NO 49
<211> LENGTH: 49
<212> TYPE: DNA
<213> ORGANISM: Artificial Sequence
<220> FEATURE:
<223> OTHER INFORMATION: Description of Artificial Sequence:PCR Primer

<400> SEQUENCE: 49

ggtagtggtc ctagtcctgg tagtatggaa tttgattatg taatatgcg                 49
```

-continued

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence:PCR Primer

<400> SEQUENCE: 50
ctcgagctct caaaatttct tctgtttcat tttttctcgg 40

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence:PCR Primer

<400> SEQUENCE: 51
ctccatatgt ccaggcatgc ttgtgttg 28

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 52
actaccagga ctaggaccac tacctctttc cagatagcac ttc 43

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 53
ggtagtggtc ctagtcctgg tagttccagg catgcttgtg ttg 43

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence:PCR Primer

<400> SEQUENCE: 54
ctcgagctct catctttcca gatagcactt c 31

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence:PCR Primer

<400> SEQUENCE: 55
ctcccatggg ctttaacaac aagatgttgg ccttggccgc c 41

<210> SEQ ID NO 56
<211> LENGTH: 48
<212> TYPE: DNA
<213> ORGANISM: Artificial Sequence
<220> FEATURE:

-continued

<223> OTHER INFORMATION: Description of Artificial Sequence:PCR Primer

<400> SEQUENCE: 56
actaccagga ctaggaccac taccgttttt gcagcccatc aactccgg 48

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 57
ctccatatgg cgccgctg 18

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence:PCR Primer

<400> SEQUENCE: 58
ctcgagctct caaaatttc 19

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 59
ctccatatgg cgccgctg 18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 60
ctcgagctct catctttc 18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 61
ctccatatgg aatttgat 18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 62
ctcgagctct cagttgct 18

-continued

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 63
ctccatatgt ccaggcat 18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 64
ctcgagctct cagttgct 18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 65
ctcccatggg ctttaaca 18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 66
ctcgagctct catctttc 18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence:PCR Primer

<400> SEQUENCE: 67
ctcccatggg ctttaaca 18

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence:PCR Primer

<400> SEQUENCE: 68
ctcgagctct caaaatttc 19

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 69
ctccatatgg gggggtatgg cggagttaag                             30

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 70
actaccagga ctaggaccac tacccccctt catgctaccc aggggagg         48

<210> SEQ ID NO 71
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 71
ggtagtggtc ctagtcctgg tagtatgggg gggtatggcg gagttaag         48

<210> SEQ ID NO 72
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 72
ctcgtcgact caccccttca tgctacccag ggg                         33

<210> SEQ ID NO 73
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 73
ctccatatgc gctttaacaa caagatgttg gccttggccg cc               42

<210> SEQ ID NO 74
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 74
actaccagga ctaggaccac taccgttttt gcagcccatc aactccgg         48

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 75
ctccatatgg cgccgctgct ggag                                   24

<210> SEQ ID NO 76
<211> LENGTH: 42

-continued

<212> TYPE: DNA
<213> ORGANISM: Artificial Sequence
<220> FEATURE:
<223> OTHER INFORMATION: Description of Artificial Sequence:PCR Primer

<400> SEQUENCE: 76
ggtagtggtc ctagtcctgg tagtgttgct ttctaggacc ag 42

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 77
actaccagga ctaggaccac taccatggcg ccgctgctgg ag 42

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 78
ctcgtcgact cagttgcttt ctaggaccag 30

<210> SEQ ID NO 79
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 79
ctccatatgg gggggtatgg cggagttaag 30

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 80
ctcgtcgact cagttgcttt ctaggaccag ttcc 34

<210> SEQ ID NO 81
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 81
ctccatatgg cgccgctgct ggagtac 27

<210> SEQ ID NO 82
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 82

```
ctcgtcgact caccccttca tgctacccag ggg                                    33

<210> SEQ ID NO 83
<211> LENGTH: 43
<212> TYPE: DNA
<213> ORGANISM: Artificial Sequence
<220> FEATURE:
<223> OTHER INFORMATION: Description of Artificial Sequence:PCR Primer

<400> SEQUENCE: 83

ctccatatgc gctttaacaa caagatgttg gccttggccg ccc                         43

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence:PCR Primer

<400> SEQUENCE: 84

ctcgtcgact caccccttca tgctacccag ggg                                    33

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 85

ctccatatgg cggcggccga cg                                                22

<210> SEQ ID NO 86
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 86

actaccagga ctaggaccac taccgttcat ggccacacat agtacaag                    48

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence:PCR Primer

<400> SEQUENCE: 87

ggtagtggtc ctagtcctgg tagtatggcg gcggccgacg                             40

<210> SEQ ID NO 88
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 88

ctcgagctct cagttcatgg ccacacatag tacaag                                 36

<210> SEQ ID NO 89
<211> LENGTH: 42
<212> TYPE: DNA
<213> ORGANISM: Artificial Sequence
```

-continued

<220> FEATURE:
<223> OTHER INFORMATION: Description of Artificial Sequence:PCR Primer

<400> SEQUENCE: 89
ctccatatgc gctttaacaa caagatgttg gccttggccg cc 42

<210> SEQ ID NO 90
<211> LENGTH: 48
<212> TYPE: DNA
<213> ORGANISM: Artificial Sequence
<220> FEATURE:
<223> OTHER INFORMATION: Description of Artificial Sequence:PCR Primer

<400> SEQUENCE: 90
actaccagga ctaggaccac taccgttttt gcagcccatc aactccgg 48

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence:PCR Primer

<400> SEQUENCE: 91
ctccatatgg cgccgctgct ggag 24

<210> SEQ ID NO 92
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 92
ggtagtggtc ctagtcctgg tagtgttgct ttctaggacc ag 42

<210> SEQ ID NO 93
<211> LENGTH: 42
<212> TYPE: DNA
<213> ORGANISM: Artificial Sequence
<220> FEATURE:
<223> OTHER INFORMATION: Description of Artificial Sequence:PCR Primer

<400> SEQUENCE: 93
actaccagga ctaggaccac taccatggcg ccgctgctgg ag 42

<210> SEQ ID NO 94
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 94
ctcgagctct cagttgcttt ctaggaccag 30

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 95
ctccatatgg cggcggccga cg 22

-continued

<210> SEQ ID NO 96
<211> LENGTH: 34
<212> TYPE: DNA
<213> ORGANISM: Artificial Sequence
<220> FEATURE:
<223> OTHER INFORMATION: Description of Artificial Sequence:PCR Primer

<400> SEQUENCE: 96
ctcgagctct cagttgcttt ctaggaccag ttcc 34

<210> SEQ ID NO 97
<211> LENGTH: 27
<212> TYPE: DNA
<213> ORGANISM: Artificial Sequence
<220> FEATURE:
<223> OTHER INFORMATION: Description of Artificial Sequence:PCR Primer

<400> SEQUENCE: 97
ctccatatgg cgccgctgct ggagtac 27

<210> SEQ ID NO 98
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 98
ctcgagctct cagttcatgg ccacacatag tacaag 36

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 99
ctccatatgc gctttaacaa caagatgttg 30

<210> SEQ ID NO 100
<211> LENGTH: 36
<212> TYPE: DNA
<213> ORGANISM: Artificial Sequence
<220> FEATURE:
<223> OTHER INFORMATION: Description of Artificial Sequence:PCR Primer

<400> SEQUENCE: 100
ctcgagctct cagttcatgg ccacacatag tacaag 36

<210> SEQ ID NO 101
<211> LENGTH: 940
<212> TYPE: PRT
<213> ORGANISM: Escherichia coli

<400> SEQUENCE: 101

Met Asp Lys Ile Glu Val Arg Gly Ala Arg Thr His Asn Leu Lys Asn
1 5 10 15

Ile Asn Leu Val Ile Pro Arg Asp Lys Leu Ile Val Val Thr Gly Leu
20 25 30

Ser Gly Ser Gly Lys Ser Ser Leu Ala Phe Asp Thr Leu Tyr Ala Glu
35 40 45

Gly Gln Arg Arg Tyr Val Glu Ser Leu Ser Ala Tyr Ala Arg Gln Phe
50 55 60

-continued

```
Leu Ser Leu Met Glu Lys Pro Asp Val Asp His Ile Glu Gly Leu Ser
 65                  70                  75                  80

Pro Ala Ile Ser Ile Glu Gln Lys Ser Thr Ser His Asn Pro Arg Ser
                 85                  90                  95

Thr Val Gly Thr Ile Thr Glu Ile His Asp Tyr Leu Arg Leu Leu Phe
            100                 105                 110

Ala Arg Val Gly Glu Pro Arg Cys Pro Asp His Asp Val Pro Leu Ala
        115                 120                 125

Ala Gln Thr Val Ser Gln Met Val Asp Asn Val Leu Ser Gln Pro Glu
    130                 135                 140

Gly Lys Arg Leu Met Leu Leu Ala Pro Ile Ile Lys Glu Arg Lys Gly
145                 150                 155                 160

Glu His Thr Lys Thr Leu Glu Asn Leu Ala Ser Gln Gly Tyr Ile Arg
                165                 170                 175

Ala Arg Ile Asp Gly Glu Val Cys Asp Leu Ser Asp Pro Pro Lys Leu
            180                 185                 190

Glu Leu Gln Lys Lys His Thr Ile Glu Val Val Val Asp Arg Phe Lys
        195                 200                 205

Val Arg Asp Asp Leu Thr Gln Arg Leu Ala Glu Ser Phe Glu Thr Ala
    210                 215                 220

Leu Glu Leu Ser Gly Gly Thr Ala Val Val Ala Asp Met Asp Asp Pro
225                 230                 235                 240

Lys Ala Glu Glu Leu Leu Phe Ser Ala Asn Phe Ala Cys Pro Ile Cys
                245                 250                 255

Gly Tyr Ser Met Arg Glu Leu Glu Pro Arg Leu Phe Ser Phe Asn Asn
            260                 265                 270

Pro Ala Gly Ala Cys Pro Thr Cys Asp Gly Leu Gly Val Gln Gln Tyr
        275                 280                 285

Phe Asp Pro Asp Arg Val Ile Gln Asn Pro Glu Leu Ser Leu Ala Gly
    290                 295                 300

Gly Ala Ile Arg Gly Trp Asp Arg Arg Asn Phe Tyr Tyr Phe Gln Met
305                 310                 315                 320

Leu Lys Ser Leu Ala Asp His Tyr Lys Phe Asp Val Glu Ala Pro Trp
                325                 330                 335

Gly Ser Leu Ser Ala Asn Val His Lys Val Val Leu Tyr Gly Ser Gly
            340                 345                 350

Lys Glu Asn Ile Glu Phe Lys Tyr Met Asn Asp Arg Gly Asp Thr Ser
        355                 360                 365

Ile Arg Arg His Pro Phe Glu Gly Val Leu His Asn Met Glu Arg Arg
    370                 375                 380

Tyr Lys Glu Thr Glu Ser Ser Ala Val Arg Glu Glu Leu Ala Lys Phe
385                 390                 395                 400

Ile Ser Asn Arg Pro Cys Ala Ser Cys Glu Gly Thr Arg Leu Arg Arg
                405                 410                 415

Glu Ala Arg His Val Tyr Val Glu Asn Thr Pro Leu Pro Ala Ile Ser
            420                 425                 430

Asp Met Ser Ile Gly His Ala Met Glu Phe Phe Asn Asn Leu Lys Leu
        435                 440                 445

Ala Gly Gln Arg Ala Lys Ile Ala Glu Lys Ile Leu Lys Glu Ile Gly
    450                 455                 460

Asp Arg Leu Lys Phe Leu Val Asn Val Gly Leu Asn Tyr Leu Thr Leu
465                 470                 475                 480
```

-continued

Ser Arg Ser Ala Glu Thr Leu Ser Gly Gly Glu Ala Gln Arg Ile Arg
485 490 495

Leu Ala Ser Gln Ile Gly Ala Gly Leu Val Gly Val Met Tyr Val Leu
500 505 510

Asp Glu Pro Ser Ile Gly Leu His Gln Arg Asp Asn Glu Arg Leu Leu
515 520 525

Gly Thr Leu Ile His Leu Arg Asp Leu Gly Asn Thr Val Ile Val Val
530 535 540

Glu His Asp Glu Asp Ala Ile Arg Ala Ala Asp His Val Ile Asp Ile
545 550 555 560

Gly Pro Gly Ala Gly Val His Gly Gly Glu Val Val Ala Glu Gly Pro
565 570 575

Leu Glu Ala Ile Met Ala Val Pro Glu Ser Leu Thr Gly Gln Tyr Met
580 585 590

Ser Gly Lys Arg Lys Ile Glu Val Pro Lys Lys Arg Val Pro Ala Asn
595 600 605

Pro Glu Lys Val Leu Lys Leu Thr Gly Ala Arg Gly Asn Asn Leu Lys
610 615 620

Asp Val Thr Leu Thr Leu Pro Val Gly Leu Phe Thr Cys Ile Thr Gly
625 630 635 640

Val Ser Gly Ser Gly Lys Ser Thr Leu Ile Asn Asp Thr Leu Phe Pro
645 650 655

Ile Ala Gln Arg Gln Leu Asn Gly Ala Thr Ile Ala Glu Pro Ala Pro
660 665 670

Tyr Arg Asp Ile Gln Gly Leu Glu His Phe Asp Lys Val Ile Asp Ile
675 680 685

Asp Gln Ser Pro Ile Gly Arg Thr Pro Arg Ser Asn Pro Ala Thr Tyr
690 695 700

Thr Gly Val Phe Thr Pro Val Arg Glu Leu Phe Ala Gly Val Pro Glu
705 710 715 720

Ser Arg Ala Arg Gly Tyr Thr Pro Gly Arg Phe Ser Phe Asn Val Arg
725 730 735

Gly Gly Arg Cys Glu Ala Cys Gln Gly Asp Gly Val Ile Lys Val Glu
740 745 750

Met His Phe Leu Pro Asp Ile Tyr Val Pro Cys Asp Gln Cys Lys Gly
755 760 765

Lys Arg Tyr Asn Arg Glu Thr Leu Glu Ile Lys Tyr Lys Gly Lys Thr
770 775 780

Ile His Glu Val Leu Asp Met Thr Ile Glu Glu Ala Arg Glu Phe Phe
785 790 795 800

Asp Ala Val Pro Ala Leu Ala Arg Lys Leu Gln Thr Leu Met Asp Val
805 810 815

Gly Leu Thr Tyr Ile Arg Leu Gly Gln Ser Ala Thr Thr Leu Ser Gly
820 825 830

Gly Glu Ala Gln Arg Val Lys Leu Ala Arg Glu Leu Ser Lys Arg Gly
835 840 845

Thr Gly Gln Thr Leu Tyr Ile Leu Asp Glu Pro Thr Thr Gly Leu His
850 855 860

Phe Ala Asp Ile Gln Gln Leu Leu Asp Val Leu His Lys Leu Arg Asp
865 870 875 880

Gln Gly Asn Thr Ile Val Val Ile Glu His Asn Leu Asp Val Ile Lys
885 890 895

Thr Ala Asp Trp Ile Val Asp Leu Gly Pro Glu Gly Gly Ser Gly Gly

-continued

```
            900                 905                 910

Gly Glu Ile Leu Val Ser Gly Thr Pro Glu Thr Val Ala Glu Cys Glu
        915                 920                 925

Ala Ser His Thr Ala Arg Phe Leu Lys Pro Met Leu
    930                 935                 940
```

<210> SEQ ID NO 102
<211> LENGTH: 3205
<212> TYPE: DNA
<213> ORGANISM: Escherchia coli

<400> SEQUENCE: 102

```
atgttcgtgt ctcctgaaaa aaatcgttct gaataagtgt aaacgcgcga ttgtaccatt     60
accaatagcg cttttactat gttgtgacct cggttccgcg aaacaaacct ggccagacat    120
tgttacacaa cactccgggt aatgcattcc aatactgtat attcattcag gtcaatttgt    180
gtcataatta accgtttgtg atcgccggta gcaccatgcc accgggcaaa aaagcgttta    240
atccgggaaa ggtgaatgga taagatcgaa gttcggggcg cccgcaccca taatctcaaa    300
aacatcaacc tcgttatccc ccgcgacaag ctcattgtcg tgaccgggct ttcgggttct    360
ggcaaatcct cgctcgcttt cgacacctta tatgccgaag ggcagcgccg ttacgttgaa    420
tccctttccg cctacgcgcg gcagtttctg tcactgatgg aaaagccgga cgtcgatcat    480
attgaggggc tttctcctgc catctcaatt gagcagaaat cgacgtctca taacccgcgt    540
tctacggtgg ggacaatcac cgaaatccac gactatttgc gtttgttatt cgcccgcgtt    600
ggcgagccgc gctgtccgga ccacgacgtc ccgctggcgg cgcaaaccgt cagccagatg    660
gtggataacg tgctgtcgca gccggaaggc aagcgtctga tgctactcgc gccaatcatt    720
aaagagcgca aaggcgaaca caccaaaacg ctggagaacc tggcaagcca gggctacatc    780
cgtgctcgta ttgatggcga agtctgcgat ctttccgatc cgccaaaact ggaactgcaa    840
aagaaacata ccattgaagt ggtggttgat cgcttcaagg tgcgtgacga tcttacccaa    900
cgtcttgccg agtcatttga aaccgcgctg gagctttccg gtggtaccgc ggtagtggcg    960
gatatggacg acccgaaagc ggaagagctg ctgttctccg ccaacttcgc ctgcccaatt   1020
tgcggctaca gtatgcgtga actggagccg cgactgtttt cgtttaacaa cccggcgggg   1080
gcctgcccga cctgcgacgg ccttggcgta cagcaatatt tcgatcctga tcgagtgatc   1140
cagaatccgg aactgtcgct ggctggtggt gcgatccgtg gctgggatcg ccgcaacttc   1200
tattatttcc agatgctgaa atcgctggca gatcactata agttcgacgt cgaagcgccg   1260
tggggcagcc tgagcgcgaa cgtgcataaa gtggtgttgt acggttctgg caaagaaaac   1320
attgaattca aatacatgaa cgatcgtggc gatacctcca ttcgtcgtca tccgttcgaa   1380
ggcgtgctgc ataatatgga gcgccgctat aaagagacgg aatccagcgc ggtacgcgaa   1440
gaattagcca agtttatcag taatcgtccg tgcgccagct gcgaagggac gcgtctgcgt   1500
cgggaagcgc gccacgtgta tgtcgagaat acgccgctgc ctgctatctc cgacatgagc   1560
attggtcatg cgatggaatt cttcaacaat ctcaaactcg caggtcagcg ggcgaagatt   1620
gcagaaaaaa tccttaaaga gatcggcgat cgtctgaaat tcctcgttaa cgtcggcctg   1680
aattacctga cgctttcccg ctcggcagaa acgctttctg gcggtgaagc acagcgtatc   1740
cgtctggcga gccagattgg tgcgggcctg gttggcgtta tgtacgtgct ggacgagccg   1800
tctatcggcc tgcaccagcg tgataacgag cgcctgttgg gtacgcttat ccatctgcgc   1860
gatctcggta ataccgtgat tgtggtggag cacgacgaag acgcaattcg cgccgctgac   1920
```

-continued

```
catgtgatcg acattggccc gggcgcaggt gttcacggcg gtgaagtggt cgcagaaggt   1980
ccgctggaag cgattatggc ggtgccggag tcgttgaccg ggcagtacat gagcggcaaa   2040
cgcaagattg aagtgccgaa gaaacgcgtt ccggcgaatc cggaaaaagt gctgaagctg   2100
acaggcgcac gcggcaacaa cctgaaggac gtgacgctga cgctgccggt gggtctgttt   2160
acctgcatca ccggggtttc aggttccggt aaatcgacgc tgattaacga cacactgttc   2220
ccgattgccc aacgccagtt gaatggggcg accatcgccg aaccagcacc gtatcgcgat   2280
attcaggggc tggagcattt cgataaagtg atcgatatcg accaaagccc aattggtcgt   2340
actccacgtt ctaacccggc gacctatacc ggcgtgttta cgcctgtgcg cgaactgttt   2400
gcgggcgtac cggaatcccg tgcgcgcggc tatacgccgg gacgtttcag ctttaacgtt   2460
cgtggcggac gctgcgaggc ctgtcagggc gatggcgtga tcaaagtgga gatgcacttc   2520
ctgccggata tctacgtgcc gtgcgaccag tgcaaaggta aacgctataa ccgtgaaacg   2580
ctggagatta agtacaaagg caaaaccatc cacgaagtgc tggatatgac catcgaagag   2640
gcgcgtgagt tctttgatgc cgtacctgca ctggcgcgta agctgcaaac gttgatggac   2700
gttggcctga cgtacattcg actggggcag tccgcaacca ccctttcagg cggtgaagcc   2760
cagcgcgtga agctggcgcg tgaactgtca aaacgcggca ccgggcagac gctgtatatt   2820
ctcgacgagc cgaccaccgg tctgcacttc gccgatattc agcaactgct cgacgtactg   2880
cataaactgc gcgatcaggg caacaccatt gtggtgattg agcacaatct cgacgtgatc   2940
aaaaccgctg actggattgt cgacctggga ccagaaggcg gcagtggtgg cggcgagatc   3000
ctcgtctccg gtacgccaga aaccgtcgcg gagtgcgaag catcacacac ggcacgcttc   3060
cttaagccga tgctgtaatc gttaaggccg ctttctgagc ggccttttcc tttcagagtt   3120
gcaccagcaa tttacgtttt tcttccggca gtaaattcac cgcctgctga taagacgcat   3180
ccaccagata atagatttgc gaatc                                         3205
```

```
<210> SEQ ID NO 103
<211> LENGTH: 401
<212> TYPE: PRT
<213> ORGANISM: Escherichia coli

<400> SEQUENCE: 103

Met Ser Lys Lys Asn Ser Ala Lys Ser Gly Asp Ala Arg Arg Gly Asp
  1               5                  10                  15

Gly Ala His Thr Gly Val Thr Gly Ser Gly Lys Thr Thr Ala Asn Val
             20                  25                  30

Ala Asp Arg Thr Met Val Ala Asn Lys Thr Ala Ala Tyr Gly Met Lys
         35                  40                  45

Asn Ala Val Tyr Val Ser Tyr Tyr Asp Tyr Tyr Ala Tyr Val Ser Ser
     50                  55                  60

Asp Thr Lys Asp Ala Ser Val Asn His Met Arg Ser Ala Thr Lys Ala
 65                  70                  75                  80

Met Arg Arg Asp Val Val Val Val Ala Ser Val Ser Ala Tyr Gly Gly
                 85                  90                  95

Asp Asp Tyr Lys Met Met His Thr Val Gly Met Asp Arg Ala Arg Arg
            100                 105                 110

Ala Tyr Ala Arg Asn Asp Ala Arg Gly Thr Arg Val Arg Gly Val Asp
        115                 120                 125

Ala Ser Asp Asp Ala Arg Val Asp Val Arg Ser Asp Thr Gly Val Ser
    130                 135                 140
```

-continued

```
Thr Arg Thr Tyr Lys Thr His Tyr Val Thr Arg Arg Val Ala Met Lys
145                 150                 155                 160

Ala Ala Arg Arg Lys Val Asn Asn Lys Arg Thr Arg Thr Asp Met Met
                165                 170                 175

Asn Gly Tyr Cys Ser Gly Asn Tyr Ser Arg Ser Gly Arg Gly Gly Thr
            180                 185                 190

Asp Tyr Ala Asp Gly Val Val Asp Ser His Val Thr Gly Gly Met Tyr
        195                 200                 205

Arg Gly Asp Arg Ala Arg Lys Thr Val Tyr Gly Arg Ser Ala Asp Asn
    210                 215                 220

Arg Lys Ala Ala Thr Tyr Val Ser Ala Thr Gly Asn Tyr Lys Ser Gly
225                 230                 235                 240

Gly Asp Val Val Asp Val Val Arg Thr Gly Asp Val Arg Val Ala Thr
                245                 250                 255

Val Asp Asp Ser Arg Arg Ala Ala Asn Arg Val Val Thr Thr Thr Lys
            260                 265                 270

Arg Met Ala Asp Thr Tyr His Gly Arg Val Arg Tyr Arg Ser Asp Asp
        275                 280                 285

Thr Val Arg Met Arg Asp Arg Gly Asp Val Val Gly Asn Arg Gly Asp
    290                 295                 300

Met Val Ser Val Ala Asp Ala Asp Lys Gly Arg Ser Arg Ser Thr Gly
305                 310                 315                 320

Arg Ala Ala Arg Asn Val Asn Gly Lys Ala Tyr Gly Asp Lys Thr Ser
                325                 330                 335

Met Ala Lys Ala Gly Thr Arg Arg Arg Lys Lys Tyr Asn His Gly Thr
            340                 345                 350

Gly Asn Lys Lys Val Val Asp Ala Gly Asn Ala Lys Thr Lys Ala Lys
        355                 360                 365

Gly Arg Gly Lys Ser Arg Val Asp Asn Val Met Asp Met Ser Lys Ala
    370                 375                 380

Lys His Gly Met Met His Ala Asn Ala Ala Arg Asp His Arg Ala Ala
385                 390                 395                 400

Ser
```

<210> SEQ ID NO 104
<211> LENGTH: 2605
<212> TYPE: DNA
<213> ORGANISM: Escherchia coli

<400> SEQUENCE: 104

```
cggcggggga taggggctgg acacagttat ccactattcc tgtggataac catgtgtatt      60

agagttagaa aacacgaggc aagcgagaga atacgcggct tgcacgcgaa ttggcgttaa     120

agacggctca aagaaatatc ttttattttt taaccggtta gataaatgca atggcagtca     180

ctgaacaggc atctcttgcc ataaaactgt catcactcat cttgacaaat gttaaaaaag     240

ccgttgcttt ggggataacc cggtaaggcc ggagttttat ctcgccacag agtaaatttt     300

gctcatgatt gacagcggag tttacgctgt atcagaaata ttatggtgat gaactgtttt     360

tttatccagt ataatttgtt gggataatta agtacgacga gtaaaattac atacctgccc     420

gcccaactcc ttcaggtagc gactcatgag taaaccgttc aaactgaatt ccgcttttaa     480

accttctggc gatcagccag aggcgattcg acgtctcgaa gaggggctgg aagatggcct     540

ggcgcaccag acgttacttg gcgtgactgg ctcagggaaa accttcacca ttgccaatgt     600
```

-continued

```
cattgctgac cttcagcgcc caaccatggt acttgcgccc aacaaaacgc tggcggccca    660

gctgtatggc gaaatgaaag agttcttccc ggaaaacgcg gtggaatatt tcgtttccta    720

ctacgactac tatcagccgg aagcctatgt accgagttcc gacactttca ttgagaaaga    780

tgcctcggtt aacgaacata ttgagcagat gcgtttgtcc gccaccaaag cgatgctgga    840

gcggcgtgat gtggttgtgg tggcgtctgt ttccgcgatt tatggtctgg gcgatcctga    900

tttatatctc aagatgatgc tccatctcac ggtcggtatg attatcgatc agcgcgcgat    960

tctgcgccga ctggcggagc tgcaatacgc tcgtaatgat caagcattcc agcgtggtac   1020

tttccgcgtt cgtggcgagg tgatagatat cttcccggca gaatcggatg acattgcact   1080

tcgcgtggaa ctgtttgacg aggaagtgga acgattgtcg ttatttgacc cgctgaccgg   1140

gcagattgtt tccactattc cacgttttac catctacccg aaaacgcact acgtcacacc   1200

gcgcgagcgc atcgtacagg cgatggagga gatcaaagaa gagctggccg ccagacgcaa   1260

agtgctgttg gaaaacaaca aactgctgga agagcagcgg ctgacccagc gtacccagtt   1320

tgatctggag atgatgaacg agctgggcta ctgttcgggg attgaaaact actcgcgctt   1380

cctctccggt cgtggaccgg gtgagccacc gccgacgctg tttgattacc tgcctgccga   1440

tgggctgctg gtcgtcgatg aatctcacgt caccattcca caaattggcg gcatgtatcg   1500

cggtgaccgg gcgcgtaaag agacactggt ggagtacggc ttccgcctgc catcagcgct   1560

ggataaccgt ccgcttaagt ttgaagagtt cgaagcatta gcgccgcaaa ccatctatgt   1620

ttcggcgacg ccgggtaatt acgagctgga aaaatccggc ggcgatgtgg tggatcaggt   1680

ggtgcgtcca accggattgc ttgacccgat tatcgaagtg cggccggtgg cgacacaggt   1740

tgatgatctt ctttcggaga ttcgtcagcg agcggcaatt aacgaacgcg tactggtcac   1800

cacactgacc aagcggatgg cggaagatct taccgaatat ctcgaagaac atggcgagcg   1860

cgtgcgttat cttcgctcag atatcgacac cgtcgaacgt atggagatta tccgcgactt   1920

gcgtctgggt gagttcgacg tgctggtagg gatcaactta ctgcgcgaag gtctggatat   1980

gccggaagtg tcgctggtgg cgatcctcga cgctgacaaa gaaggcttcc tgcgttccga   2040

acgttcgttg atccagacca ttggtcgtgc ggcacgtaac gttaacggta aagcgattct   2100

ctacggcgat aagatcaccc catcaatggc gaaagcgatt ggcgaaaccg aacgtcgccg   2160

tgagaaacag cagaagtaca acgaggaaca cggaattacg ccgcaaggct tgaacaagaa   2220

agtggtcgat atcctggcgc tggggcagaa cattgccaaa accaaagcga agggcagagg   2280

aaaatcgcgc ccgattgttg agccggataa tgtgccgatg gatatgtcgc ctaaagcgtt   2340

gcagcagaaa atccatgagc tggaagggtt gatgatgcaa cacgcgcaga atctggagtt   2400

cgaagaagcg gcgcaaattc gtgaccagtt gcatcagctg cgtgagctgt ttatcgcggc   2460

atcgtaacag gatagcgaag aagactgatg acaaacggaa aacagcctga tgcgctacgc   2520

ttatcaggcc tacattttct ccgcaatata ttgaatttgc gcggtttgta ggccggtaaa   2580

ggcgatcacg ccgcaaatcc ggcat                                         2605
```

<210> SEQ ID NO 105
<211> LENGTH: 218
<212> TYPE: PRT
<213> ORGANISM: Escherichia coli

<400> SEQUENCE: 105

```
Met Ile Asn Val Leu Leu Val Asp Asp His Glu Leu Val Arg Ala Gly
  1               5                  10                  15
```

-continued

```
Ile Arg Arg Ile Leu Glu Asp Ile Lys Gly Ile Lys Val Val Gly Glu
             20                  25                  30

Ala Ser Cys Gly Glu Asp Ala Val Lys Trp Cys Arg Thr Asn Ala Val
         35                  40                  45

Asp Val Val Leu Met Asp Met Ser Met Pro Gly Ile Gly Gly Leu Glu
     50                  55                  60

Ala Thr Arg Lys Ile Ala Arg Ser Thr Ala Asp Val Lys Ile Ile Met
 65                  70                  75                  80

Leu Thr Val His Thr Glu Asn Pro Leu Pro Ala Lys Val Met Gln Ala
                 85                  90                  95

Gly Ala Ala Gly Tyr Leu Ser Lys Gly Ala Ala Pro Gln Glu Val Val
            100                 105                 110

Ser Ala Ile Arg Ser Val Tyr Ser Gly Gln Arg Tyr Ile Ala Ser Asp
        115                 120                 125

Ile Ala Gln Gln Met Ala Leu Ser Gln Ile Glu Pro Glu Lys Thr Glu
    130                 135                 140

Ser Pro Phe Ala Ser Leu Ser Glu Arg Glu Leu Gln Ile Met Leu Met
145                 150                 155                 160

Ile Thr Lys Gly Gln Lys Val Asn Glu Ile Ser Glu Gln Leu Asn Leu
                165                 170                 175

Ser Pro Lys Thr Val Asn Ser Tyr Arg Tyr Arg Met Phe Ser Lys Leu
            180                 185                 190

Asn Ile His Gly Asp Val Glu Leu Thr His Leu Ala Ile Arg His Gly
        195                 200                 205

Leu Cys Asn Ala Glu Thr Leu Ser Ser Gln
    210                 215


<210> SEQ ID NO 106
<211> LENGTH: 840
<212> TYPE: DNA
<213> ORGANISM: Escherichia coli

<400> SEQUENCE: 106

cgaataccca ccatttttaa cgtttcaaag ttgcaataaa aaccgctaat atacgaatga     60

ctaactatca gtagcgttat ccctatttct ggagatattc ctttgatcaa cgttctactt    120

gttgatgacc acgaactggt gcgcgcaggg atacgacgca ttctggaaga tataaagggt    180

ataaaagtcg tcggtgaggc atcgtgcggt gaagacgccg ttaagtggtg ccggacaaat    240

gccgttgacg tggtgctaat ggacatgagt atgccgggca ttggcggtct tgaggcgacg    300

cgtaaaatcg cgcgttccac agctgatgtc aaaatcatca tgcttaccgt ccatacagaa    360

aacccttac cagcgaaagt catgcaggcc ggtgctgcgg gctacctcag caaaggcgcg    420

gctccgcagg aagtcgtgag tgcgattcgt tctgtctatt cagggcagcg ttacattgct    480

tctgacatcg ctcaacaaat ggcgttaagc cagatcgaac cagaaaaaac agaaagccca    540

tttgccagtt tgtctgaacg tgaattgcag attatgctga tgatcaccaa gggccagaag    600

gtcaatgaga tctcagaaca gctcaatctc agtccgaaaa cggtgaacag ctaccgctat    660

cgtatgttca gtaaactaaa cattcatggc gatgttgagc tgactcacct ggcaattcgc    720

catggtctgt gtaatgcgga gacattatca agtcagtgag tgatcagttt gacgcaaaag    780

cgtttttaaa aaccgtaacc agccagccag gcgtttatcg catgtacgat gctggtggta    840
```